United States Patent
Caldwell et al.

(10) Patent No.: US 8,809,622 B2
(45) Date of Patent: Aug. 19, 2014

(54) METHODS AND COMPOSITIONS FOR IDENTIFYING DOWNY MILDEW RESISTANT CUCUMBER PLANTS

(75) Inventors: David Caldwell, St Louis, MO (US); Eva Chan, Davis, CA (US); Jeroen de Vries, The Hague (NL); Tarek Joobeur, Sacramento, CA (US); Joseph King, Davis, CA (US); Antonio Reina, Almeria (ES); Nischit Shetty, Ft. Myers, FL (US)

(73) Assignee: Seminis Vegetable Seeds, Inc., Woodland, CA (US)

(*) Notice: Subject to any disclaimer, the term of this patent is extended or adjusted under 35 U.S.C. 154(b) by 237 days.

(21) Appl. No.: 12/910,478

(22) Filed: Oct. 22, 2010

(65) Prior Publication Data

US 2011/0126309 A1    May 26, 2011

Related U.S. Application Data

(60) Provisional application No. 61/254,141, filed on Oct. 22, 2009.

(51) Int. Cl.
*A01H 1/02* (2006.01)
*A01H 1/04* (2006.01)

(52) U.S. Cl.
USPC ........................................ 800/267; 800/260

(58) Field of Classification Search
None
See application file for complete search history.

(56) References Cited

U.S. PATENT DOCUMENTS

| | | | |
|---|---|---|---|
| 2009/0170703 | A1 | 7/2009 | Van Den et al. |
| 2009/0265803 | A1 | 10/2009 | Shetty et al. |

FOREIGN PATENT DOCUMENTS

| | | |
|---|---|---|
| WO | WO 2007/053015 A2 | 5/2007 |
| WO | WO 2009/129314 | 10/2009 |

OTHER PUBLICATIONS

Block et al (HortScience 40(2): 416-420, 2005).*
Angelov et al., "Selecting downy mildew-resistant short-fruited cucumbers," In: Proceedings of *Curbitaceae* 2000: The 7th Eucarpia Meeting on Cucurbit Genetics and Breeding, *Acta Hort.*, 510:135-137, 2000.
Angelov et al., "Two races of *Pseudoperonospora cubenis* on cucumbers in Bulgaria," *Acta Horticulturae*, 510: 81-84, 2000.
Bakr et al., "Genetics of resistance to downy mildew in cucumbers," *HortScience*, 28(5):506, 1993.
Call, "Studies on resistance to downy mildew in Cucumber (*Cucumis sativus* L.) caused by *Pseudoperonospora cubensis*," Thesis, North Carolina State University, 2010.
Cohen, "A laboratory technique for identifying resistance to cucumber downy mildew" *Phytoparasitica*, 4(3):209, 1976.
Cohen, "Quantitation of resistance of cucumbers and cantaloupe to *Pseudoperonospora cubensis*," *Phytoparasitica*, 4(1):25-31, 1976.
Criswell et al., "Screening cucumber for resistance to the new downy mildew," PPI 2007 Annual Meeting and Pickle Fair, Memphis, TN, Oct. 4, 2007.

(Continued)

*Primary Examiner* — Shubo (Joe) Zhou
*Assistant Examiner* — Keith Robinson
(74) *Attorney, Agent, or Firm* — Dentons US LLP; Matthew L. Madsen Esq.

(57) ABSTRACT

The present invention relates to methods for identifying cucumber lines having increased resistance to Downy Mildew, and identification of genetic markers linked to gene(s) conditioning such increased disease resistance. The present invention also relates to methods of breeding cucumber plants from lines having increased Downy Mildew resistance by marker-assisted selection, compositions including nucleic acid probes or primers which are useful for such marker assisted selection, and plants and plant parts produced by such methods.

26 Claims, 10 Drawing Sheets

(56) References Cited

OTHER PUBLICATIONS

Criswell, "Screening Cucumber (*Cucumis sativus* L.) for resistance to downy mildew caused by *Pseudoperonospora cubensis*," Thesis, North Carolina State University, Horticultural Science, 2008.
Dhillon et al., "Evaluation of landraces of cucumber (*Cucumis sativus* L.) for resistance to downy mildew (*Pseudoperonospora cubensis*)," *Plant Genetics Resources Newsletter*, 119:59-61, 1999.
Doruchowski et al., "F1 hybrid pickling cucumbers developed for increased yield, earliness and resistance to downy mildew (*Pseudoperonospora cubensis*)," *Acta Hort.*, 510:45-46, 2000.
Doruchowski et al., "Tolerance of polish new cucumber F1 hybrids to downy mildew (*Pseudoperonospora cubensis* Berk & Curt) and limitation or elimination chemical disease control," *Acta Hort.*, 371:129-133, 1994.
Fan et al., "Population development by phenotypic selection with subsequent marker-assisted selection for line extraction in cucumber (*Cucumis sativus* L.,)," *Theor. Appl. Genet.*, 112:843-855, 2006.
GenBank Accession No. CC098454, Apr. 16, 2003.
Horejsi et al., "Linkage of random amplified polymorphic DNA markers to downy mildew resistance in cucumber (*Cucumis sativus* L.)," *Euphytica*, 115:105-113, 2000.
Horejsi et al., "Tagging a downy mildew resistance gene in cucumber using RAPD markers," *HortSci.*, 31(4):624, 1996.
Horejsi, "Random amplified polymorphic DNA and sequence characterized amplified regions for studies of genetic diversity and downy mildew resistance in cucumber," Dissertation, Ph.D.—Plant Breeding and Plant Genetics, University of Wisconsin, 1998.
Jurjevic et al., "Tolerance of pickling cucumber cultivars to downy mildew infection *Pseudoperonospora cubensis* (Berk. Et Curt.) rostow and its effect on yield," *Fragmentia Phytomedica et Herbologica*, 24(2):15-27, 1996, (Certified translation).
Lebeda et al., "Peroxidase isozyme polymorphism as a potential marker for detection of field resistance in *Cucumis sativus* to cucumber downy mildew (*Pseudoperonospora cubensis* (Berk. Et Curt.) Rostov.)," *J. of Plant Diseases & Protect.*, 102(5):467-471, 1995.
Lebeda, "Cucurbit downy mildew (*Pseudoperonospora cubensis*)—biology, ecology, epidemiology, host-pathogen interaction and control," *Eur. J. Plant Pathol.*, DOI 10.1007/s10658-010-9658-1, Jul. 25, 2010.
Lebeda, "Screening of wild *Cucumis* species against downy mildew (*Pseudoperonospora cubensis*) isolates from cucumbers," *Phytoparasitica*, 20(3):203-210, 1992.
Lebeda, "Susceptibility of accessions of *Cucumis sativus* to *Pseudoperonospora cubensis*," *Tests of Agrochemicals and Cultivars*, 13:102-103, 1992.
Lisitsyn et al., "Evaluation of specimen cucumber cultivars for breeding against bacteriosis and downy mildew," *Ukrainian Research Institute of Vegetable Crops and Melon Production*, 35:82-84, 1990. (Certified translation).
Luo Guifen et al., "Relationship of sugar and lignin content in cucumber leaves to induced resistance to downy mildew," *Acta Phytopathologica Sinica*, 27(1):65-69, 1997, (Certified Translation).
McFerson et al., "Cucumber resistance to downy mildew in the laboratory greenhouse and field," *HortSci.*, 13(3)(Supp.):344, 1978.
Medvedeva et al., "Agrobiological evaluation of specimen cucumber cultivars promising for breeding against downy mildew," *Trudy Po Prikladnoi Botanike, Genetike I Selektsii*, 77:25-28, 1983. (Certified Translation).
Neykov et al., "Introduced cucumber cultivars relatively resistant to *Pseudoperonospora cubensis* in Bulgaria," *Acta Hort.*, 220:115-119, 1987.
Pados et al., "Further results in the cultivation of *Peronospora*-resistant cucumber species," *Novenyvedelem*, 24(7):311. (Certified Translation).
Pershin et al., "Quantitative approach to genetical study of plant resistance to diseases. IV. Interaction of genetic systems of cucumber resistance to powdery and downy mildew," *Genetika*, 24(3):484-493, 1988. (Certified Translation).

Pershin et al., "Quantitative approach to the study of genetics of disease resistance in plants—IV. Interaction of genetic systems of powdery mildew and downy mildew resistance in cucumber," *Soviet Genetics*, 24(3):333-340, 1988.
Petrov et al., "Resistance to downy mildew, *Pseudoperonospora cubensis*, in cucumbers," *Acta Hort.*, 510:203-209, 2000.
Pierce et al., "Review of genes and linkage groups in cucumber," *Hort. Sci.*, 25(6):605-615, 1990.
Pivovarov, "Cucumber breeding for resistance to false mildew (*Pseudoperonospora cubensis* R.) using various ecological-geographic zones," In: Eucarpia: Proc. of the 3rd Meeting on Breeding of Cucumbers an Melons, pp. 40-46, Jul. 2-5, 1984, Plovdiv, Bulgaria.
Reddy et al., "Evaluation of cucumber genotypes for their performance and resistance to downy mildew disease." *Ad. Agric. Res. India*, 7(7):175-1771997.
Ren et al., "An integrated genetic and cytogenetic map of the cucumber genome," *PLOS One*, 4(6)(e5795):1-8, Jun. 4, 2009.
Sakata et al., "QTL analysis of powdery mildew resistance in cucumber (*Cucumis sativus* L.)," *Theor Appl Genet*, 112:243-250, 2006.
Savory et at , "The cucurbit downy mildew pathogen *Pseudoperonospora cubensis*," *Mol. Plant Pathol.*, DOI: 10.1111/J. 1364-3703.2010.00670.X, 2010.
Sheity et al., "Evidence for downy mildew races in cucumber tested in Asia, Europe, and North America," *Scientia Horticulturae*, 94:231-239, 2002.
St. Amand et al. Crop loss to 14 diseases in cucumber in North Carolina for 1983 to 1988, *Cucurbit Genetics Coop.*, 14:15-17, 1991.
Staub et al., "Evaluation of cucumber germplasm for six pathogens," In: Proceedings *Cucurbitaceae* 89: evaluation and enhancement of cucurbit germplasm, pp. 149-153, Thomas (Ed.), Charleston, SC, Nov. 29-Dec. 2, 1989.
Staub et al., "Selection for multiple disease resistance reduces cucumber yield potential," *Euphytica*, 67:205-213, 1993.
Tarakanov et al., "On the methodology for breeding cucumbers for resistance to downy mildew," In: Selektsiya, Semenovostvo I Sortovaya Tekhnologiya Proizvodstva Ovoshchei, pp. 13-17, 1998. (Certified Translation).
van Vliet et al., "Inheritance of resistance to *Pseudoperonospora cubensis* Rost. In cucumber (*Cucumis sativus* L.)," *Euphytica*, 23:251-255, 1974.
van Vliet et al., "Relation in the inheritance of resistance to *Pseudoperonospora cubensis* Rost and *Sphaerotheca fuliginea* poll. in cucumber (*Cucumis sativus* L.)," *Euphytica*, 26:793-796, 1977.
Weber et al., "The resistance of cucumbers to cucumber mosaic virus, powdery mildew (*Spaerotheca fuliginea* [schlecht et fr.] pollaci) and downy mildew (*Pseudoperonospora cubensis* [Berk. Et Curt] Rostov) . . . " *Arch Phytopathol Pflanzenschutz*, 27(5):361-367, 1991. (Certified Translation).
Wehner et al., "Downy mildew resistance of the cucumber germplasm collection in North Carolina field tests," *Crop Sci.*, 37:1331-1340, 1997.
Woltman et al., Evaluation of cucumber (*Cucumis sativus*) cultivars grown in eastern Europe and progress in breeding for resistance to angular leaf spot (*Pseudomonas syringae* pv. Lachrymans), *Eur. J. Plant Path.*, 122:385-393, 2008.
Yeboah et al., "A genetic linkage map of cucumber (*Cucumis sativus* L.) combining SRAP and ISSR markers," *African Journal of Biotechnology*, 6(24):2784-2791, Dec. 17, 2007.
International Search Report regarding Application No. PCT/US2010/53812, dated Mar. 30, 2010.
Office Action regardind U.S. Application No. 12/424,452, dated Apr. 8, 2011.
Office Action concerning U.S. Appl. No. 12/424,452 issued on Jul. 20, 2011.
Reponse to Office Action concerning U.S. Appl. No. 12/424,452 filed on Sep. 20, 2011.
Bradeen et al., "Towards an Expanded and integrated linkage map of cucumber (*Cucumis sativus* L.)," *Genome*, NRC Canada, 44(1):111-119, 2001.
Database EMBL., XP002693073, 2004.
Ding et al., "A Novel RAPD and SCAR Marker of the Resistant Gene for Downy Mildew (*dm*) in Cucumber," *Acta Bot. Boreal.-Occident. Sin.*, 27(9):1747-1751, 2007.

(56) References Cited

OTHER PUBLICATIONS

Huang et al., "The genome of the cucumber, *Cucumis sativus* L.," *Nature Genetics*, 41(12):1275-1281, 2009.
Meglic et al., "Genetic diversity in cucumber (*Cucumis sativus* L.): II. An evaluation of selected cultivars released between 1846 and 1978," *Genetic Resources and Crop Evolution*, 43(6):547-558, 1996.
Smiech et al., "Attempt to select cucumber (*Cucumis sativus*) double haploid lines to downy mildew tolerance by molecular markers," *Cucurbitaceae 2008: Proceedings of the IXth EUCARPIA meeting on genetics and breeding of Cucurbitaceae*, pp. 441-444, 2008.
Wan et al., "Identification and characterization of potential NBS-encoding resistance genes and induction kinetics of a putative candidate gene associated with downy mildew resistance in *Cucumis*," *BMC Pl. Biol.*, 10(1):186, 2010.
Zhou et al., "Molecular analysis of introgression lines from *Cucumis hystrix* Chakr. to *C. sativus* L.," *Scienta Horticulturae*, 119(3):232-235, 2009.
Call et al., "Screening Cucumber for Resistance to Downy Mildew Caused by *Pseudoperonospora cubensis* (Berk. and Curt.) Rostov," *Crop Sci.*, vol. 52, pp. 577-592, Mar.-Apr. 2012.
Monsanto, "Introducing Seminis® Downy Mildew Resistant Cucumbers- Farm on your own Terms," brochure from us.seminis.com; 2012.
Response to Office Action for U.S. Appl. No. 12/424,452 dated Nov. 26, 2012.
USPTO; Office Action for U.S. Appl. No. 12/424,452 dated Dec. 12, 2012.
USPTO: Request for Continued Prosecution; Telephonic Interview Summary and Response to Final Office Action for U.S. Appl. No. 12/424,452 dated May 13, 2013.
USPTO: Non- Final Office Action for U.S. Appl. No. 12/424,452 dated Sep. 27, 2013.
Block et al., "Powdery Mildew Resistance in the U.S. National Plant Germplasm System Cucumber Collection", *HortScience* 40(2):416-420, 2005.
USDA, ARS, National Genetic Resources Program. Germplasm Resources Information Network—(GRIN). [Online Database] National Germplasm Resources Laboratory, Beltsville, Maryland. Available: http://www.ars-grin.gov/cgi.retrieved on Jun. 12, 2012.
USDA, ARS, National Genetic Resources Program. Germplasm Resources Information Network—(GRIN). [Online Database] National Germplasm Resources Laboratory, Jun. 12, 2012 Beltsville, Maryland. Available: http://www.ars-grin.gov/cgi-bin/npgs/html/cno_acc.pl?56705.
Office Action concerning U.S. Appl. No. 12/424,452 dated Jul. 31, 2012.
Response to Office Action concerning U.S. Appl. No. 12/424,452 filed on Jun. 20, 2012.
Office Action concerning U.S. Appl. No. 12/424,452 dated Mar. 19, 2012.
Response to Office Action regarding U.S. Appl. No. 12/424,452, dated Dec. 23, 2013.
Office Action regarding U.S. Appl. No. 12/424,452, dated Feb. 21, 2014.
USPTO; Notice of Allowance for U.S. Appl. No. 12/424,452, dated Mar. 25, 2014.
USPTO; Response to Final Office Action for U.S. Appl. No. 12/424,452, dated Mar. 10, 2011.

\* cited by examiner

| cM | Markers |
|---|---|
| 0.0 | G-NN0247539 G-NN0247710 |
| 0.2 | G-NN0224680 |
| 2.2 | G-NN0247583 G-NN0228802 |
| 3.0 | G-NN0247706 |
| 3.8 | G-NN0225493 G-NN0224596 |
| | G-NN0225810 |
| 7.5 | G-NN0225975 |
| | G-NN0224796 G-NN0224711 |
| 7.6 | G-NN0228893 |
| 10.4 | G-NN0223763 |
| 12.6 | G-NN0225383 |
| 12.8 | G-NN0228856 |
| 18.1 | G-NN0225012 |
| 18.3 | G-NN0225260 |
| 18.4 | G-NN0223863 |
| 18.8 | G-NN0246870 |
| 21.3 | G-NN0246393 |
| 22.7 | G-NN0229054 |
| 23.4 | G-NN0228579 G-NN0225143 |
| 25.3 | G-NN0226440 |
| 25.6 | G-NN0224450 |
| 25.8 | G-NN0226451 |
| 29.4 | G-NN0229028 |
| 29.5 | G-NN0227018 |
| 29.6 | G-NN0247182 G-NN0226204 |
| | G-NN0225345 |
| | G-NN0225150 G-NN0224867 |
| 29.7 | G-NN0224343 G-NN0224838 |
| | G-NN0225088 |
| | G-NN0226219 G-NN0247330 |
| 32.5 | G-NN0226218 |
| 33.9 | G-NN0227979 G-NN0224445 |
| 37.0 | G-NN0228796 |
| 37.5 | G-NN0247100 G-NN0247134 |
| 39.0 | G-NN0246914 |
| 39.2 | G-NN0246357 |
| 44.0 | G-NN0247712 |
| 46.4 | G-NN0247725 |
| 46.6 | G-NN0224211 G-NN0246632 |
| 47.1 | G-NN0225551 G-NN0225070 |
| 47.7 | G-NN0225339 |
| 49.8 | G-NN0228715 |
| 50.4 | G-NN0227873 |
| 50.5 | G-NN0228883 |
| 51.0 | G-NN0224961 |
| 51.3 | G-NN0227475 |
| 51.5 | G-NN0226732 |
| 51.6 | G-NN0226692 |
| 52.4 | G-NN0247689 |
| 54.7 | G-NN0223084 |
| 55.0 | G-NN0226586 |
| 56.4 | G-NN0228536 |
| 56.7 | G-NN0247342 G-NN0247635 |
| | G-NN0247529 G-NN0247771 |
| 65.1 | G-NN0224702 G-NN0228031 |
| | G-NN0223414 G-NN0224353 |
| 67.5 | G-NN0224265 |
| 69.1 | G-NN0225553 G-NN0225482 |
| 69.4 | G-NN0225081 |
| 69.6 | G-NN0246425 G-NN0224538 |
| | G-NN0223940 |
| 69.9 | G-NN0227048 |
| 74.3 | G-NN0227617 G-NN0227631 |
| 75.2 | G-NN0223832 G-NN0223094 |
| 75.8 | G-NN0223626 |
| 79.8 | G-NN0247543 |
| 79.9 | G-NN0226776 |
| 80.0 | G-NN0227379 |
| 81.2 | G-NN0224067 G-NN0227315 |
| 82.0 | G-NN0224041 |
| 82.5 | G-NN0223103 |
| 86.3 | G-NN0225814 |
| 89.6 | G-NN0227015 G-NN0228853 |
| 90.7 | G-NN0224495 |
| 90.9 | G-NN0226226 |
| 91.2 | G-NN0247486 |
| 91.7 | G-NN0226543 |
| 92.6 | G-NN0227762 |
| 92.7 | G-NN0224069 |
| 92.9 | G-NN0227182 |
| 93.2 | G-NN0227279 G-NN0227285 |
| 94.0 | G-NN0227587 G-NN0247726 |
| 95.3 | G-NN0247782 |
| 96.2 | G-NN0246417 G-NN0223422 |
| 99.5 | G-NN0247555 |
| 101.5 | G-NN0226481 |
| 104.2 | G-NN0226865 |
| 104.4 | G-NN0224050 |
| 104.5 | G-NN0247421 |
| 105.3 | G-NN0223754 |
| 105.8 | G-NN0223896 G-NN0226220 |
| 107.0 | G-NN0225734 |
| 107.7 | G-NN0228805 G-NN0225208 |
| 107.8 | G-NN0246631 |
| 108.0 | G-NN0246308 G-NN0246722 |
| 108.8 | G-NN0227111 G-NN0247623 |
| | G-NN0225987 G-NN0223759 |
| | G-NN0223284 G-NN0224972 |
| | G-NN0223295 |
| | G-NN0228925 G-NN0226554 |
| | G-NN0226559 |

D.

| cM | Markers |
|---|---|
| 0.0 | G-NN0247539 G-NN0247710 |
| 1.2 | G-NN0224680 |
| 5.8 | G-NN0228802 G-NN0247583 |
| 8.6 | G-NN0224596 G-NN0225810 |
| | G-NN0225493 |
| 11.8 | G-NN0224796 G-NN0224711 |
| 16.2 | G-NN0225383 G-NN0228856 |
| 21.7 | G-NN0246870 |
| 22.3 | G-NN0225260 |
| 22.8 | G-NN0225012 G-NN0223863 |
| 23.9 | G-NN0226079 G-NN0247573 |
| 24.5 | G-NN0246309 |
| 24.6 | G-NN0228250 |
| 28.8 | G-NN0228579 G-NN0225143 |
| 29.6 | G-NN0226451 G-NN0224450 |
| | G-NN0226440 |
| 33.0 | G-NN0225345 G-NN0229028 |
| | G-NN0224867 G-NN0223589 |
| | G-NN0224838 G-NN0225150 |
| 33.2 | G-NN0227010 G-NN0225088 |
| | G-NN0224343 G-NN0226074 |
| | G-NN0224864 |
| 33.9 | G-NN0227999 G-NN0228029 |
| 34.0 | G-NN0227972 |
| 34.4 | G-NN0224664 G-NN0224593 |
| | G-NN0223316 G-NN0247603 |
| 35.2 | G-NN0226219 G-NN0226218 |
| 35.9 | G-NN0224445 G-NN0227979 |
| | G-NN0247551 G-NN0224414 |
| | G-NN0228842 G-NN0228836 |
| 37.6 | G-NN0224320 G-NN0224932 |
| | G-NN0227183 |
| | G-NN0227879 G-NN0224535 |
| 37.9 | G-NN0246369 G-NN0223339 |
| 40.0 | G-NN0247100 G-NN0247134 |
| 42.1 | G-NN0225107 |
| 43.4 | G-NN0228630 |
| 43.8 | G-NN0247712 |
| 44.1 | G-NN0224464 |
| 44.6 | G-NN0224762 |
| 46.0 | G-NN0229090 G-NN0224390 |
| 48.7 | G-NN0225070 |
| 49.8 | G-NN0247208 |
| 50.9 | G-NN0225339 |
| 51.7 | G-NN0228715 |
| 52.9 | G-NN0227873 |
| 53.4 | G-NN0228883 |
| 53.5 | G-NN0247743 |
| | G-NN0223888 G-NN0226692 |
| 53.6 | G-NN0229056 G-NN0227475 |
| | G-NN0226656 |
| 53.8 | G-NN0227120 |
| 53.9 | G-NN0226732 G-NN0224961 |
| 56.0 | G-NN0247529 G-NN0247635 |
| 63.5 | G-NN0224702 |
| 67.4 | G-NN0224265 |
| 67.7 | G-NN0225482 G-NN0225553 |
| | G-NN0223654 G-NN0224572 |
| 68.4 | G-NN0224106 G-NN0224111 |
| | G-NN0228930 |
| 68.7 | G-NN0225081 G-NN0223940 |
| | G-NN0227048 G-NN0224538 |
| 72.7 | G-NN0223094 G-NN0223832 |
| 73.0 | G-NN0247543 |
| 76.8 | G-NN0224041 G-NN0227315 |
| 77.6 | G-NN0223124 |
| 79.9 | G-NN0225814 |
| 82.5 | G-NN0246738 |
| 84.8 | G-NN0247668 G-NN0226086 |
| 86.0 | G-NN0227762 |
| 86.3 | G-NN0224069 |
| 87.7 | G-NN0227285 G-NN0227182 |
| | G-NN0227587 G-NN0227279 |
| 88.0 | G-NN0247726 |
| 88.9 | G-NN0223422 G-NN0246417 |
| | G-NN0247555 G-NN0247615 |
| 89.4 | G-NN0227211 |
| 89.9 | G-NN0226865 |
| 91.3 | G-NN0225826 |
| 91.6 | G-NN0224777 |
| 91.9 | G-NN0224050 |
| 92.3 | G-NN0228716 G-NN0223906 |
| 92.8 | G-NN0227419 |
| 92.9 | G-NN0223710 |
| 93.1 | G-NN0227942 |
| 94.8 | G-NN0247421 G-NN0223715 |
| 97.5 | G-NN0227586 |
| | G-NN0224793 G-NN0225471 |
| 97.8 | G-NN0225404 |
| | G-NN0224127 G-NN0246631 |
| 99.2 | G-NN0224125 G-NN0223571 |
| 99.3 | G-NN0223295 G-NN0228925 |
| 99.4 | G-NN0223284 |
| 99.5 | G-NN0225987 |
| | G-NN0226554 G-NN0224972 |
| 100.7 | G-NN0227111 |
| 101.0 | G-NN0226559 |
| | G-NN0223718 G-NN0223742 |

SEQUENCE LISTING

<160> NUMBER OF SEQ ID NOS: 87

<210> SEQ ID NO 1
<211> LENGTH: 29
<212> TYPE: DNA
<213> ORGANISM: Artificial Sequence

```
<220> FEATURE:
<223> OTHER INFORMATION: Synthetic primer

<400> SEQUENCE: 1
gaatagatag gctacacttt tccctcttg                                29

<210> SEQ ID NO 2
<211> LENGTH: 31
<212> TYPE: DNA
<213> ORGANISM: Artificial Sequence
<220> FEATURE:
<223> OTHER INFORMATION: Synthetic primer

<400> SEQUENCE: 2
gtataaaact tgagtgaatt taatgcatga a                             31

<210> SEQ ID NO 3
<211> LENGTH: 35
<212> TYPE: DNA
<213> ORGANISM: Artificial Sequence
<220> FEATURE:
<223> OTHER INFORMATION: Synthetic primer

<400> SEQUENCE: 3
tgtttcataa ctacagcttc atgttaaata ttact                         35

<210> SEQ ID NO 4
<211> LENGTH: 25
<212> TYPE: DNA
<213> ORGANISM: Artificial Sequence
<220> FEATURE:
<223> OTHER INFORMATION: Synthetic primer

<400> SEQUENCE: 4
tagtttcttt cttgctggac gaacc                                    25

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
tatgggctat gtgaaactct t                                        21

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
agcgtgacaa ctacaaaaca t                                        21

<210> SEQ ID NO 7
<211> LENGTH: 23
<212> TYPE: DNA
<213> ORGANISM: Artificial Sequence
<220> FEATURE:
<223> OTHER INFORMATION: Synthetic primer

<400> SEQUENCE: 7
gaaataaatg gatgaagcga gga                                      23
```

<210> SEQ ID NO 8
<211> LENGTH: 27
<212> TYPE: DNA
<213> ORGANISM: Artificial Sequence
<220> FEATURE:
<223> OTHER INFORMATION: Synthetic primer

<400> SEQUENCE: 8
gttcgttgat cagtgtgata tttcaat         27

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
atcggtcttt gccacctttt g         21

<210> SEQ ID NO 10
<211> LENGTH: 28
<212> TYPE: DNA
<213> ORGANISM: Artificial Sequence
<220> FEATURE:
<223> OTHER INFORMATION: Synthetic primer

<400> SEQUENCE: 10
aggagggaca gagagaattt gatataat         28

<210> SEQ ID NO 11
<211> LENGTH: 27
<212> TYPE: DNA
<213> ORGANISM: Artificial Sequence
<220> FEATURE:
<223> OTHER INFORMATION: Synthetic primer

<400> SEQUENCE: 11
tccgttttag gtgattgtca aatacat         27

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
tgtttggaag ggtttcttgg g         21

<210> SEQ ID NO 13
<211> LENGTH: 18
<212> TYPE: DNA
<213> ORGANISM: Artificial Sequence
<220> FEATURE:
<223> OTHER INFORMATION: Synthetic primer

<400> SEQUENCE: 13
tgccatgtcg ccaacagt         18

<210> SEQ ID NO 14
<211> LENGTH: 23
<212> TYPE: DNA
<213> ORGANISM: Artificial Sequence
<220> FEATURE:
<223> OTHER INFORMATION: Synthetic primer

```
<400> SEQUENCE: 14
tcaagccata gtctaaccca tgc                                              23

<210> SEQ ID NO 15
<211> LENGTH: 25
<212> TYPE: DNA
<213> ORGANISM: Artificial Sequence
<220> FEATURE:
<223> OTHER INFORMATION: Synthetic primer

<400> SEQUENCE: 15
cgctatatca tggatggcta gaaat                                            25

<210> SEQ ID NO 16
<211> LENGTH: 30
<212> TYPE: DNA
<213> ORGANISM: Artificial Sequence
<220> FEATURE:
<223> OTHER INFORMATION: Synthetic primer

<400> SEQUENCE: 16
aaagttgata gtgcatgagt tggtaaaata                                       30

<210> SEQ ID NO 17
<211> LENGTH: 22
<212> TYPE: DNA
<213> ORGANISM: Artificial Sequence
<220> FEATURE:
<223> OTHER INFORMATION: Synthetic primer

<400> SEQUENCE: 17
tccgcttatg ggtttttgtg ag                                               22

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
tatgggctat gtgaaactct t                                                21

<210> SEQ ID NO 19
<211> LENGTH: 21
<212> TYPE: DNA
<213> ORGANISM: Artificial Sequence
<220> FEATURE:
<223> OTHER INFORMATION: Synthetic primer

<400> SEQUENCE: 19
agcgtgacaa ctacaaaaca t                                                21

<210> SEQ ID NO 20
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 20
ttcatacgcc gttgcagctg aaagtggcaa ccattacttc cagatcatta tgacaataaa      60
```

```
yaaccaaggc caccttcatg cataaatggt aagataatag caagctctat accttctttt    120
t                                                                   121

<210> SEQ ID NO 21
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 21
tcttgatcaa tccaactggg ttggaactca aattcaagaa atggggttta atcacaacca    60
ygttcaatct caattttcag attccgccat ccccccccact ccctatactc aacctcctga   120
c                                                                   121

<210> SEQ ID NO 22
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: m is a or c

<400> SEQUENCE: 22
ggtttagatg aaaagaagta tgcattcatg cttttgcaca aaggcattcc tggctttcaa    60
mtagctgtat ctcttgcagg gatataaatg gatgcaacac tcttttcagt gaaagaaatc   120
c                                                                   121

<210> SEQ ID NO 23
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 23
ggatcattat ttatccaacg tattagcaag ctctaataga aacacttcct aaagaacata    60
ycgatccaaa ttatatgcta agagaattac ccaacatttg agcaagttta ctgactacag   120
c                                                                   121

<210> SEQ ID NO 24
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: r is a or g

<400> SEQUENCE: 24
tagaaaacaa gaatggttct caaagaacct accgaccgaa ttggttgagg atgagatgac    60
raatagaaac attaataata tggtggagga ggaggcgatc gatgaaccgt cgcaaagcat   120
t                                                                   121

<210> SEQ ID NO 25
<211> LENGTH: 121
```

```
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: r is a or g

<400> SEQUENCE: 25
ccacgaatgg aatcaatgaa ttcacgagca acctataata agagagtgga aaacaaaact    60
rctccttcac catctaagaa aacaatgtat aaaaatcaga gaaggaaaga taaagatac   120 t                                                                  121

<210> SEQ ID NO 26
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: r is a or g

<400> SEQUENCE: 26
gaagaagagt gcaacaagta agagtctggc tgggggagtt gaagttcatt catggattag    60
rttaacatac gaactttgga ggcgtgcaaa agacaatccc cataacttga ttacgggctt   120
c                                                                  121

<210> SEQ ID NO 27
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 27
aaaatatatg atcctacaac taaataagag tgcacatgaa gataccttat ataggaga     60 yaatgatgtc gtatgtcctg cttgatgatt tcgaagaacc agatgactga agaaggaata  120
a                                                                  121

<210> SEQ ID NO 28
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 28
ggagttaatc gaaggaagaa aatcaactcg tcttaacagc atcacaataa tcaaattctt    60
yaggtatacc tttcttctcc ttgtcactgg actcatcagg atcctcatcg gcgattttgc   120
g                                                                  121

<210> SEQ ID NO 29
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t
```

<400> SEQUENCE: 29
ctctgaagaa ttaccgaagg gggtcggaat tttctctata gcctgcaatg agaggaataa    60
ygaggaatga aaatgttggc tctgtagcac atgaatgaaa tgcggatatt ctgccaaagg   120
c                                                                   121

<210> SEQ ID NO 30
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 30
agaacaaccc ccaacgtccc aaaatcacta catctccaac cctttcttct cctcatcatt    60
yagttttagt ctctgttttg tggaactctc aaatgaaatt gcttgaatac tcttgataaa   120
a                                                                   121

<210> SEQ ID NO 31
<211> LENGTH: 116
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 31
accaaaaatg aaataaaatc aggctccacc ttcaccttgc agtaatatga tggcagtacg    60
ytgcattgta aaccatgtta atagaagaaa agaactgtga gaaatacta gaattc        116

<210> SEQ ID NO 32
<211> LENGTH: 89
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: s is c or g

<400> SEQUENCE: 32
cggatgagga tttcaggtgt tttttctaaa caaatgtttg cccttttaaac atgcgtttgc    60 sgattctggt ttatttgttt tcggttgat                                      89

<210> SEQ ID NO 33
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: r is a or g

<400> SEQUENCE: 33
actatcctaa tactacggaa ttggtgtgga gaacagaaca gttatttggt ttgttcgaaa    60
rtctcgacaa ctttcgatcg atcactcttg ttaggggta tcccaactac atcataagca   120
a                                                                   121

<210> SEQ ID NO 34
<211> LENGTH: 121

<212> TYPE: DNA
<213> ORGANISM: Cucumis sativus
<220> FEATURE:
<221> NAME/KEY: misc_feature
<222> LOCATION: (61)..(61)
<223> OTHER INFORMATION: r is a or g

<400> SEQUENCE: 34
actatcctaa tactacggaa ttggtgtgga gaacagaaca gttatttggt ttgttcgaaa    60
rtctcgacaa ctttcgatcg atcactcttg ttaggggta tcccaactac atcataagca   120
a                                                                  121

<210> SEQ ID NO 35
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 35
tgcttcttga tcttgctaat gtaaagagat atcacttaca tgaaaggctt tccgagtcat    60
ygtcaatttc tgcactggga ggcttttggt cattgctctt gaataccaca ttcccatatt   120
t                                                                  121

<210> SEQ ID NO 36
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 36
gagtttccaa aattgaacat cttcaatgga cagaaagttt tgaagtagca agacttaagg    60
yttccacttg gtgttcctta tctaagttct cgaacaattt gcatttgatt tcttaaatat   120
t                                                                  121

<210> SEQ ID NO 37
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: w is a or t

<400> SEQUENCE: 37
taatagttac atgatgcttt attgctacta tatatgttca gaaatattat ccagatgcga    60
watattttca gacactgctg tgaatgttat ttggactaac gaaacttgtt attttgtgct   120
g                                                                  121

<210> SEQ ID NO 38
<211> LENGTH: 121
<212> TYPE: DNA
<213> ORGANISM: Cucumis sativus
<220> FEATURE:
<221> NAME/KEY: misc_feature
<222> LOCATION: (13)..(13)
<223> OTHER INFORMATION: n is a, t, c, or g
<220> FEATURE:

```
<221> NAME/KEY: misc_feature
<222> LOCATION: (61)..(61)
<223> OTHER INFORMATION: r is a or g

<400> SEQUENCE: 38
gtttacatga aantatgcac acacccaaag atatgttgat taagatgata agttcccaag      60
ratagaagaa ttatgtgtgt attgcttctt tgatgtccag gaactaatga gatttatctg    120
g                                                                    121

<210> SEQ ID NO 39
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t
<220> FEATURE:
<221> NAME/KEY: misc_feature
<222> LOCATION: (101)..(101)
<223> OTHER INFORMATION: n is a, t, c, or g

<400> SEQUENCE: 39
tatagccgag caaccgagtc cttagatttg gtttaagagc atctacgaat agatggtcga     60
ytgtatgaat gatgagcaga aacgctcttg aaacggcttc ntcacatttg aactccatgc    120
a                                                                    121

<210> SEQ ID NO 40
<211> LENGTH: 103
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: r is a or g
<220> FEATURE:
<221> NAME/KEY: misc_feature
<222> LOCATION: (94)..(103)
<223> OTHER INFORMATION: n is a, c, g, or t

<400> SEQUENCE: 40
tgatttatct catggagaat accaatgtgc aaaagaaacc aaaggcgttc ttcttcatct     60
rtgtttagct tcgatattgt gtgtagcact gcannnnnnn nnn                      103

<210> SEQ ID NO 41
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 41
agaaattttt taagacaata cttgatatcc ttttcacaat tcagttcatt cctcctataa     60
ytgtgattcc agcaacgatt aggaatgatt tctcaattcc caccttggtg cacatttcaa   120
g                                                                    121

<210> SEQ ID NO 42
<211> LENGTH: 113
<212> TYPE: DNA
<213> ORGANISM: Cucumis sativus
<220> FEATURE:
<221> NAME/KEY: misc_feature
```

<222> LOCATION: (53)..(53)
<223> OTHER INFORMATION: w is a or t

<400> SEQUENCE: 42 ctttattttta ttttcaggtt gctcttaaat ttgagcacag aaatagtaaa ggwtgcaatt    60
atggtcctcc atacgaatgg caagtttaca agtgagtaac ttttttgggtt aca          113

<210> SEQ ID NO 43
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: w is a or t

<400> SEQUENCE: 43
gtacttgtac caatatgaaa tgtgcacatg cgctcttgtc ctagataata tgcacagttc    60
wccttaaaag ctaagcataa gccacaaatc caagaaccaa tgtaaccaaa acagtatggg   120
a                                                                   121

<210> SEQ ID NO 44
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: w is a or t

<400> SEQUENCE: 44
ctgttgccta tgcaaagcat ttatacagct tcattctgcc attttaacga atgttcactg    60
wagtacctga gatggcttcc aaaactgtct tgtaaggtgt gcctctcatc tgcatctgtc   120
t                                                                   121

<210> SEQ ID NO 45
<211> LENGTH: 116
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: m is a or c

<400> SEQUENCE: 45 tcttttata cttttctgat cttgtaaagt ttaaggcttt caactggtgt agtgtagtca     60
mcagaagtct ttttataatt gttacacttt aatttgatag gaaagtgttt ctttaa       116

<210> SEQ ID NO 46
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: s is c or g

<400> SEQUENCE: 46
gctagtatat ctatatatct ttttgagagc tttatgataa ttatcaaatg aagattctag    60
stgtgtgatc aagagaagat tcctagccta cctcttagct cttttaaaaa ttgtggtagt   120
t                                                                   121

<210> SEQ ID NO 47
<211> LENGTH: 121
<212> TYPE: DNA
<213> ORGANISM: Cucumis sativus
<220> FEATURE:
<221> NAME/KEY: misc_feature
<222> LOCATION: (4)..(4)
<223> OTHER INFORMATION: n is a, c, t, or g
<220> FEATURE:
<221> NAME/KEY: misc_feature
<222> LOCATION: (20)..(20)
<223> OTHER INFORMATION: n is a, c, t, or g
<220> FEATURE:
<221> NAME/KEY: misc_feature
<222> LOCATION: (24)..(24)
<223> OTHER INFORMATION: n is a, c, t, or g
<220> FEATURE:
<221> NAME/KEY: misc_feature
<222> LOCATION: (61)..(61)
<223> OTHER INFORMATION: k is g or t

<400> SEQUENCE: 47
taantttgtt ttcacatttn tttncaaata atatatatct tacagtttag gaggcttctt    60
kcaccattac atataaaaca tatggaacaa acattacctc taaataacca atagacttt   120 a                                                                 121

<210> SEQ ID NO 48
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: w is a or t

<400> SEQUENCE: 48
tctttaaaag aagcttgaaa gatgaagaaa ttgcaaaatt tcaatcattt cgatccctcc    60
wctcacctga aaaagtggtt aattctgatg attttagatc atggtccatt gatccctcaa   120
t                                                                 121

<210> SEQ ID NO 49
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: k is g or t

<400> SEQUENCE: 49
gtccatacta ccataattga taatactaag taccctgaac ctttgagatt tgaatctttc    60
kaccccacag gttgttaaac acaaatacga gtaacaaaga taagatttga actcagcctt   120
t                                                                 121

<210> SEQ ID NO 50
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: r is a or g

<400> SEQUENCE: 50
ttggttcctg atccagaaga aaaatggttg atttccttat gattcttttc agtaaggtgg    60
racaatcttg ctccaggtcc ttcgtcataa aacacccccc tccaaggaag agaaacccca    120
a    121

<210> SEQ ID NO 51
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 51
atttttagat gtgagcctat ttatgtgctc ttaacttctc ttttagtaat ggtggaaatg    60
yaatttgttt atgagcaatg gtatcgtgaa taaatggttg gatacataat agctttgctt    120
g    121

<210> SEQ ID NO 52
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: r is a or g

<400> SEQUENCE: 52
gttgggcttt tttgttgtat tatttctttt tgtcgtatta tgtatctaaa ggcagatgaa    60
racctggatc atattctttg gcaatgtgat tttgcgttgg tgtttgggat tccttttttcc    120 a    121

<210> SEQ ID NO 53
<211> LENGTH: 121
<212> TYPE: DNA
<213> ORGANISM: Cucumis sativus
<220> FEATURE:
<221> NAME/KEY: misc_feature
<222> LOCATION: (20)..(20)
<223> OTHER INFORMATION: n is a, t, c, or g
<220> FEATURE:
<221> NAME/KEY: misc_feature
<222> LOCATION: (61)..(61)
<223> OTHER INFORMATION: r is a or g

<400> SEQUENCE: 53
ttaaacaatt gacccaaaan ttaaagttga tgggtaaagg taaaactaac attatatcac    60
rcaacattcc ctcatttgta gacttgaaat atgtagaaaa gcccattagt gaaaatgaat    120
a    121

<210> SEQ ID NO 54
<211> LENGTH: 121
<212> TYPE: DNA
<213> ORGANISM: Cucumis sativus
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (61)..(61)
<223> OTHER INFORMATION: r is a or g

<400> SEQUENCE: 54
tattttggtg ctaaccgaat agtttgagag ggagaaatag gaaacgatga caacnccatg    60
rattggggga agtgttcgac atttgaaaag gagaataaat caattaaaat tatgcattca   120
a                                                                  121

<210> SEQ ID NO 55
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: w is a or t

<400> SEQUENCE: 55
acacagtatt gataatttcc aaatcaacac ttggaatatt tttgttaaat atgcacgaca    60
watttggttc gttattggtc catgatggta atctatactt catatgaaat tcttatctct   120
a                                                                  121

<210> SEQ ID NO 56
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 56
tatatgttgc taatgtgcta tttttaaaga aaaaataaag gccccatttg gtcatggttt    60
yctctcaatt gttcaattgt actttccaca ttatttgaat aagcaatcca acttttacct   120
a                                                                  121

<210> SEQ ID NO 57
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 57
tgaagaagag cctttattgc gtcatctgga acctccttta tccatttatc ttgaattggt    60
yggtcatgaa cacacccttta ccatttatta ttcaatgcca tgattgtctt acacaggtgt   120
g                                                                  121

<210> SEQ ID NO 58
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: s is c or g

<400> SEQUENCE: 58
agtcgagttt tgagccactc ataacccagt tgaatgcttt taaccttgta gtcactaaca    60
saaacacagt ggaatggtag ttgaagtagg gtcattttgg ctaattcatt gcatgttgtt   120
a                                                                  121

<210> SEQ ID NO 59
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 59

```
tgtccaaaag aaatatatgc tcaaactgtg cctcaatcac cgtcttctct ccaatttcc      60
yatatcattc tcgattatta ctttcctcta tttcatttag tttctaataa ttaataacgg    120
c                                                                     121
```

<210> SEQ ID NO 60
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: r is a or g
<220> FEATURE:
<221> NAME/KEY: misc_feature
<222> LOCATION: (104)..(104)
<223> OTHER INFORMATION: n is a, c, g, or t

<400> SEQUENCE: 60

```
ccgaggcgac ctccggcttg cccgttacaa gttgggagtt gggccttggg ctctcgacgt      60
rggccgagag tccattgctc ctaaagattg gtgggcaccg cgtnaggctg gttcacagag    120
c                                                                     121
```

<210> SEQ ID NO 61
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: s is c or g

<400> SEQUENCE: 61

```
cttctagcca aaataattcc attttttgttt cacaaaatga acctgttgga gggaagacca     60
stgcgctacc catcccaaat tcagattctg gaaatatggc caaagatcat tcattgaggt    120
c                                                                     121
```

<210> SEQ ID NO 62
<211> LENGTH: 121
<212> TYPE: DNA
<213> ORGANISM: Cucumis sativus
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (61)..(61)
<223> OTHER INFORMATION: y is c or t
<220> FEATURE:
<221> NAME/KEY: misc_feature
<222> LOCATION: (110)..(113)
<223> OTHER INFORMATION: n is a, c, t, or g
<220> FEATURE:
<221> NAME/KEY: misc_feature
<222> LOCATION: (121)..(121)
<223> OTHER INFORMATION: n is a, c, t, or g

<400> SEQUENCE: 62
atggagctta gagaaaacga cctagaaant attatcctta ttcatgtcga acgggctgtc    60
yggtaagatt agttgaggtg cgcataatac ctggacactc acaaatatgn nnnaaaaaaa   120 n                                                                  121

<210> SEQ ID NO 63
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: s is c or g

<400> SEQUENCE: 63
atatggaata tttgacaact aattagttac ttctaaaact gcaatagcag tcacgttagt    60
stcccccagg gagagaagaa aatactagaa tttgtgagcc actgttaata gattcaaaat   120
a                                                                  121

<210> SEQ ID NO 64
<211> LENGTH: 104
<212> TYPE: DNA
<213> ORGANISM: Cucumis sativus
<220> FEATURE:
<221> NAME/KEY: misc_feature
<222> LOCATION: (44)..(44)
<223> OTHER INFORMATION: s is c or g
<220> FEATURE:
<221> NAME/KEY: misc_feature
<222> LOCATION: (101)..(101)
<223> OTHER INFORMATION: n is a, t, c, or g

<400> SEQUENCE: 64
ttaggttccc gctattgcaa taccaacaag gcatgaaggc tttsgccaca atgtgaaatc    60
atcaacagtt actatgaaca atgaattcgc taacaggaaa ncgt                   104

<210> SEQ ID NO 65
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: r is a or g

<400> SEQUENCE: 65
tctaattcga tgagtttgtc tgaattccca agtaagaacc aaagttccat tcattctctc    60
ragcacaaac ctttccacca aaacataaca cctaaatctc ttccacattc cctttccttt   120
a                                                                  121

<210> SEQ ID NO 66
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 66
ggagattgtt gcacgcctga agaaagcctt cagaattacc attaagactt cccaactctg    60
yctgcatatt gtcaagaaag ctagagattt tctcagaagc tactttaatg gcagggccct   120

```
c                                                                         121

<210> SEQ ID NO 67
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: s is c or g

<400> SEQUENCE: 67
aggaaaatac cttccaatag aaaacatggt aaatgcaata agcatctagt tcatccaatt        60
scaagggtaa tggctagttc aagatggaac taaaactctc agagtggtgt gtgcaatcct       120
g                                                                       121

<210> SEQ ID NO 68
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: r is a or g

<400> SEQUENCE: 68
ggttacagag tccagagcga tcaatggaga ttgtggatgt tgaaggttca gaagagaagg        60
rtcgttgatt aaggaggtct tcattctcca ggtgctgaac gacagtacct tccggaatct       120
g                                                                       121

<210> SEQ ID NO 69
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is c or t

<400> SEQUENCE: 69
atgatcctca attcatacca tattattgta tgagctaaat gtgtataaag aaaaggaaag        60
ytatagaagg atggattcgt acattaacac aaaggataaa aactgcaaac ttatttatat       120
a                                                                       121

<210> SEQ ID NO 70
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: r is a or g
<220> FEATURE:
<221> NAME/KEY: misc_feature
<222> LOCATION: (97)..(97)
<223> OTHER INFORMATION: n is a, c, g, or t

<400> SEQUENCE: 70
aatgacttat ctagatggat atgataactt caccgattgt tggataaaaa agcaggtgac        60
ragttgtgtt attattgggc agtgatgtat tgttagntaa ccactgaaat tgttaaaatt       120
a                                                                       121
```

<210> SEQ ID NO 71
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: w is a or t

<400> SEQUENCE: 71
tctttaaaag aagcttgaaa gatgaagaaa ttgcaaaatt tcaatcattt cgatccctcc    60
wctcacctga aaaagtggtt aattctgatg attttagatc atggtccatt gatccctcaa   120
t                                                                  121

<210> SEQ ID NO 72
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is t or c

<400> SEQUENCE: 72 attttagat gtgagcctat ttatgtgctc ttaacttctc ttttagtaat ggtggaaatg     60
yaatttgttt atgagcaatg gtatcgtgaa taaatggttg gatacataat agctttgctt   120
g                                                                  121

<210> SEQ ID NO 73
<211> LENGTH: 101
<212> TYPE: DNA
<213> ORGANISM: Cucumis sativus
<220> FEATURE:
<221> NAME/KEY: misc_feature
<222> LOCATION: (51)..(51)
<223> OTHER INFORMATION: r is g or a

<400> SEQUENCE: 73
actaggtcgt gggatgtcgt tggggggacat gttaaatcca tggctgtcta raaggaatttt   60 ccatatcatt gagatctagg tgcacaaatt cctcgaacct a                        101

<210> SEQ ID NO 74
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is t or c

<400> SEQUENCE: 74
ggacattctt cacataaatc agaattgtcg tacacaaccc aaaattctcc aattagctaa     60
yagcgttaca gatcttcttt tccgcttctt tccacgatgt attgatatag tgtgccctga   120
a                                                                  121

<210> SEQ ID NO 75
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is t or c

<400> SEQUENCE: 75
aatgcaacaa ttctttcagc taaggagaag aaagaagcaa aagaaagaaa acactccacc    60
yctagccatt gcccatcatc catctaaatt tcttactaag atgcataata tcttccacat   120
a                                                                  121

<210> SEQ ID NO 76
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is t or c

<400> SEQUENCE: 76
ggagattgtt gcacgcctga agaaagcctt cagaattacc attaagactt cccaactctg    60
yctgcatatt gtcaagaaag ctagagattt tctcagaagc tactttaatg gcagggccct   120
c                                                                  121

<210> SEQ ID NO 77
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: w is a or t

<400> SEQUENCE: 77
gtcaaaaagg tcaagtccac actcctcagc ttatgaatca aaaccctgca cagaagggaa    60
wcacaacaac attttcaact tttcagctta acttttggca atcatcaggt taaacagact   120
t                                                                  121

<210> SEQ ID NO 78
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: k is g or t

<400> SEQUENCE: 78
ggattaattt gcaaaaacct taagtcgggg aattagggct aaagaggaat taaggtagaa    60
ktgattaccc ctgaggatta ttgaaggata aattgagttg tgattgatta gcgaaataac   120
c                                                                  121

<210> SEQ ID NO 79
<211> LENGTH: 104
<212> TYPE: DNA
<213> ORGANISM: Cucumis sativus
<220> FEATURE:
<221> NAME/KEY: misc_feature
<222> LOCATION: (44)..(44)
<223> OTHER INFORMATION: s is g or c
<220> FEATURE:
<221> NAME/KEY: misc_feature
<222> LOCATION: (101)..(101)
<223> OTHER INFORMATION: n is a, c, g, or t

<400> SEQUENCE: 79

```
ttaggttccc gctattgcaa taccaacaag gcatgaaggc tttsgccaca atgtgaaatc      60
atcaacagtt actatgaaca atgaattcgc taacaggaaa ncgt                     104
```

<210> SEQ ID NO 80
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: w is a or t

<400> SEQUENCE: 80

```
gaagtaagtt gcctgcttct cttttttca ctaggaattg ctattcagac agttatatgc      60
wcatttccaa tggtgctttt ttgttcattg ttttcaatgt tgggattgac atctgtctga    120
a                                                                    121
```

<210> SEQ ID NO 81
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: r is g or a

<400> SEQUENCE: 81

```
acgaattttc tagttgagtc aagtcaggtt ggttggaaag tgttatcaga atatgtcagt      60
rcttgtcaac tctcgcactc tcttttgagg ctataaagtt agagaagagt ctctaggaag    120
g                                                                    121
```

<210> SEQ ID NO 82
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is t or c

<400> SEQUENCE: 82

```
gagtttccaa aattgaacat cttcaatgga cagaaagttt tgaagtagca agacttaagg      60
yttccacttg gtgttcctta tctaagttct cgaacaattt gcatttgatt tcttaaatat    120
t                                                                    121
```

<210> SEQ ID NO 83
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: s is g or c

<400> SEQUENCE: 83

```
aggaaaatac cttccaatag aaaacatggt aaatgcaata agcatctagt tcatccaatt      60
scaagggtaa tggctagttc aagatggaac taaaactctc agagtggtgt gtgcaatcct    120
g                                                                    121
```

<210> SEQ ID NO 84
<211> LENGTH: 121

```
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is t or c

<400> SEQUENCE: 84
ttcatacgcc gttgcagctg aaagtggcaa ccattacttc cagatcatta tgacaataaa      60
yaaccaaggc caccttcatg cataaatggt aagataatag caagctctat accttctttt    120
t                                                                    121

<210> SEQ ID NO 85
<211> LENGTH: 107
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: s is g or c

<400> SEQUENCE: 85
actcatattt acagaaaact tactctaaac cacaagtcct taacaaatat atttctgctt      60
scggctctct tcctatcatg aaattttgca agctattcag aaaatcc                  107

<210> SEQ ID NO 86
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: w is a or t

<400> SEQUENCE: 86
gtacttgtac caatatgaaa tgtgcacatg cgctcttgtc ctagataata tgcacagttc      60
wccttaaaag ctaagcataa gccacaaatc caagaaccaa tgtaaccaaa acagtatggg    120
a                                                                    121

<210> SEQ ID NO 87
<211> LENGTH: 121
<212> TYPE: DNA
<213> ORGANISM: Cucumis sativus
<220> FEATURE:
<221> NAME/KEY: misc_feature
<222> LOCATION: (61)..(61)
<223> OTHER INFORMATION: y is t or c

<400> SEQUENCE: 87
tgaagaagag cctttattgc gtcatctgga acctccttta tccatttatc ttgaattggt      60
yggtcatgaa cacacctttta ccatttatta ttcaatgcca tgattgtctt acacaggtgt   120
g                                                                    121
```

US 8,809,622 B2

METHODS AND COMPOSITIONS FOR IDENTIFYING DOWNY MILDEW RESISTANT CUCUMBER PLANTS

BACKGROUND OF THE INVENTION

This application claims the priority of U.S. Provisional Appl. Ser. No. 61/254,141, filed Oct. 22, 2009, the entire disclosure of which is incorporated herein by reference.

INCORPORATION OF SEQUENCE LISTING

The sequence listing that is contained in the file named "SEMS108US_ST25.txt", which is 30,174 bytes (measured in MS-WINDOWS), created on Oct. 21, 2010 is filed herewith by electronic submission and is incorporated herein by reference.

FIELD OF THE INVENTION

The invention relates to methods and compositions for identifying and breeding of cucumber plants having Downy Mildew resistance.

BACKGROUND OF THE INVENTION

Cucumber (*Cucumis sativus* L.) is a popular vegetable crop that has been cultivated for several thousand years and is grown worldwide. Cucumber plants are grown in a wide range of climates, and in open fields as well as greenhouses. The two main types of cucumber fruit grown commercially today are fresh market (slicing) and processing (pickling).

Downy Mildew (DM) is caused by the fungus *Pseudoperonospora cubensis* (P.c.), which causes significant crop losses among many Cucurbit species, including cucumber. The disease is found worldwide and favors moist, temperate conditions. The disease affects greenhouse grown plants, and plants grown in the field. DM is one of the most important foliar diseases of cucurbits, and can reduce fruit yield and quality, and may kill susceptible seedlings.

Symptoms of DM infection are variable. Initial symptoms include sharp, irregular yellow lesions on the upper surface of the leaves, which eventually become more distinct on both sides of the leaves. The underside of the leaves may exhibit a whitish-gray, brown, or light blue growth, particularly under moist conditions. This downy growth is spores produced on the lower surface of the lesion. A general yellowing of affected leaves typically occurs as the lesions coalesce into one large lesion, eventually causing the leaf to wilt and die. The disease can progress quite rapidly, killing foliage in a matter of a few days and resulting in poor fruit production and quality. Cucumber fruit are not affected directly, but major defoliation exposes the fruit to sunscald. Once it appears on a crop, DM rapidly spreads by wind, or splashing rain and/or irrigation water. Disease management and prevention requires destruction of all plants from infected nurseries and disinfection of the facilities. Emergence of a new isolate of DM has also overcome some previously known resistant lines. Thus, there is a need for new cucumber varieties having resistance to DM, and methods for producing such plants.

SUMMARY OF THE INVENTION

In a first aspect, the invention provides a method of obtaining cucumber germplasm comprising the steps of: a) assaying cucumber plants for the presence of at least a first genetic marker genetically linked to a QTL that confers resistance to Downy Mildew; and b) selecting at least a first cucumber plant comprising the genetic marker and the QTL that confers resistance to Downy Mildew; wherein the QTL maps to a position between the sequence represented by SNP marker NN0228457 and SNP marker NN0228148, which map to approximately 25.2 cM and 82.7 cM on the genetic map of the linkage group termed cucumber chromosome 5; wherein the QTL maps to a position between the sequence represented by SNP marker NN0225012 and SNP marker NN0227587 which map to approximately 20.6 cM and 87.4 cM on the genetic map of the linkage group termed cucumber chromosome 4; or wherein the QTL maps to a position between the sequence represented by SNP marker NN0223782 and SNP marker NN0226638 which map to approximately 22.5 cM and 88.4 cM on the genetic map of the linkage group termed cucumber chromosome 2. In particular embodiments, the QTL allele which confers resistance to Downy Mildew is derived from cucumber line PI197088, or a progeny plant thereof.

In certain embodiments, the QTL maps to a position between the sequence represented by SNP marker NN0227981 and SNP marker NN0226631, which map to approximately 35.7 cM and 55.5 cM on the genetic map of the linkage group termed cucumber chromosome 5; or wherein the QTL maps to a position between the sequence represented by SNP marker NN0227981 and SNP marker NN0247786, which map to approximately 35.7 cM and 71.4 cM on the genetic map of the linkage group termed cucumber chromosome 5. In other embodiments, the QTL maps to a position between the sequence represented by SNP marker NN0228579 and SNP marker NN0224495 which map to approximately 25.8 cM and 82.0 cM on the genetic map of the linkage group termed cucumber chromosome 4; wherein the QTL maps to a position between the sequence represented by SNP marker NN0225088 and SNP marker NN0224041 which map to approximately 30.4 cM and 75.8 cM on the genetic map of the linkage group termed cucumber chromosome 4; or wherein the QTL maps to a position between the sequence represented by SNP marker NN0228579 and SNP marker NN0224495 which map to approximately 54.5 cM and 82.0 cM on the genetic map of the linkage group termed cucumber chromosome 4. In yet another embodiment, the QTL maps to a position between the sequence represented by SNP marker NN0246378 and SNP marker NN0246472 which map to approximately 14.6 cM and 38.4 cM on the genetic map of the linkage group termed cucumber chromosome 2.

In certain embodiments, the invention also provides such a method, wherein selecting the first cucumber plant further comprises selecting the plant based on the presence of a plurality of genetic markers that map to a position between the sequence represented by SNP marker NN0228457 and SNP marker NN0228148, which map to approximately 25.2 cM and 82.7 cM on the genetic map of the linkage group termed cucumber chromosome 5; or wherein the QTL maps to a position between the sequence represented by SNP marker NN0227981 and SNP marker NN0226631, which map to approximately 35.7 cM and 55.5 cM on the genetic map of the linkage group termed cucumber chromosome 5; or wherein the QTL maps to a position between the sequence represented by SNP marker NN0227981 and SNP marker NN0247786, which map to approximately 35.7 cM and 71.4 cM on the genetic map of the linkage group termed cucumber chromosome 5; or wherein the QTL maps to a position between the sequence represented by SNP marker NN0225012 and SNP marker NN0227587 which map to approximately 20.6 cM and 87.4 cM on the genetic map of the linkage group termed cucumber chromosome 4; or wherein the QTL maps to a position between the sequence represented by SNP marker NN0247342 and SNP marker NN0224495 which map to approximately 54.5 cM and 82.0 cM on the genetic map of the linkage group termed cucumber chromosome 4; or wherein the QTL maps to a position between the sequence represented by SNP marker NN0223782 and SNP marker NN0226638 which map to approximately 22.5 cM and 88.4 cM on the genetic map of the linkage group termed cucumber chromosome 2.

In certain embodiments, the genetic marker is selected from the group consisting of markers NN0223782, NN0225385, NN0226670, NN0224124, NN0246472, NN0225358, NN0227700, NN0224617, NN0247695, NN0227242, NN0223824, NN0223181, NN0226638, NN0225012, NN0228579, NN0226451, NN0225088, NN0226219, NN0247551, NN0246357, NN0225551, NN0226732, NN0247689, NN0247342, NN0224702, NN0225482, NN0224538, NN0247543, NN0224041, NN0228853, NN0227762, NN0227587, NN0228457, NN0246356, NN0246332, NN0223399, NN0223689, NN0247731, NN0226166, NN0225480, NN0246411, NN0227759, NN0247348, NN0228465, NN0247786, NN0226645, NN0223809, NN0227071, NN0226870, NN0228148, NN0246378, NN0224041, NN0227587, NN5096749, NN0224856, NN0223160, NN0223809, NN0226631, NN0227981, NN0247786, NN0246425, NN0224495, NN0225088, NN0227071, NN0223782, NN0228579, NN0247342, and NN0247731, comprising a single nucleotide polymorphism of one of SEQ ID NOs:20-87. In particular embodiments the genetic marker is selected from the group consisting of markers NN0223782, NN0225385, NN0226670, NN0224124, NN0246472, NN0225358, NN0227700, NN0224617, NN0247695, NN0227242, NN0223824, NN0223181, NN0226638, and NN0246378. In yet other embodiments, the genetic marker is selected from the group consisting of markers NN0225012, NN0228579, NN0226451, NN0225088, NN0226219, NN0247551, NN0246357, NN0225551, NN0226732, NN0247689, NN0247342, NN0224702, NN0225482, NN0224538, NN0247543, NN0224041, NN0228853, NN0227762, NN0227587, NN0224041, NN0227587, NN0246425, NN0224495, NN0225088, NN0228579, and NN0247342. In still yet other embodiments, the genetic marker is selected from the group consisting of markers NN0228457, NN0246356, NN0246332, NN0223399, NN0223689, NN0247731, NN0226166, NN0225480, NN0246411, NN0227759, NN0247348, NN0228465, NN0247786, NN0226645, NN0223809, NN0227071, NN0226870, NN0228148, NN5096749, NN0224856, NN0223160, NN0223809, NN0226631, NN0227981, NN0247786, NN0227071, and NN0247731. In particular embodiments, the genetic marker is NN0226631 or NN0246425. Further, in such embodiments assaying the cucumber plants comprises PCR, single strand conformational polymorphism analysis, denaturing gradient gel electrophoresis, cleavage fragment length polymorphism analysis, TAQMAN assay, and/or DNA sequencing.

Further, in certain embodiments the genetic marker may map within 20 cM, 10 cM or 1 cM of a QTL which confers resistance to Downy Mildew In another aspect, the invention provides a method of cucumber plant breeding comprising: a) assaying cucumber plants for the presence of at least a first genetic marker genetically linked to a QTL that confers resistance to Downy Mildew; and b) selecting at least a first cucumber plant comprising the genetic marker and the QTL that confers resistance to Downy Mildew; wherein the QTL maps to a position between the sequence represented by SNP marker NN0228457 and SNP marker NN0228148, which map to approximately 25.2 cM and 82.7 cM on the genetic map of the linkage group termed cucumber chromosome 5; wherein the QTL maps to a position between the sequence represented by SNP marker NN0227981 and SNP marker NN0226631, which map to approximately 35.7 cM and 55.5 cM on the genetic map of the linkage group termed cucumber chromosome 5; wherein the QTL maps to a position between the sequence represented by SNP marker NN0227981 and SNP marker NN0247786, which map to approximately 35.7 cM and 71.4 cM on the genetic map of the linkage group termed cucumber chromosome 5; wherein the QTL maps to a position between the sequence represented by SNP marker NN0225012 and SNP marker NN0227587 which map to approximately 20.6 cM and 87.4 cM on the genetic map of the linkage group termed cucumber chromosome 4; wherein the QTL maps to a position between the sequence represented by SNP marker NN0247342 and SNP marker NN0224495 which map to approximately 54.5 cM and 82.0 cM on the genetic map of the linkage group termed cucumber chromosome 4; or wherein the QTL maps to a position between the sequence represented by SNP marker NN0223782 and SNP marker NN0226638 which map to approximately 22.5 cM and 88.4 cM on the genetic map of the linkage group termed cucumber chromosome 2; and c) crossing the first cucumber plant with itself or a second cucumber plant to produce progeny cucumber plants comprising the QTL that confers resistance to Downy Mildew.

In one embodiment of the method, selecting at least a first cucumber plant further comprises selecting the plant based on the presence of a plurality of genetic markers that map to a position between the sequence represented by SNP marker NN0228457 and SNP marker NN0228148, which map to approximately 25.2 cM and 82.7 cM on the genetic map of the linkage group termed cucumber chromosome 5; wherein the QTL maps to a position between the sequence represented by SNP marker NN0227981 and SNP marker NN0226631, which map to approximately 35.7 cM and 55.5 cM on the genetic map of the linkage group termed cucumber chromosome 5; wherein the QTL maps to a position between the sequence represented by SNP marker NN0227981 and SNP marker NN0247786, which map to approximately 35.7 cM and 71.4 cM on the genetic map of the linkage group termed cucumber chromosome 5; wherein the QTL maps to a position between the sequence represented by SNP marker NN0225012 and SNP marker NN0227587 which map to approximately 20.6 cM and 87.4 cM on the genetic map of the linkage group termed cucumber chromosome 4; wherein the QTL maps to a position between the sequence represented by SNP marker NN0247342 and SNP marker NN0224495 which map to approximately 54.5 cM and 82.0 cM on the genetic map of the linkage group termed cucumber chromosome 4; or wherein the QTL maps to a position between the sequence represented by SNP marker NN0223782 and SNP marker NN0226638 which map to approximately 22.5 cM and 88.4 cM on the genetic map of the linkage group termed cucumber chromosome 2. In another embodiment of the method, it may further comprise the step of: d) selecting a progeny plant comprising the allele which confers resistance to Downy Mildew and crossing the progeny plant with itself or a third cucumber plant to produce additional progeny plants. In certain embodiments, the method further comprises repeating step (d) about 2-10 times. Likewise, in certain embodiments the allele which confers resistance to Downy Mildew is derived from cucumber line PI197088, or a progeny plant thereof.

In certain embodiments, the genetic marker maps within 20 cM, 10 cM or 1 cM of a QTL which confers resistance to Downy Mildew. In some embodiments the genetic marker is selected from the group consisting of markers NN0223782, NN0225385, NN0226670, NN0224124, NN0246472, NN0225358, NN0227700, NN0224617, NN0247695, NN0227242, NN0223824, NN0223181, NN0226638, NN0225012, NN0228579, NN0226451, NN0225088, NN0226219, NN0247551, NN0246357, NN0225551, NN0226732, NN0247689, NN0247342, NN0224702, NN0225482, NN0224538, NN0247543, NN0224041, NN0228853, NN0227762, NN0227587, NN0228457, NN0246356, NN0246332, NN0223399, NN0223689, NN0247731, NN0226166, NN0225480, NN0246411, NN0227759, NN0247348, NN0228465, NN0247786, NN0226645, NN0223809, NN0227071, NN0226870, NN0228148, NN0246378, NN0224041, NN0227587, NN5096749, NN0224856, NN0223160, NN0223809, NN0226631, NN0227981, NN0247786, NN0246425, NN0224495, NN0225088, NN0227071, NN0223782, NN0228579, NN0247342, and NN0247731, comprising a single nucleotide polymorphism of one of SEQ ID NOs:20-87. In particular embodiments of the method, the genetic marker is selected from the group consisting of markers NN0223782, NN0225385, NN0226670, NN0224124, NN0246472, NN0225358, NN0227700, NN0224617, NN0247695, NN0227242, NN0223824, NN0223181, NN0226638, and NN0246378. In other embodiments the genetic marker is selected from the group consisting of markers NN0225012, NN0228579, NN0226451, NN0225088, NN0226219, NN0247551, NN0246357, NN0225551, NN0226732, NN0247689, NN0247342, NN0224702, NN0225482, NN0224538, NN0247543, NN0224041, NN0228853, NN0227762, NN0227587, NN0224041, NN0227587, NN0246425, NN0224495, NN0225088, NN0228579, and NN0247342. In yet other embodiments, the genetic marker is selected from the group consisting of markers NN0228457, NN0246356, NN0246332, NN0223399, NN0223689, NN0247731, NN0226166, NN0225480, NN0246411, NN0227759, NN0247348, NN0228465, NN0247786, NN0226645, NN0223809, NN0227071, NN0226870, NN0228148, NN5096749, NN0224856, NN0223160, NN0223809, NN0226631, NN0227981, NN0247786, NN0227071, and NN0247731. In particular embodiments, the genetic marker is NN0226631 or NN0246425. In such embodiments, assaying the cucumber plants may comprise PCR, single strand conformational polymorphism analysis, denaturing gradient gel electrophoresis, cleavage fragment length polymorphism analysis, TAQMAN assay, and/or DNA sequencing.

In some embodiments the cucumber plant comprising at least one allele which confers resistance to Downy Mildew demonstrates a reduction of foliar symptoms of chlorotic and/or necrotic lesions of at least, or greater than, 25%, relative to a non-resistant control cucumber line.

In another aspect, the invention provides an isolated nucleic acid probe or primer that hybridizes under conditions of 5×SSC, 50% formamide, and 42° C. to a cucumber plant genomic region mapping within 40 cM of a QTL which confers resistance to Downy Mildew and comprises a sequence which maps on cucumber chromosomes 2, 4, or 5, wherein the probe or primer comprises a nucleic acid sequence selected from the group consisting of SEQ ID NOs: 20-87.

In another aspect, a cucumber plant is provided which is produced by the method of: a) assaying cucumber plants for the presence of at least a first genetic marker genetically linked to a QTL that confers resistance to Downy Mildew; and b) selecting at least a first cucumber plant comprising the genetic marker and the QTL that confers resistance to Downy Mildew; wherein the QTL maps to a position between the sequence represented by SNP marker NN0228457 and SNP marker NN0228148, which map to approximately 25.2 cM and 82.7 cM on the genetic map of the linkage group termed cucumber chromosome 5; wherein the QTL maps to a position between the sequence represented by SNP marker NN0227981 and SNP marker NN0226631, which map to approximately 35.7 cM and 55.5 cM on the genetic map of the linkage group termed cucumber chromosome 5; wherein the QTL maps to a position between the sequence represented by SNP marker NN0227981 and SNP marker NN0247786, which map to approximately 35.7 cM and 71.4 cM on the genetic map of the linkage group termed cucumber chromosome 5; wherein the QTL maps to a position between the sequence represented by SNP marker NN0225012 and SNP marker NN0227587 which map to approximately 20.6 cM and 87.4 cM on the genetic map of the linkage group termed cucumber chromosome 4; wherein the QTL maps to a position between the sequence represented by SNP marker NN0247342 and SNP marker NN0224495 which map to approximately 54.5 cM and 82.0 cM on the genetic map of the linkage group termed cucumber chromosome 4; or wherein the QTL maps to a position between the sequence represented by SNP marker NN0223782 and SNP marker NN0226638 which map to approximately 22.5 cM and 88.4 cM on the genetic map of the linkage group termed cucumber chromosome 2; and c) crossing the first cucumber plant with itself or a second cucumber plant to produce progeny cucumber plants comprising the QTL that confers resistance to Downy Mildew. Further provided is a progeny plant thereof that comprises said genetic marker and QTL that confers resistance to Downy Mildew. The invention also provides, in further embodiments, such a cucumber plant comprising two introgressed cucumber chromosomal regions conferring resistance to *Pseudoperonospora cubensis*, wherein the regions comprise a Downy Mildew resistance contributing QTL region found on chromosome 4, and a Downy Mildew resistance contributing QTL region found on chromosome 5. In particular embodiments the cucumber plant is homozygous for said chromosomal region or regions.

In certain embodiments the cucumber plant, or progeny plant thereof, is further defined as an agronomically elite plant. Also provided in certain embodiments is a part of such a cucumber plant or progeny thereof, further defined as pollen, an ovule, a leaf, an embryo, a root, a root tip, an anther, a flower, a fruit, a stem, a shoot, a seed, a protoplast, a cell, and a callus. Another embodiment provides a seed that produced such a plant.

Certain embodiments provide a cucumber plant comprising at least a first introgressed cucumber chromosomal region conferring resistance to *Pseudoperonospora cubensis*, wherein the region is selected from the group consisting of: a Downy Mildew resistance contributing QTL region found on chromosome 2, a Downy Mildew resistance contributing QTL region found on chromosome 4, and a Downy Mildew resistance contributing QTL region found on chromosome 5; further wherein the QTL maps to a position between the sequence represented by SNP marker NN0228457 and SNP marker NN0228148, which map to approximately 25.2 cM and 82.7 cM on the genetic map of the linkage group termed cucumber chromosome 5; wherein the QTL maps to a position between the sequence represented by SNP marker NN0225012 and SNP marker NN0227587 which map to approximately 20.6 cM and 87.4 cM on the genetic map of the linkage group termed cucumber chromosome 4; or wherein the QTL maps to a position between the sequence represented by SNP marker NN0246378 and SNP marker NN0247695 which map to approximately 14.6 cM and 66.5 cM on the genetic map of the linkage group termed cucumber chromosome 2. Particular embodiments provide a cucumber plant, wherein the QTL maps to a position between the sequence represented by SNP marker NN0227981 and SNP marker NN0226631, which map to approximately 35.7 cM and 55.5 cM on the genetic map of the linkage group termed cucumber chromosome 5; or wherein the QTL maps to a position between the sequence represented by SNP marker NN0227981 and SNP marker NN0247786, which map to approximately 35.7 cM and 71.4 cM on the genetic map of the linkage group termed cucumber chromosome 5. In further embodiments, the invention provides a cucumber plant comprising at least two introgressed cucumber chromosomal regions selected from said group.

In some embodiments the QTL of the cucumber plant maps to a position between the sequence represented by SNP marker NN0228579 and SNP marker NN0224495 which map to approximately 25.8 cM and 82.0 cM on the genetic map of the linkage group termed cucumber chromosome 4; wherein the QTL maps to a position between the sequence represented by SNP marker NN0225088 and SNP marker NN0224041 which map to approximately 30.4 cM and 75.8 cM on the genetic map of the linkage group termed cucumber chromosome 4; or wherein the QTL maps to a position between the sequence represented by SNP marker NN0228579 and SNP marker NN0224495 which map to approximately 54.5 cM and 82.0 cM on the genetic map of the linkage group termed cucumber chromosome 4. In other embodiments the QTL maps to a position between the sequence represented by SNP marker NN0246378 and SNP marker NN0246472 which map to approximately 14.6 cM and 38.4 cM on the genetic map of the linkage group termed cucumber chromosome 2.

Also provided is a cucumber plant wherein the first introgressed cucumber chromosomal region conferring resistance to *Pseudoperonospora cubensis* comprises an allele present in PI197088. In certain embodiments, the cucumber plant comprises a QTL region found on chromosome 2, wherein the QTL maps to a position between the sequence represented by SNP marker NN0246378 and SNP marker NN0247695 which map to approximately 14.6 cM and 66.5 cM on the genetic map of the linkage group termed cucumber chromosome 2, and wherein the QTL is introgressed from PI197088. The cucumber plant may further be defined as comprising an allele from PI197088 at one or more of markers NN0246378, NN0223782, NN0246472, and NN0247695. In particular embodiments the cucumber plant is further defined as comprising at least a first allele not present in PI197088, wherein the allele is detected with the group of markers comprising NN0247695, NN0246472, NN0223782, and NN0246378.

In other embodiments of the invention, the cucumber plant comprises the Downy Mildew resistance contributing QTL region found on chromosome 4 wherein the QTL maps to a position between the sequence represented by SNP marker NN0225012 and SNP marker NN0227587 which map to approximately 20.6 cM and 87.4 cM on the genetic map of the linkage group termed cucumber chromosome 4. In certain embodiments the DM resistance QTL is introgressed from PI197088. In particular embodiments the cucumber plant may further be defined as comprising: a) an allele from PI197088 at one or more of markers selected from the group consisting of: NN0228579, NN0225088, NN0225551, NN0247342, NN0246425, NN0224041, NN0224495, and NN0227587; b) an allele which is not present in PI197088 of at least one marker selected from the group consisting of: NN0228579, NN0225088, NN0225551, NN0247342, NN0246425, NN0224041, NN0224495, and NN0227587; c) an allele from PI197088 at marker NN0246425, an allele not present in PI197088 at marker NN0247342 and an allele not present in PI197088 at marker NN0224495; d) an allele from PI197088 at marker NN0246425, an allele not present in PI197088 at marker NN0225088 and an allele not present in PI197088 at marker NN0224495; or e) an allele from PI197088 at marker NN0246425, an allele not present in PI197088 at marker NN0228579, and an allele not present in PI197088 at marker NN0224495.

In other embodiments, the cucumber plant of claim 36, comprising the QTL region found on chromosome 5, wherein the QTL maps to a position between the sequence represented by SNP marker NN0228457 and SNP marker NN0228148, which map to approximately 25.2 cM and 82.7 cM on the genetic map of the linkage group termed cucumber chromosome 5. In certain embodiments the QTL region is introgressed from PI197088. In particula embodiments the cucumber plant may further be defined as comprising: a) an allele from PI197088 at one or more of markers selected from the group consisting of: NN5096749, NN0224856, NN0227981, NN0247731, NN0226631, NN0247786, NN0223160, NN0223809, NN0227071, and NN0228148; b) an allele which is not present in PI197088 of at least one marker selected from the group consisting of: NN0228148, NN0227071, NN0223809, NN0223160, NN0247786, NN0226631, NN0247731, NN0227981, NN0224856, and NN5096749; c) an allele from PI197088 at marker NN0226631, an allele not present in PI197088 at marker NN0227981, and an allele not present in PI197088 at marker NN0247786; d) an allele from PI197088 at marker NN0226631, an allele not present in PI197088 at marker NN0227981, and an allele not present in PI197088 at marker NN0227071; or e) an allele from PI197088 at marker NN0226631, an allele not present in PI197088 at marker NN0224856, and an allele not present in PI197088 at marker NN0227071.

DETAILED DESCRIPTION OF THE INVENTION

Figure 1:
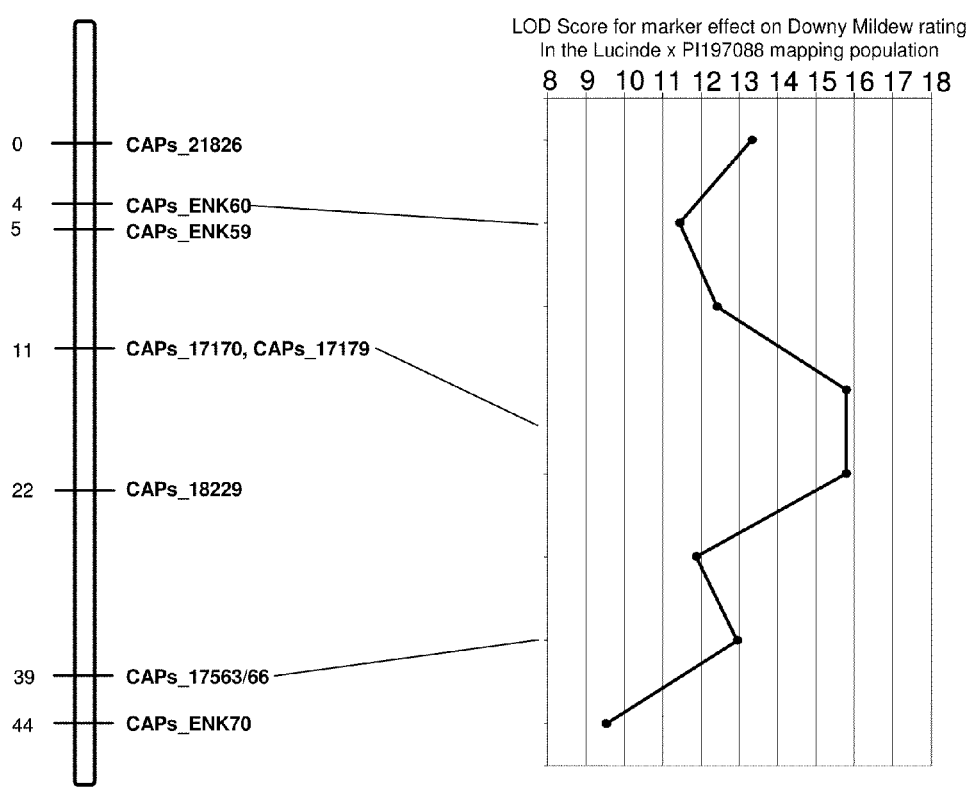
FIG. 1 depicts a genetic map (left) and LOD plot (right) for marker effects on Downy Mildew reaction in 148 F3 families from the cucumber L088 (Lucindex×PI197088) population. Lines between the genetic map and LOD plot provide reference positions for three of the markers to aid in comparisons of map position and LOD score. This linkage group corresponds to chromosome 5 as described for instance in Ren et al., 2009 (*PLoS ONE* 4:e5795, 2009; doi:10.1371/journal.pone.0005795). Other exemplary genetic maps of cucumber are provided for instance in Staub, et al., 2007 (*HortScience*, 40:20-27), and Meboah et al., 2007 (*Afr. J. Biotechnol.* 6:2784-2791).

The invention provides methods for identifying cucumber plants (*Cucumis sativus*) having resistance to Downy Mildew (DM) caused by *Pseudoperonospora cubensis*. Such cucumber lines can be referred to as DM resistant cucumber varieties. Methods of breeding DM resistant cucumber lines are further provided. Also disclosed herein are molecular markers that are linked to quantitative trait loci contributing to DM resistance. Through use of the markers, one of skill in the art may increase the degree of DM resistance in cucumber or select plants for an increased predisposition for DM resistance. In particular embodiments, the methods are performed on progeny cucumber plants of cucumber line PI197088, such as members of the API, VJ, or QIR mapping populations disclosed herein, or progeny thereof. The QTLs identified in this manner may be combined with one or more other QTLs that also contribute to DM resistance, as desired. In addition to the QTL identified in FIG. 1 which corresponds to "QTL 1" (localized to chromosome 5:25.3-82.1 cM as identified in FIGS. 5A-5B and Table 19; or chromosome 5:25.2-78.3 cM, or chromosome 5:28.5-75.0 cM), another major QTL (termed "QTL 2") was identified in the API, VJ, or QIR mapping populations, at chromosome 4::20.6-87.4 cM (see FIGS. 5C-5D and Table 19; or chromosome 4:25.8-82.0 cM; or chromosome 4:31.8-75.8 cM), also having significant effect on Downy Mildew resistance in cucumber. Individually, each allele of these two QTLs is estimated to have the potential to significantly reduce a plant's Downy Mildew disease rating in a DM pathology test as described herein, for instance in both the API and VJ mapping population genetic backgrounds, when grown in multiple tested geographic locations. An additional QTL ("QTL 4"; see FIGS. 5E-5F) mapping to chromosome 2: 22.3-88.4 cM also has an effect in cucumber Downy Mildew resistance, although its genetic effect is apparently more complex, with potential interactions with other QTLs and/or the growth environment.

The average individual additive allelic effects are estimated at 0.62 (0.32-1.26) at QTL 1 and 0.62 (0.47-0.93) at QTL 2, from the studies described in Example 8. Allelic effects of about 0.7 disease score units at each of QTL1 and QTL2 of chromosomes 4 and 5 were observed in the QIR mapping population. Therefore, an individual plant with both resistant alleles at both QTLs is likely to have a reduction in disease rating of 0.62×2+0.62×2=2.48. Individually, the average amount of phenotypic variation explained by each of these two QTLs is 24% (QTL 1) and 21% (QTL 2), with the remaining 76%-79% attributable to other genetic effects and environmental (non-genetic) effects.

The definition of these QTLs allows the use of specific molecular markers, such as those disclosed herein, in a plant breeding program to introgress a Downy Mildew Resistance trait or traits to agronomically acceptable cucumber lines. Marker-assisted introgression involves the transfer of a chromosomal region, defined by one or more markers, from one germplasm to a second germplasm. An initial step in that process is the localization of the trait by gene mapping which is the process of determining the position of a gene relative to other genes and genetic markers through linkage analysis. The basic principle for linkage mapping is that the closer together two genes are on the chromosome, the more likely they are to be inherited together. Briefly, a cross is made between two genetically compatible but divergent parents relative to a trait under study (e.g. DM resistance). Genetic markers are then used to follow the segregation of traits under study in the progeny from the cross, often termed a "mapping population." The current invention relates to the introgression in cucumber of genetic material, e.g., mapping to one or more QTLs, which is capable of causing a plant to be more resistant to the pathogen which causes cucumber Downy mildew disease. The present inventors have identified chromosomal regions responsible for enhanced DM resistance and used marker assisted breeding to introgress these specific linkage blocks into other cucumber germplasm which lacked such resistance to DM. In certain embodiments of the invention, the process for producing DM resistant cucumber plant or line comprises introgressing at least one chromosomal locus mapping to QTL 1, QTL 2, and/or QTL 4 from a more DM resistant cucumber plant, line, or variety into a less DM resistant cucumber plant, line, or variety. In specific embodiments, the more DM resistant cucumber plant, line, or variety is PI197088, or a progeny plant thereof.

Introgression of a particular DNA element or set of elements into a plant genotype is defined as the result of the process of backcross conversion. A plant genotype into which a DNA sequence has been introgressed may be referred to as a backcross converted genotype, line, or variety. Such genotype, line, or variety may be an inbred or a hybrid genotype, line, or variety. Similarly a plant genotype lacking said desired DNA sequence may be referred to as an unconverted genotype, line, or variety. During breeding, the genetic markers linked to enhanced DM resistance may be used to assist in breeding for the purpose of producing cucumber plants with increased resistance to *Pseudoperonospora cubensis*. A skilled worker would understand that the introgression of a DM resistance trait into a cucumber plant may be monitored by visual clues such as by use of a disease resistance test with a disease rating scale as described herein, and/or by monitoring and breeding for the presence of molecular markers as described herein (i.e. marker assisted selection).

Localization of such markers to specific genomic regions or contigs further allows for use of associated sequences in breeding, to develop additional linked genetic markers, as well as to identify the mechanism for resistance at more precise genetic and biochemical levels. It will be understood to those of skill in the art that other markers or probes which more closely map the chromosomal regions as identified herein could be employed to identify plants comprising a desired QTL for DM resistance. The chromosomal regions of the present invention facilitate introgression of increased DM resistance from DM resistant germplasm, such as PI197088 or progeny thereof, into other germplasm, preferably agronomically useful cucumber germplasm. Linkage blocks of various sizes could be transferred within the scope of this invention as long as the chromosomal region enhances the DM resistance of a desirable cucumber plant, line, or variety. Accordingly, it is emphasized that the present invention may be practiced using any molecular markers which genetically map in similar regions, provided that the markers are polymorphic between the parents.

In particular embodiments, these markers may be genetically linked to the described QTLs for DM resistance which are located on cucumber chromosomes 2, 4, or 5, for instance as defined in the genetic map of Ren et al. (*PLoS ONE* 4:e5795, 2009; doi:10.1371/journal.pone.0005795). In certain embodiments, the markers are within 50 cM, 45 cM, 40 cM, 30 cM, 20 cM, 10 cM, 5 cM, 3 cM, 1 cM, or less, of QTL 1 defined on chromosome 5, at 22.6-81.0 cM; or QTL 2 defined on chromosome 4 at 37.7-87.6 cM; or QTL 4 defined on chromosome 2 at 21.8-73.8 cM, based on analysis of the API and VJ mapping populations as described herein. In particular embodiments, the markers used to follow the presence of any of these QTLs for DM resistance which are located on cucumber chromosomes 5, 4, or 2, are selected from the group consisting of: NN0223782, NN0225385, NN0226670, NN0224124, NN0246472, NN0225358, NN0227700, NN0224617, NN0247695, NN0227242, NN0223824, NN0223181, NN0226638, NN0225012, NN0228579, NN0226451, NN0225088, NN0226219, NN0247551, NN0246357, NN0225551, NN0226732, NN0247689, NN0247342, NN0224702, NN0225482, NN0224538, NN0247543, NN0224041, NN0228853, NN0227762, NN0227587, NN0228457, NN0246356, NN0246332, NN0223399, NN0223689, NN0247731, NN0226166, NN0225480, NN0246411, NN0227759, NN0247348, NN0228465, NN0247786, NN0226645, NN0223809, NN0227071, NN0226870, NN0228148, NN0246378, NN0224041, NN0227587, NN5096749, NN0224856, NN0223160, NN0223809, NN0226631, NN0227981, NN0247786, NN0246425, NN0224495, NN0225088, NN0227071, NN0223782, NN0228579, NN0247342, and NN0247731, comprising a single nucleotide polymorphism of one of SEQ ID NOs:20-87 as shown in Tables 13 and 22, and UBC12-1200, and CAPs_ENK59, or other genetic markers linked to any of these QTLs. The presence of alleles conferring resistance to DM may be identified by use of well known techniques, such as by nucleic acid detection methods utilizing probes or primers comprising a sequence selected from the group consisting of SEQ ID NO:1-87. In certain embodiments, the method comprises detecting the presence of one or more single nucleotide polymorphisms (SNP's) given in one or more of SEQ ID NOs: 20-87.

In certain embodiments, the DM resistance QTL of chromosome 2 is defined as spanning the region defined by SNP marker NN0223782 (map position 22.5 according to Table 19), to SNP marker NN0226638 (map position 88.4). In other embodiments, the DM resistance QTL of chromosome 2 is defined as spanning the region defined by SNP marker NN0246378 (map position ~14.6 according to Tables 19 or 22), to SNP marker NN0246472 (map position 38.4 according to Table 19).

In certain embodiments, the DM resistance QTL of chromosome 4 is defined as spanning the region defined by SNP marker NN0225012 (map position 20.6), to SNP marker NN0227587 (map position 87.4). In other embodiments, the DM resistance QTL of chromosme 4 is defined as spanning the region defined by SNP marker NN225088 (map position 30.4) to SNP marker NN0224041 (map position 75.8). In other embodiments, the DM resistance QTL of chromosome 4 is defined as spanning the region defined by SNP marker NN0228579 (map position 25.8), to SNP marker NN0224495 (map position 82.0).

In certain embodiments, the DM resistance QTL of chromosome 5 is defined as spanning the region defined by SNP marker NN0228457 (map position 25.2), to SNP marker NN0228148 (map position 82.7), as listed in Tables 13 and 19. In other embodiments, the DM resistance QTL of chromosome 5 is defined as spanning the region defined by SNP marker NN0224856 (map position 28.5) to SNP marker NN0223160 (map position 75.0). In yet other embodiments, the DM resistance QTL of chromosome 5 is defined as spanning the region defined by SNP marker NN5096749 (map position 25.2), to SNP marker NN0227071 (map position 78.3).

QTL 1 has also been defined in a mapping population based on a cross of cucumber lines Lucinde and PI197088, as being located between genetic markers ENK59 and CAPs_17563/66, at about 5 cM-39 cM in the linkage group, and as defined by analysis of that mapping population (e.g. see FIG. 1). Further, one of skill in the art would understand that assignment of such genetic map positions may be affected by the mapping population being analyzed, including for instance the parent lines used, the marker density, and the size of the population, each of which may affect the level of recombination which is seen, and thus the assigned genetic map position. An integrated genetic and physical map may be utilized to define the position of a cucumber QTL, such as one provided by Ren et al, 2009, for instance relative to markers with known genetic and/or physical map positions.

The DM resistant cucumber plants of the present invention may bear one or more alleles conferring DM resistance that have been introduced into the cucumbers from a line designated PI197088 comprising the DM resistance, but otherwise comprising poor agronomic characteristics. The resulting DM resistant cucumber plants of the present invention surprisingly display elite agronomic traits in combination with DM resistance, while lacking deleterious traits.

DM resistant cucumber plants may have large leaves that form a canopy over the fruit. The vine is typically indeterminate and grown on trellises or the ground. DM resistant cucumber plants may have dark green, green, light green to yellow, and occasionally yellow to brown leaves. The leaves of the DM resistant cucumber plants vary in size, but typically are from about 200-250 mm in length and 150-200 mm in width, and are usually simple, alternate, palmate, and lobed.

The ripe fruit of DM resistant cucumber plants of the present invention can vary from light to medium green, or even dark green, and typically the color on an individual fruit varies from a lighter-colored blossom end to a darker colored stem-end. The color may be mottled with yellow speckles. The fruit of DM resistant cucumber is typically elongated and cylindrical with rounded or blunt ends, but may also be straight or curved, and is usually 25-30 cm in length at harvest maturity, although the fruit may be edible at 11-14 cm. The skin of the fruit is typically smooth, dull and thick; the skin may be tough or tender with a varied number of tubercules. The flesh of the fruit is usually cream colored, with or without stripes, and has a bitter-free taste.

As used herein, a "susceptible control cucumber plant" refers to a cucumber plant susceptible to Downy Mildew (DM susceptible) including commercially available and wild relatives of modern cucumber plants. In one aspect, the control cucumber plant is the variety MARAM, SMR58, CORONA, or SPRINT 440. A "resistant control cucumber plant" may also be utilized when evaluating DM resistant cucumber varieties. In one embodiment, such a control is a cucumber plant that is not susceptible to DM, but is otherwise agriculturally undesirable, for example, variety PI197088. Similarly, some controls may have intermediate resistance, for example, controls with intermediate resistance to DM may be DMP21, GP14, LLP-1, ADEFEM, SWEETSLICE, or POINSETT 76. As described herein, a control cucumber line is grown under similar environmental conditions as the comparative cucumber line, according to the present disclosure.

As used herein, a "hybrid cucumber plant" includes a plant resulting directly or indirectly from crosses between populations, breeds or cultivars within the species *Cucumis sativus*. "Hybrid cucumber plant" as used herein also refers to plants resulting directly or indirectly from crosses between different varieties or genotypes.

As used herein, a "female parent" refers to a cucumber plant that is the recipient of pollen from a male donor line, which pollen successfully pollinates an egg. A female parent can be any cucumber plant that is the recipient of pollen. Such female parents can be male sterile, for example, because of genic male sterility, cytoplasmic male sterility, or because they have been subject to manual emasculation of the stamens. Genic or cytoplasmic male sterility can be manifested in different manners, such as sterile pollen, malformed or stamenless flowers, positional sterility, and functional sterility.

As used herein, "cytoplasmic male sterility" refers to plants that are not usually capable of breeding from self-pollination, but are capable of breeding from cross-pollination.

As used herein, "linkage" is a phenomenon wherein alleles on the same chromosome tend to segregate together more often than expected by chance if their transmission was independent.

As used herein, a "marker" is an indicator for the presence of at least one phenotype, genotype, or polymorphism. Markers include, but are not limited to, single nucleotide polymorphisms (SNPs), cleavable amplified polymorphic sequences (CAPS), amplified fragment length polymorphisms (AFLPs), restriction fragment length polymorphisms (RFLPs), simple sequence repeats (SSRs), insertion(s)/deletion(s) ("INDEL"(s)), inter-simple sequence repeats (ISSR), and random amplified polymorphic DNA (RAPD) sequences. A marker is preferably inherited in codominant fashion (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism, phenotype, or both associated with DM resistance. Stringent conditions for hybridization of a nucleic acid probe or primer to a marker sequence or a sequence flanking a marker sequence refers, for instance, to nucleic acid hybridization conditions of 5×SSC, 50% formamide, and 42° C. As used herein, "marker assay" means a method for detecting a polymorphism at a particular locus using a particular method, e.g. measurement of at least one phenotype (such as a visually detectable trait, including disease resistance), restriction fragment length polymorphism (RFLP), single base extension, electrophoresis, sequence alignment, allelic specific oligonucleotide hybridization (ASO), random amplified polymorphic DNA (RAPD), microarray-based technologies, PCR-based technologies, and nucleic acid sequencing technologies, etc.

As used herein, a "desirable trait" or "desirable traits" that may be introduced into DM resistant cucumber plants by breeding may be directed to the cucumber fruit or the cucumber plant. Desirable traits to be introduced into cucumber plants and cucumber fruit may be independently selected. Desirable cucumber fruit traits, e.g. as displayed by agronomically elite lines or cultivars, and that may be independently selected include, but are not limited to: fruit size, shape, color, surface appearance; seed number, seed size, locule number; pericarp thickness and toughness; taste, bitterness, the presence of tubercles, and shelf life. Desirable cucumber plant traits, e.g. as displayed by agronomically elite lines or cultivars, and that may be independently selected include, but are not limited to: plant vigor, leaf shape, leaf length, leaf color, plant height, whether the plant is determinate or not, time to maturity, adaptation to field growth, adaptation to greenhouse growth, and resistance to one or more diseases or disease causing organisms such as Verticillium wilt, root knot nematodes, Tobacco Mosaic Virus, Cucumber scab, Anthracnose race 1, Powdery mildew (e.g. caused by *Erysiphe cichoracearum* or *Sphaerotheca fuliginea*), Target spot, Cucumber Mosaic Virus and Fusarium wilt. Any combination of desirable cucumber fruit traits, cucumber plant traits, or cucumber plant and fruit traits may be combined with a DM resistance trait. The resulting agronomically elite DM resistant cucumber plants of the present invention surprisingly display such agronomic traits in combination with DM resistance, while lacking deleterious traits.

As used herein, "polymorphism" means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found, or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs) a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, dsRNA, a transcriptional profile, and a methylation pattern may comprise polymorphisms. In addition, the presence, absence, or variation in copy number of the preceding may comprise a polymorphism.

As used herein, "genotype" is the actual nucleic acid sequence at a locus in an individual plant. As used herein, "phenotype" means the detectable characteristics (e.g. level of DM resistance) of a cell or organism which can be influenced by genotype.

DM resistance of a cucumber plant provided herein can potentially be defined as complete resistance or partial resistance. The DM resistance of a cucumber plant provided herein can be measured by any means available in the art.

In one aspect, DM resistance of a cucumber plant is determined by using a disease rating of foliar chlorotic and/or necrotic lesion development after inoculation or infection with DM on cucumber leaves using a scale of symptoms of 0%, 10%, 20%, 30%, 40%, 50%, 60% and greater than about 60% lesion covering the leaf area. A disease rating of 0% indicates a completely resistant plant.

In another aspect, DM resistance is determined by obtaining disease ratings of symptom development after one or more rounds of inoculation or infection with DM on cucumber leaves and/or cotyledons.

Resistance in a leaf test may be scored on an exemplary scale as follows:

| Index Value | Symptoms |
|---|---|
| 1 | Absence of symptoms |
| 2 | Few small necrotic lesions without expansion |
| 3 | Few chlorotic and some necrotic lesions with limited expansion |
| 4 | Large expanding angular chlorosis with limited necrotic lesions |
| 5 | Large expanding angular chlorosis with expanding necrotic lesions |

Tests are evaluated once symptoms have developed on susceptible checks (e.g. cultivars Maram or SMR58). PI197088 may be used as a "resistant" control; and cv. Poinsett 76 or other cv. exhibiting a comparable level of Downy Mildew resistance may be used as a control to assess "intermediate" levels of resistance/susceptibility to *P. cubensis*. Three observations are made on each plot, one at each end and one in the middle. The mean disease index for each plot is calculated. These are averaged for all three replicates and the standard deviation is determined. The disease index ranges for the categories "Resistant," "Intermediate Resistant" and "Susceptible" are then determined. Varieties are generally trialed several times before a final disease resistance level determination is made. Scores of 1-5 indicate varying levels of resistance or susceptibility. A score of 1-2 after one or more rounds of inoculation or infection, and preferably two or more rounds of infection, indicates a resistant plant. A score of 3 after one or more rounds of inoculation or infection, preferably two or more rounds of infection, indicates a plant exhibiting intermediate resistance. A score of 4-5 indicates a susceptible plant. Scores on this 1-5 scale would correlate to a 1-9 scale where 1=1, 2=3, 3=5, 4=7, and 5=9. The degree of resistance may also be assessed by an alternative rating scale, for instance as described in Example 6.

In one aspect of the invention, a plant is assayed for DM resistance, partial resistance or susceptibility by image analysis of foliar tissue using about 3 leaves per plant captured in a digital image. The image analysis is conducted to determine the percentage of tissue damage and derive a disease rating. Image analysis software and methods used for quantifying visual differences in two or three dimensions are those set forth in Bright, 1987 (*J. Microscopy* 148:51-87) and Bickmore et al., 1999 (*Geol. Mat. Res.* 1(5):1-19). With respect to image analysis: "very resistant" exhibits between about 0% and 5% leaf area symptoms of chlorotic and/or necrotic lesions; "resistant" is between about 1% and 20% of the leaf area having symptoms of chlorotic and/or necrotic lesions; "substantially resistant" is between about 20% and 30% of the leaf area having symptoms of chlorotic and/or necrotic lesions; "mid-resistant" is between 40% and 50% of the leaf area having symptoms of chlorotic and/or necrotic lesions; "partially resistant" is less than or equal to about 50% of the leaf area having symptoms of chlorotic and/or necrotic lesions; "mid-susceptible" is between about 50% and 60% of the leaf area having symptoms of chlorotic and/or necrotic lesions; and "susceptible" is between about 60% and 100% of the leaf area having symptoms of chlorotic and/or necrotic lesions. A resistant plant can be characterized by other aspects as set forth herein, or by the use of other means, such as quantitative PCR to determine the level of infection.

Cucumber lines having DM resistance, or partial resistance, demonstrate a reduced level of symptoms relative to a non-resistant control cucumber line after inoculation or infection with DM. The level of symptoms can be used as an indicator of DM resistance. Disease symptoms measured can be any disease symptoms associated with DM infection. Symptoms can be selected from the group consisting of leaf blisters, necrosis, soft fruits, mosaic, chlorotic veins, chlorotic leaf spots, chlorotic and/or light green mosaic on leaves, fruit lesions, or combinations thereof. In one aspect, a DM resistant cucumber line demonstrates a reduction of foliar symptoms of chlorotic and/or necrotic lesions of at least, or greater than, 10%, 20%, 25%, 30%, 40%, 50%, 60%, 70%, 75%, 80%, 85%, 90%, 95%, or 98% relative to a non-resistant control cucumber line. In other aspects, the leaves of a DM resistant cucumber plant demonstrate less than 15%, or less than 10%, or less than 5%, or less than 2% symptomatic area when exposed to DM. In another aspect, the cucumber plant belongs to a cucumber variety or cultivar, and in another aspect, the cucumber plant is an inbred cucumber plant.

In another aspect, the cucumber plants and varieties provided herein demonstrate little or no symptoms of chlorotic and/or necrotic lesions after inoculation or infection with DM. In some aspects, a DM resistant cucumber plant demonstrates symptoms of chlorotic and/or necrotic lesions on less than 10%, 9%, 8%, 7%, 6%, 5%, 4%, 3% 2%, or 1% of the cucumber leaf surface.

DM resistant cucumber plants may exhibit a delay in the onset of symptoms of chlorotic and/or necrotic lesions relative to a non-resistant control cucumber plant. In some embodiments, the DM resistant cucumber plants exhibit a delay of 1, 2, 3, 4, 5, 6, 7, 8, 9, 10, 11, 12, 13, 14, or more days in the onset of symptoms of chlorotic and/or necrotic lesions relative to a control cucumber plant. In other embodiments, the DM resistant cucumber plants exhibit a delay of at least 7 or more days, 10 or more days, or 14 or more days in the onset of symptoms of chlorotic and/or necrotic lesions relative to a control cucumber plant.

In one aspect, the cucumber plant is a seedling at the time of inoculation or infection. In some aspects, the cucumber plant is a seedling at the 4, 5, 6, 7, or 8 leaf stage of development when inoculated. In one aspect, disease symptoms can be measured at any time after pathogenic challenge of a cucumber plant. In other aspects, symptoms can be measured 2, 3, 4, 5, 6, 7, 8, 9, 10, 11, 12, 13, 14, 15, 16, 17, 18, 19, 20, 21, or more days after inoculation. In another aspect, the cucumber plant is any age of plant at the time of inoculation or infection.

In another aspect, disease symptoms can be observed after DM challenge of an entire plant or a part thereof, for example, a plant cutting.

DM resistant cucumber plants of the present invention may exhibit an increase in fruit yield after inoculation or infection with DM relative to a control cucumber plant inoculated with DM. In one aspect, the resistant cucumber plants exhibit a 2%, 5%, 10%, 15%, 20% or more increase in fruit yield, based upon the total mass, number, or total volume of fruit, relative to a control cucumber plant after one or more rounds of inoculation or infection with DM.

The present invention provides for and includes cucumber plants that exhibit resistance to one or more races of DM. In some embodiments, the cucumber plants of the present invention exhibit resistance to 1, 2, 3, 4, 5, 6, 7, 8, 9, 10, or more races of DM.

The present invention provides for a seed of a cucumber plant capable of producing a plant having DM resistance. In one aspect, the cucumber plant can be an open-pollinated variety, a hybrid parent inbred line, or a male sterile line. In another aspect, the invention provides seed of a cucumber plant capable of producing a hybrid cucumber plant having DM resistance.

The cucumber plants of the present invention can be cucumber lines adapted for greenhouse cucumber production or for field cucumber production. In one aspect, the cucumber plants of the present invention are adapted for greenhouse cucumber production.

The present invention also provides a hybrid cucumber having DM resistance. In another aspect, the present invention provides a hybrid cucumber exhibiting DM resistance after inoculation or infection with DM.

Commercially valuable cucumber plants represent one aspect of the present invention. In one aspect, certain cucumber traits, including, for example, fruit size, shape, color, weight, taste and fruit yield may be important to the commercial value of the crop. Fruit size, and shape, may be of particular interest if the cucumbers are grown for processing such as pickling. The present invention provides for a cucumber plant that produces a cucumber fruit having a length of about, or greater than about, 11, 12, 13, or 14 cm. In another aspect, a cucumber plant of the present invention produces a cucumber fruit having a length between about 11 and 13 cm, 12 and 14 cm, and 11 and 14 cm.

In some aspects, a cucumber plant of the present invention may produce a cucumber fruit having a weight at harvest of about or greater than about 80, 85, 90, 95, 100, 105, 110, 115, 120, and 125 grams. In other aspects, a cucumber plant of the present invention produces a cucumber fruit having a weight at harvest between about 80 and about 125 grams, about 90 and about 115 grams, about 100 and about 120 grams, about 90 and about 125 grams, about 95 and about 125 grams, about 100 and about 125 grams, or between about 115 and about 125 grams. Fruit weight is measured by weighing individual cucumber fruit on a scale.

Mature cucumber fruit produced by DM resistant plants of the present invention may have a diameter from about 10, 11, 12, 13, or 14 mm or larger. In some embodiments the diameter of the cucumber fruit may be from about 10 to about 11 mm, or from about 10 to about 12 mm, or from about 11 to about 13 mm, or from about 12 to about 14 mm, or from about 13 to about 14 mm.

A cucumber fruit attribute such as shape, weight, or size can be measured or evaluated at a variety of times. In one aspect, an attribute is measured following growth in a growth chamber. In another aspect, an attribute is measured at the time of harvest. In yet another aspect, an attribute is measured after storage of the cucumber fruit at ambient conditions for one day, two days, three days, four days, five days, six days, seven days, eight days, nine days, ten days, eleven days, twelve days, thirteen days, two weeks, three weeks, four weeks, or five weeks after harvest.

In one embodiment, a cucumber fruit from a cucumber plant having DM resistance has an overall fruit quality rating of 1, 3, 5, 7, or 9, where fruit quality is measured by visual inspection, with a scale ranging from 1=excellent through 9=poor: Rating 1=Excellent; 3=Above average; 5=Average; 7=Below average; 9=Poor; compared to the standard commercial hybrids grown in the area. Fruit Quality relates to fruit color, fruit shape, fruit length and diameter.

A further aspect of the invention relates to tissue cultures of the cucumber plants described herein. As used herein, the term "tissue culture" indicates a composition comprising isolated cells of one or more types, or a collection of such cells organized into parts of a plant. Tissue culture includes, but is not limited to, compositions comprising protoplasts and calli. Tissue culture also includes, but is not limited to, compositions comprising plant cells that are present in intact plant tissues, or parts of plants, such as embryo, leaf, peduncle, pedicel, anther, meristem, tip and segments of root, stump and stem, explants, and the like. In one aspect, a tissue culture comprises embryos, protoplasts, meristematic cells, pollen, leaves, anthers or cells derived from immature tissues of these plant parts. Means for preparing and maintaining plant tissue cultures are well known in the art. Examples of processes of tissue culturing and regeneration of cucumber are described in, for example, Fillatti et al., 1987 (*Bio/Technology*, 5:726-730). In some aspects, tissue culture of the cucumber plants described herein relates to the culture of protoplasts, calli, or plant cells, that are isolated from, or present in, intact parts of the DM resistant plants described herein. In another aspect, tissue culture refers to the culture of protoplasts, calli, or plant cells, that are isolated from, or present in, intact parts of plants of one or more DM resistant cucumber plant lines selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, and DM resistant progeny thereof, including those produced by crosses or backcrosses, as listed in U.S. patent application Ser. No. 12/424,452, published as US 2009-0265803, the entire disclosure of which is incorporated herein by reference. Representative samples of seed of said lines ASL147-2027, EUR154-1012GY, EUR154-1021GY, GSP33-1094GY, and GPN33-1093GY have been deposited under ATCC Accession Number PTA-9375, ATCC Accession Number PTA-8930, ATCC Accession Number PTA-8931, ATCC Accession Number PTA-8953, and ATCC Accession Number PTA-8954.

In yet another aspect, tissue culture of the cucumber plants described herein relates to the culture of protoplasts, calli, or plant cells, that are isolated from, or present in, intact parts of the DM resistant plants described herein.

Once DM resistant plants are produced, the plants themselves can be cultivated in accordance with conventional procedures. DM resistant progeny may be obtained through sexual reproduction. The seeds resulting from sexual reproduction can be recovered from the fruit of DM resistant plants and planted or otherwise grown as a means of propagation. DM resistant progeny may also be obtained from DM resistant plants through asexual reproduction. Protoplast or propagules (e.g., cuttings, scions or rootstocks) can be recovered from DM resistant plants or parts thereof and may be employed to propagate DM resistant plants.

The present invention also provides for and includes a container of cucumber seeds in which cucumber plants grown from greater than 50% of the seeds have resistance or partial resistance to DM. In another aspect, cucumber plants grown from greater than 55%, 65%, 75%, 85%, 90%, 95%, 98%, or 99% of the cucumber seeds in the container have DM resistance. Another aspect of the invention relates to seeds from a cucumber plant selected from the group consisting of: ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, and DM resistant progeny thereof, wherein cucumber plants grown from about 50%, or greater than 50%, of the seeds have resistance or partial resistance to DM.

The container of cucumber seeds can contain any number, weight or volume of seeds. For example, a container can contain about, or greater than about, 10, 25, 50, 200, 400, 700, 1000, 2000, 3000, or more seeds. In another aspect, a container can contain about, or greater than about, 1 gram, 5, 10, 15, 25, 100, 250, 500, or 1,000 grams of seeds. Alternatively, the container can contain about or at least, or greater than, about 1 ounce, 2, 4, 8, 10 ounces, 1 pound, 2, 4, 8, 12 pounds or more of seeds.

Containers of cucumber seeds can be any container available in the art. For example, a container can be a box, a bag, a packet, a pouch, a tape roll, a foil, a pail, or a tube.

The present invention includes and provides for a container of cucumber fruit from cucumber plants having DM resistance. In one aspect, the container contains about 2, 5, 10, 20, 40, 80, 100, or more cucumber fruit. In yet another aspect, the present invention provides a cucumber vine having cucumber fruit from a plant having resistance to DM.

One aspect of the invention relates to dried, or otherwise processed, cucumber fruit, produced by a cucumber plant having a genome that comprises at least one genetic locus giving rise to DM resistance when expressed in a cucumber plant. Processed cucumber fruit includes, but is not limited to fruit pulp, stewed cucumbers, canned, pickled, minced, sliced, or crushed cucumber fruit. In some aspects, the dried, pickled, or otherwise processed cucumber fruit, is the fruit of a cucumber plant of a line selected from the group consisting of: ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1.

The present invention provides for an inbred cucumber plant having resistance to DM, wherein the resistance is exhibited when the plant is in contact with DM. In one aspect, the inbred cucumber plant is derived from accession PI197088.

The present invention includes and provides for *C. sativus* plants having at least one allele for a DM resistance trait. The DM resistant cucumber plants can be either heterozygous or homozygous for the DM resistance trait. In one embodiment, the DM resistant trait can be linked to variations in a single gene (e.g., linked to one or more alleles of a single gene). In another embodiment, the DM resistance trait can be linked to variations at one or one or more quantitative trait loci (QTL). In a yet another embodiment, the DM resistant cucumber plants are homozygous for the DM resistance trait.

The present invention provides for a *C. sativus* cucumber plant having a genome that comprises at least one genetic locus that provides DM resistance from a non-*C. sativus* plant. In some aspects, the DM resistant cucumber plant is selected from the group consisting of: ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, and DM resistant progeny thereof. In one aspect, the genetic locus derived from a DM resistant cucumber plant can be identified using genetic markers.

The present invention provides for a DM resistant *C. sativus* cucumber plant having less than or equal to 50% of its genome derived from a non-*C. sativus* DM resistant plant. In another aspect, a DM resistant *C. sativus* cucumber plant can have 50%, 25%, 12.5%, 6%, 3% or less nuclear DNA derived from a DM resistant non-*C. sativus* plant. In other aspects, a DM resistant *C. sativus* cucumber plant can have 50%, 25%, 12.5%, 6% or 3% or less nuclear DNA derived from another member of the *Cucumis* genus that is DM resistant.

The present invention provides progeny of cucumber plants having resistance to DM. As used herein, progeny include not only, without limitation, the products of any cross (be it a backcross or otherwise) between two plants, but all progeny whose pedigree traces back to the original cross. In one aspect of the present invention, the progeny contain about 50%, 25%, 12.5% or less nuclear DNA from a DM resistant cucumber plant and expresses the genetic material that provides DM resistance. Representative populations of cucumber plants comprising progeny having resistance to DM include progeny of the cross of susceptible parent cv. Lucinde×PI197088, as well as the API and VJ populations, generated from crossing each of two susceptible parents (API-45-5312-MO and VJ03-68-06) by the same resistant line (PI197088).

One embodiment of the present invention provides for a DM resistant cucumber plant that contains a genetic marker linked to one or more DM resistance locus. By "DM resistance locus" is meant a locus that contributes to DM resistance either alone or in combination with one more other DM resistance locus. By "contributes to Downy Mildew resistance" it is meant that the degree of Downy Mildew resistance is increased in the corresponding plant, either when the locus is alone or in combination with one or more other locus.

In one embodiment of the invention, a marker linked to one or more DM resistance loci includes one or more of the following: CAPs_21826, CAPs_ENK60, CAPs_ENK59, CAPs_17170, CAPs_17179, CAPs_18229 CAPs_17563/66, and CAPs_ENK70. In another embodiment of the invention, the assayed markers linked to one or more DM resistance loci include each of the following: CAPs_ENK60, CAPs_17170, and CAPs_17563/66. In yet another embodiment, the marker(s) linked to one or more DM resistance loci includes one or more SNP marker(s) selected from the group consisting of: NN0223782, NN0225385, NN0226670, NN0224124, NN0246472, NN0225358, NN0227700, NN0224617, NN0247695, NN0227242, NN0223824, NN0223181, NN0226638, NN0225012, NN0228579, NN0226451, NN0225088, NN0226219, NN0247551, NN0246357, NN0225551, NN0226732, NN0247689, NN0247342, NN0224702, NN0225482, NN0224538, NN0247543, NN0224041, NN0228853, NN0227762, NN0227587, NN0228457, NN0246356, NN0246332, NN0223399, NN0223689, NN0247731, NN0226166, NN0225480, NN0246411, NN0227759, NN0247348, NN0228465, NN0247786, NN0226645, NN0223809, NN0227071, NN0226870, NN0228148, NN0246378, NN0224041, NN0227587, NN5096749, NN0224856, NN0223160, NN0223809, NN0226631, NN0227981, NN0247786, NN0226425, NN0224495, NN0225088, NN0227071, NN0223782, NN0228579, NN0247342, and NN0247731, comprising a single nucleotide polymorphism of one of SEQ ID NOs:20-87.

As used herein, linkage of two nucleic acid sequences, including a nucleic acid marker sequence and a nucleic acid sequence of a genetic locus imparting a desired trait such as DM resistance, may be genetic or physical or both. In one aspect of the invention, the nucleic acid marker and genetic locus conferring DM resistance are genetically linked, and exhibit a LOD score of greater than 2.0, as judged by interval mapping for the DM resistance trait based on maximum likelihood methods described by Lander and Botstein, 1989 (*Genetics,* 121:185-199), and implemented in the software package MAPMAKER (e.g. Lander et al., *Genomics* 1:174-181, (1987); default parameters). Alternatively, other software such as QTL Cartographer v1.17 (Basten et al., Zmap—a QTL cartographer. In: Proceedings of the 5th World Congress on Genetics Applied to Livestock Production: Computing Strategies and Software, edited by C. Smith, J. S. Gavora, B. Benkel, J. Chesnais, W. Fairfull, J. P. Gibson, B. W. Kennedy and E. B. Burnside. Volume 22, pages 65-66. Organizing Committee, 5th World Congress on Genetics Applied to Livestock Production, Guelph, Ontario, Canada, 1994; and Basten et al., QTL Cartographer, Version 1.17. Department of Statistics, North Carolina State University, Raleigh, N.C., 2004) may be used. Mapping of QTLs is well-described (e.g. WO 90/04651; U.S. Pat. Nos. 5,492,547, 5,981,832, 6,455,758; reviewed in Flint-Garcia et al. 2003 (*Ann. Rev. Plant Biol.* 54:357-374, the disclosures of which are hereby incorporated by reference). In other embodiments, the marker and region conferring DM resistance are genetically linked and exhibit a LOD score of greater than 3.0, or a LOD score of greater than 6.0, 9.0, 12.0, 15.0, or 18.0. In one embodiment, the marker and region contributing to DM resistance are genetically linked and exhibit a LOD score of between about 14 and about 20. When assigning the presence of a QTL, the LOD threshold score associated with a QTL analysis as described herein may be determined to be significant at the 95% confidence level, or higher, such as at the 98% or 99% confidence level.

In another aspect, the nucleic acid marker is genetically linked at a distance of between about 0 and about 50 centimorgans (cM) to the DM resistance locus. In other embodiments, the distance between the nucleic acid marker and the DM resistance locus is between about 0 and about 35 cM, or between about 0 and about 25 cM, or between about 0 and about 15 cM, or between about 0 and about 10 cM, or between about 0 and about 5 cM, including less than about 4, 3, 2 or 1 cM.

In yet another aspect, the invention provides a cucumber plant comprising an introgressed chromosomal region from chromosome 2 of PI197088 or a progeny plant thereof, of 20 cM, 10 cM, 5 cM, or 1 cM within the region defined as spanning the positions of SNP marker NN0246378 and SNP marker NN0246472; or SNP marker NN0246378 and SNP marker NN0247695. In still yet another aspect, the invention provided a cucumber plant comprising an introgressed chromosomal region from chromosome 4 of PI197088 or a progeny plant thereof, of 20 cM, 10 cM, 5 cM, or 1 cM within the region defined as spanning the positions of SNP marker NN0225012 and SNP marker NN0227587; or SNP marker NN0228579 and SNP marker NN0224495; or SNP marker NN0225088 and SNP marker NN224041. In yet another aspect, the invention provides a cucumber plant comprising an introgressed chromosomal region from chromosome 5 of PI197088 or a progeny plant thereof, of 20 cM, 10 cM, 5 cM, or 1 cM within the region defined spanning the positions of SNP marker NN5096749 and NN0227071; or SNP marker NN5096749 and SNP marker NN0223160; or SNP marker NN0224856 and SNP marker NN0223160. In still other embodiments, the cucumber plant may comprise an introgressed chromosomal region of chromosome 2 from PI197088 and an introgressed chromosomal region of chromosome 4 or 5 of PI197088, wherein the introgressed chromosomal regions allow for enhanced resistance to DM, relative to an otherwise isogenic cucumber line not comprising one or more of the introgressed region(s).

Further, the cucumber plant may comprise an introgressed chromosomal region of chromosome 4 from PI197088 and an introgressed chromosomal region of chromosome 2 and/or 5 of PI197088, or an introgressed region from chromosome 5 of PI197088 or a progeny thereof, and an introgressed chromosomal region of chromosomes 2 and/or 4 of PI197088 or a progeny plant thereof, wherein the introgressed chromosomal region(s) allow for enhanced resistance to DM, relative to an otherwise isogenic cucumber line not comprising one or more of the introgressed region(s).

In particular embodiments, the introgressed chromosomal fragment from PI197088 or a progeny plant thereof, comprises a chromosomal region of about 20 cM, 10, cM, 5 cM, or 1 cM, and further comprises a PI197088-derived allele at SNP marker NN0226631 of chromosome 5. In yet other embodiments, the introgressed chromosomal fragment from PI197088 or a progeny plant thereof, comprises a chromosomal region of about 20 cM, 10, cM, 5 cM, or 1 cM, and further comprises a PI197088-derived allele at SNP marker NN0246425 of chromosome 4.

In another aspect, the nucleic acid marker sequence may be physically linked to a DM resistance locus. In some aspects, the nucleic acid sequence of the genetic marker specifically hybridizes to a nucleic acid molecule having a sequence that is within about 30 Mbp, or about 20 Mbp, or about 15 Mbp, or about 10 Mbp, or about 5 Mbp of a DM resistance locus. In another aspect, the nucleic acid sequence of the genetic marker specifically hybridizes to a nucleic acid molecule having a sequence of any of SEQ ID NOs:1-87, or a complement thereof.

As used herein, two nucleic acid molecules are said to be capable of hybridizing to one another if the two molecules are capable of forming an anti-parallel, double-stranded nucleic acid structure. Conventional stringency conditions are described by Sambrook et al., *Molecular Cloning*, A Laboratory Manual, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. In some embodiments, hybridization conditions can be high, moderate or low stringency conditions. Preferred conditions include those using 50% formamide, 5.0×SSC, 1% SDS and incubation at 42° C. for 14 hours, followed by a wash using 0.2×SSC, 1% SDS and incubation at 65° C.

The specificity of hybridization can be affected by post-hybridization washes. For example, the salt concentration in the wash step can be selected from a low stringency of about 2.0×SSC at 50° C. to a moderate stringency of about 1.0×SSC at 50° C. to a high stringency of about 0.2×SSC at 50° C. In addition, the temperature in the wash step can be increased from low stringency conditions at room temperature, about 22° C., to moderate stringency conditions at about 50° C., to high stringency conditions at about 65° C. Both temperature and salt concentration may be varied, or either the temperature or the salt concentration may be held constant while the other variable is changed. In some aspects, the wash step can be performed for 5, 10, 15, 20, 25, 30, or more minutes. In another aspect, the wash step is performed for about 20 minutes. In yet another aspect, the wash step can be repeated 1, 2, 3, 4, or more times using the selected salt concentration, temperature, and time. In another aspect, the wash step is repeated twice.

A genetic marker profile of a plant may be predictive of the agronomic traits of a hybrid produced using that inbred. For example, if an inbred plant of known genetic marker profile and phenotype is crossed with a second inbred of known genetic marker profile and phenotype it is possible to predict the phenotype of the $F_1$ hybrid based on the combined genetic marker profiles of the parent inbreds. Methods for prediction of hybrid performance from genetic marker data are disclosed in U.S. Pat. No. 5,492,547, the disclosure of which is specifically incorporated herein by reference in its entirety. Such predictions may be made using any suitable genetic marker, for example, SSRs, INDELs, RFLPs, AFLPs, SNPs, ISSRs, or isozymes.

Additional markers, such as SSRs, AFLP markers, RFLP markers, RAPD markers, phenotypic markers, SNPs, isozyme markers, or microarray transcription profiles that are genetically linked to or correlated with DM resistance can be utilized (Walton, *Seed World* 22-29 (July, 1993); Burow and Blake, *Molecular Dissection of Complex Traits,* 13-29, Eds. Paterson, CRC Press, New York (1988)). Methods to isolate such markers and to design probes or primers useful in following the presence of such markers are known in the art. For example, locus-specific SSRs can be obtained by screening a cucumber genomic library for SSRs, sequencing of "positive" clones, designing primers which flank the repeats, and amplifying genomic DNA with these primers. Likewise, SNP markers may be identified as well.

The genetic linkage of marker molecules to DM resistance can be established by a gene mapping model such as, without limitation, the flanking marker model, and the interval mapping, based on maximum likelihood methods described by Lander and Botstein, 1989 (*Genetics,* 121:185-199), and implemented in the software packages MAPMAKER (Whitehead Institute for Biomedical Research, Cambridge Mass., USA) or QTL Cartographer (North Carolina State University, Bioinformatics Research Center) or the like.

A maximum likelihood estimate (MLE) for the presence of a marker is calculated, together with an MLE assuming no trait effect, to avoid false positives. A $\log_{10}$ of an odds ratio (LOD) is then calculated as: LOD=$\log_{10}$ (MLE for the presence of a trait (MLE given no linked trait)).

The LOD score essentially indicates how much more likely the data are to have arisen assuming the presence of a resistance allele rather than in its absence. The LOD threshold value for avoiding a false positive with a given confidence, say 95%, depends on the number of markers and the length of the genome. Graphs indicating LOD thresholds are set forth in Lander and Botstein (1989), and further described by Ars and Moreno-Gonzalez, *Plant Breeding*, Hayward, Bosemark, Romagosa (eds.) Chapman & Hall, London, pp. 314-331 (1993), and van Ooijen (*Heredity* 83:613-624, 1999).

Selection of appropriate mapping or segregation populations is important in trait mapping. The choice of appropriate mapping population depends on the type of marker systems employed (Tanksley et al., Molecular mapping plant chromosomes. Chromosome structure and function: Impact of new concepts J. P. Gustafson and R. Appels (eds.), Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted x exotic) and generally yield greatly reduced linkage distances. Wide crosses will usually provide segregating populations with a relatively large array of polymorphisms when compared to progeny in a narrow cross (adapted×adapted).

Advanced breeding lines are collected from breeding programs. These are tested for their phenotype (e.g. their disease score reactions to DM), and genotyped for markers in the DM QTL intervals. From these data, the smallest genetic interval is identified within each QTL containing the donor parent (DP) favorable allele among the DM resistant lines. This interval is inferred to be critical for conferring resistance to DM. Candidate genetic intervals associated with DM resistance were detected as regions showing enhanced frequency of the favorable allele from the DM resistance donor PI197088 relative to a baseline set of DM susceptible samples from the same germplasm classification type (GCT). For example, comparisons may be made among DM resistant and susceptible inbreds within a single GCT and a single breeding program. Allele frequency shifts between phenotypic classes may be detected by calculating a linkage assessment score (LAS) as: LAS=(Frequency of favorable allele in samples with favorable phenotype)×(Frequency of unfavorable allele in samples with unfavorable phenotype).

As used herein, the progeny include not only, without limitation, the products of any cross (be it a backcross or otherwise) between two plants, but all progeny whose pedigree traces back to the original cross. Specifically, without limitation, such progeny include plants that have 50%, 25%, 12.5% or less nuclear DNA derived from one of the two originally crossed plants. As used herein, a second plant is derived from a first plant if the second plant's pedigree includes the first plant.

The present invention provides a genetic complement of the cucumber lines described herein. Further provided is a hybrid genetic complement, wherein the complement is formed by the combination of a haploid genetic complement from elite inbred cucumber lines described herein and another haploid genetic complement. Means for determining such a genetic complement are well-known in the art.

As used herein, the phrase "genetic complement" means an aggregate of nucleotide sequences, the expression of which defines the phenotype of a plant, such as a *C. sativus* cucumber plant or a cell or tissue of that plant. By way of example, a *C. sativus* cucumber plant is genotyped to determine a representative sample of the inherited markers it possesses. Markers are preferably inherited in codominant fashion so that the presence of both alleles at a diploid locus is readily detectable, and they are free of environmental variation, i.e., their heritability is close to, or equal to, 1. This genotyping is preferably performed on at least one generation of the descendant plant for which the numerical value of the trait or traits of interest are also determined. The array of single locus genotypes is expressed as a profile of marker alleles, two at each locus for a diploid plant. The marker allelic composition of each locus can be either homozygous or heterozygous. Homozygosity is a condition where both alleles at a locus are characterized by the same conditions of the genome at a locus (e.g., the same nucleotide sequence). Heterozygosity refers to different conditions of the genome at a locus. Potentially any type of genetic marker could be used, for example, simple sequence repeats (SSRs), insertion/deletion polymorphism (INDEL), restriction fragment length polymorphisms (RFLPs), amplified fragment length polymorphisms (AFLPs), single nucleotide polymorphisms (SNPs), and isozymes.

Considerable genetic information can be obtained from a completely classified $F_2$ population using a codominant marker system (Mather, Measurement of Linkage in Heredity: Methuen and Co., (1938)). An $F_2$ population is the first generation of self or sib pollination after the hybrid seed is produced. Usually a single $F_1$ plant is self or sib pollinated to generate a population segregating for the nuclear-encoded genes in a Mendelian (1:2:1) fashion.

In contrast to the use of codominant markers, using dominant markers often requires progeny tests (e.g., $F_3$ or back cross self families) to identify heterozygous individuals. The information gathered can be equivalent to that obtained in a completely classified $F_2$ population. This procedure is, however, often prohibitive because of the cost and time involved in progeny testing. Progeny testing of $F_2$ individuals is often used in map construction where error is associated with single plant phenotyping, or when sampling the plants for genotyping affects the ability to perform accurate phenotyping, or where trait expression is controlled by a QTL. Segregation data from progeny test populations (e.g., $F_3$ or backcrossed or selfed families) can be used in trait mapping. Marker-assisted selection can then be applied to subsequent progeny based on marker-trait map associations ($F_2$, $F_3$), where linkage has not been completely disassociated by recombination events (i.e., maximum disequilibrium).

Recombinant inbred lines (RILs) (genetically related lines; usually $>F_5$) can be used as a mapping population. RILs can be developed by selfing F2 plants, then selfing the resultant F3 plants, and repeating this generational selfing process, thereby increasing homozygosity. Information obtained from dominant markers can be maximized by using RILs because all loci are homozygous or nearly so. Under conditions of tight linkage (i.e., about <10% recombination), dominant and co-dominant markers evaluated in RIL populations provide more information per individual than either marker type in backcross populations (e.g. Reiter et al., 1992; *Proc. Natl. Acad. Sci. (U.S.A.)* 89:1477-1481). However, as the distance between markers becomes larger (i.e., loci become more independent), the information in RIL populations decreases dramatically when compared to codominant markers.

Backcross populations can be utilized as mapping populations. A backcross population (BC) can be created by crossing an $F_1$ to one of its parents. Typically, backcross populations are created to recover the desirable traits (which may include most of the genes) from one of the recurrent parental (the parent that is employed in the backcrosses) while adding one or a few traits from the second parental, which is often referred to as the donor. A series of backcrosses to the recurrent parent can be made to recover most of the recurrent parent's desirable traits. Thus a population is created consisting of individuals nearly like the recurrent parent, wherein each individual carries varying amounts or a mosaic of genomic regions from the donor parent. Backcross populations can be useful for mapping dominant markers particularly if all loci in the recurrent parent are homozygous and the donor and recurrent parent have contrasting polymorphic marker alleles (Reiter et al., 1992; *Proc. Natl. Acad. Sci. (U.S.A.)* 89:1477-1481).

Information obtained from backcross populations using either codominant or dominant markers is less than that obtained from completely classified $F_2$ populations because recombination events involving one, rather than two, gametes are sampled per plant. Backcross populations, however, are more informative (at low marker saturation) when compared to RILs as the distance between linked loci increases in RIL populations (i.e., about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the loci polymorphic between the parentals are expected to segregate in the highly homozygous NIL population. Those loci that are polymorphic in a NIL population, however, are likely to be linked to the trait of interest.

Bulk segregant analysis (BSA) is a method developed for the rapid identification of linkage between markers and traits of interest (Michelmore, et al., 1991; *Proc. Natl. Acad. Sci. (U.S.A.)* 88:9828-9832). In BSA, two bulk DNA samples are drawn from a segregating population originating from a single cross. These bulk samples contain individuals that are identical for a particular trait (e.g., resistant or susceptible to a particular pathogen) or genomic region but arbitrary at unlinked regions (i.e., heterozygous). Regions unlinked to the target trait will not differ between the bulked samples of many individuals in BSA.

In another aspect, the present invention provides a method of producing a DM resistant cucumber plant comprising: (a) crossing a cucumber line having DM resistance with a second cucumber line lacking DM resistance to form a segregating population; (b) screening the population for resistance to DM; and (c) selecting one or more members of the population having said DM resistance. In one aspect, the cucumber line having DM resistance is crossed with the second cucumber line for at least two generations (e.g., creating either an $F_2$ or $BC_1S_1$ population). In a particular embodiment, the cucumber line having DM resistance is PI197088, or a progeny thereof. In another aspect, plants are identified as DM resistant prior to crossing. In one aspect, plants can be selected on the basis of partial or complete resistance to DM. In one aspect, the segregating population is self-crossed and the subsequent population is screened for resistance.

In another aspect, the present invention provides a method of introgressing DM resistance into a cucumber plant comprising: (a) crossing at least a first cucumber line having DM resistance with a second cucumber line to form a segregating population; (b) screening said population for resistance to DM; and (c) selecting at least one member of said population exhibiting DM resistance. In one aspect, the cucumber line having DM resistance is crossed with the second cucumber line for at least two generations (e.g., creating either an $F_2$ or $BC_1S_1$ population), or up to 2-10 generations. In another aspect, plants are identified as DM resistant prior to crossing. In one aspect, the segregating population is self-crossed and the subsequent population is screened for resistance.

Cucumber plants (and parts thereof, including seed, pollen, and ovules) generated using a method of the present invention are also provided, and can be part of or generated from a breeding program. The choice of breeding method depends on the mode of plant reproduction, the heritability of the trait(s) being improved, and the type of cultivar used commercially (e.g., $F_1$ hybrid cultivar, pure line cultivar, etc). Selected, non-limiting approaches for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, fruit size, fruit quality, and/or fruit yield will generally dictate the choice.

For highly heritable traits, a choice of superior individual plants evaluated at a single location will be effective, whereas for traits with low heritability, selection should be based on statistical analyses (e.g., mean values) obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates as parents for new commercial cultivars; those still deficient in traits may be used as parents for hybrids, or to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated self or sib pollinating and selection, producing many new genetic combinations.

The development of new cucumber lines requires the development and selection of cucumber varieties, the crossing of these varieties and selection of superior hybrid crosses. The hybrid seed can be produced by manual crosses between selected male-fertile parents or by using male sterility systems. Hybrids can be selected for certain single gene traits such as flower color, seed yield or herbicide resistance that indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes into parent lines. These lines are used to produce new cultivars. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals in the best families is performed. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding and cross breeding have been used to transfer genes for a simply inherited, highly heritable trait into a desirable homozygous cultivar or inbred line, which is the recurrent parent. The source of the trait to be transferred is called the donor parent. The resulting plant obtained from a successful backcrossing program is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. After multiple backcrossing generations with selection, the resulting line is expected to have the attributes of the recurrent parent (e.g., cultivar) and the desirable trait transferred from the donor parent.

Cross breeding or backcross breeding of a DM resistant cucumber plant may be conducted where the other parent (second cucumber plant) is DM resistant or the other parent is not DM resistant.

Cucumber plants generated of the invention may be generated using a single-seed descent procedure. The single-seed descent procedure, in the strict sense, refers to planting a segregating population, then selecting one plant in this and each subsequent generation to self and create the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several available reference books (e.g., Fehr, *Principles of Cultivar Development* Vol. 1, pp. 2-3 (1987)).

In one aspect of the present invention, the source of DM resistance trait for use in a breeding program is derived from a plant selected from the group consisting of PI197088, ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, and DM resistant progeny thereof, as described in U.S. Patent Application Publication 2009-0265083. In another aspect, the source of the DM resistance trait for use in a breeding program is not derived from a plant selected from the group consisting of PI197088, ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1, and DM resistant progeny thereof.

Another aspect of the invention is directed to an inbred cucumber plant having resistance to DM, wherein said resistance is exhibited when said plant is in contact with said DM, and wherein said cucumber plant is not derived from a plant selected from the group consisting of ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1.

Also included in the invention is a cucumber plant having a genome, wherein said genome comprises a genetic locus conferring resistance to DM, wherein said genetic locus contains one or more genetic markers linked to said genetic locus conferring resistance to DM, and wherein said cucumber plant is not accession PI197088.

In another aspect, additional sources of DM resistance for use in a breeding program can be identified by screening cucumber germplasm for resistance to DM. In yet another aspect, cucumber plants can be screened for DM resistance by identifying germplasm exhibiting reduced disease symptoms relative to a control cucumber plant after inoculation or infection. In one aspect, cucumber plants can be screened for resistance to DM using a test such as a field or greenhouse screen and disease rating schemes as described in Example 1, Example 2, or Example 8.

In another aspect, additional sources of DM resistance for use in a breeding program can be identified by screening with one or more molecular markers linked to a genetic locus conferring resistance to DM, such as those identified herein.

In another aspect, additional sources of DM resistance for use in a breeding program can be identified by a combination of screening cucumber plants for reduced disease symptoms then screening with one or more molecular markers linked to a genetic locus contributing to resistance to DM.

In another aspect, cucumber lines having DM resistance can be used in breeding programs to combine DM resistance with additional traits of interest. In one aspect, DM resistance can be combined with any additional trait, including disease resistant traits, yield traits, and fruit quality traits. For example, breeding programs can be used to combine the DM resistance trait with alleles that contribute to size and shape in cucumber fruit. Breeding programs can also be used to combine DM resistance with one or more disease resistant traits. Such disease resistant traits include, without limitation, resistance to: Verticillium wilt, root knot nematodes, Tobacco Mosaic Virus, Cucumber scab, Powdery mildew, Target spot, Cucumber Mosaic Virus, and Fusarium wilt. In another aspect, the traits that are combined can be co-inherited in subsequent crosses.

The present invention also provides for parts of the DM resistant cucumber plants produced by a method of the present invention. Parts of cucumber plants, without limitation, include plant cells or parts of plant cells, seed, endosperm, meristem, flower, anther, ovule, pollen, fruit, flowers, stems, roots, stalks or leaves, scions, and root stocks. Plant parts also include the parts of a cucumber fruit, which include the placenta, columella and pericarp. In one embodiment of the present invention, the plant part is a seed.

The invention further provides for parts of a cucumber plant having a genome, that comprises at least one genetic locus giving rise to DM resistance in the cucumber plant. In another embodiment, parts of cucumber plants are derived from a cucumber plant selected from the group consisting of the deposited cucumber lines described in U.S. Patent Application Publication 2009-0265083, and DM resistant progeny thereof. In accordance with one aspect of the present invention, the physiological and morphological characteristics of deposited lines ASL147-2027, EUR154-1012GY, EUR154-1021GY, GSP33-1094GY, GPN33-1093GY, 03/8020-20_TUP03_DMFL_1, 03/8024-19_TUP03_DMFL_1, and 03/8039-5_TUP03_DMFL_1 are set forth in Tables 1-8 below.

TABLE 1

Physiological and Morphological Characteristics of Line ASL147-2027 Mo.

| | CHARACTERISTIC | ASL147-2027 |
|---|---|---|
| 1. | Type | Cucumber |
| | Predominate Usage | Slicing |
| | Predominate Culture | Outdoor |
| | Area of Best Adaptation in USA | Most Areas |
| 2. | Maturity | |
| | Days from Seeding to Market | 50-55 |
| 3. | Plant | |
| | Habit | Vine |
| | Growth | Indeterminate |
| | Sex | Monoecious |
| | Flower Color | Yellow |
| 4. | Fruit at Edible Maturity | |
| | Fruit Neck Shape | Not Necked |
| | Fruit Tapering | Ends Blunt or Rounded |
| | Skin Thickness | Thick |
| | Skin Ribs | Ribbed |
| | Skin Toughness | Tough |
| | Skin Luster | Dull |
| | Spine Color | White |
| | Spine Quality | Coarse |
| | Spine Density | Few |
| | Flavor | Bitterfree |
| 5. | Insect Resistance | |
| | Aphid (*Aphis gossypii*) | Susceptible |

TABLE 2

Physiological and Morphological Characteristics of Line EUR154-1012 GY.

| | CHARACTERISTIC | EUR 154-1012 GY |
|---|---|---|
| 1. | Type | Cucumber |
| | Predominate Usage | Fresh |
| | Predominate Culture | Greenhouse |
| | Area of Best Adaptation in USA | Spain |
| 2. | Maturity | |
| | Days from Seeding to Market | 60-65 |
| 3. | Plant | |
| | Habit | Vine |
| | Growth | Indeterminate |
| | Sex | Gynoecious |
| | Flower Color | Yellow |
| 4. | Stem | |
| | Length | 150-200 cm |
| | Internode Length | 5-8 cm |
| | Stem Form | Grooved-Ridged |
| 5. | Fruit at Edible Maturity | |
| | Length | 30-32 cm |
| | Diameter at Medial | 45-50 mm |
| | Weight | 300-400 gm |
| | Skin Color | Medium green |
| | Yellowish Blossom End Strips | No |
| | Predominant Color at Stem End | Uniform green |
| | Predominant Color at Blossom End | Uniform green |
| | Fruit Neck Shape | Medium |
| | Fruit Tapering | Rounded |
| | Stem End Cross Section | rd |
| | Medial Cross Section | rd |
| | Blossom End Cross Section | rd |
| | Skin Thickness | Thin |
| | Skin Ribs | Ribbed |
| | Skin Toughness | Low |
| | Skin Luster | Shiny |
| | Spine Color | White |
| | Spine Quality | Fine |
| | Spine Density | Very low |
| | Tubercles (Warts) | No |
| | Flavor | Bitterfree |
| 6. | Fruit at Harvest Maturity | |
| | Length | 35-37 cm |
| | Diameter at Medial | 50-60 mm |

TABLE 2-continued

Physiological and Morphological Characteristics of Line EUR154-1012 GY.

| | CHARACTERISTIC | EUR 154-1012 GY |
|---|---|---|
| | Color | Yellow |
| | Color Pattern | Striped |
| | Surface | Smooth |
| | Netting | Slight or none |
| | Fruit Set | Normally without seeds |
| 7. | Seeds | |
| | No. per Fruit | 30-80 |
| | Per 1,000 Seeds | 30-35 gm |
| 8. | Disease Resistance | |
| | Cucumber Scab (Gumosis) (*Cladosporium cucumerinum*) | |
| | Downy Mildew | Resistant |
| | Powdery Mildew (*Erysiphe cichoracearum*) | Resistant |
| | Cucumber Mosaic Virus | Susceptible |
| | Cucumber Vein Yellowing Virus | Susceptible |
| | Cucumber yellow Stunted Disorder Virus | Intermediate resistance |
| 9. | Insect Resistance | |
| | Aphid (*Aphis gossypii*) | Susceptible |

TABLE 3

Physiological and Morphological Characteristics of Line EUR 154-1021 GY.

| | CHARACTERISTIC | EUR 154-1021 GY |
|---|---|---|
| 1. | Type | Cucumber |
| | Predominate Usage | Fresh |
| | Predominate Culture | Greenhouse |
| | Area of Best Adaptation in USA | Spain |
| 2. | Maturity | |
| | Days from Seeding to Market | 60-65 |
| 3. | Plant | |
| | Habit | Vine |
| | Growth | Indeterminate |
| | Sex | Gynoecious |
| | Flower Color | Yellow |
| 4. | Stem | |
| | Length | 150-200 cm |
| | Internode Length | 50-80 mm |
| | Stem Form | Grooved-Ridged |
| 5. | Fruit at Edible Maturity | |
| | Length | 30-32 cm |
| | Diameter at Medial | 45-50 mm |
| | Weight | 300-400 gm |
| | Skin Color | Medium green |
| | Yellowish Blossom End Strips | No |
| | Predominant Color at Stem End | Uniform green |
| | Predominant Color at Blossom End | Uniform green |
| | Fruit Neck Shape | Not necked |
| | Fruit Tapering | Rounded |
| | Stem End Cross Section | rd |
| | Medial Cross Section | rd |
| | Blossom End Cross Section | rd |
| | Skin Thickness | Thin |
| | Skin Ribs | Ribbed |
| | Skin Toughness | Low |
| | Skin Luster | Shiny |
| | Spine Color | White |
| | Spine Quality | Fine |
| | Spine Density | Low |
| | Tubercles (Warts) | No |
| | Flavor | Bitterfree |
| 6. | Fruit at Harvest Maturity | |
| | Length | 35-37 cm |
| | Diameter at Medial | 50-60 mm |
| | Color | Yellow |
| | Color Pattern | Striped |
| | Surface | Smooth |

TABLE 3-continued

Physiological and Morphological Characteristics of Line EUR 154-1021 GY.

| | CHARACTERISTIC | EUR 154-1021 GY |
|---|---|---|
| | Netting | Slight |
| | Fruit Set | Normally without seeds |
| 7. | Seeds | |
| | No. per Fruit | 30-80 |
| | Per 1,000 Seeds | 30-35 gm |
| 8. | Disease Resistance | |
| | Downy Mildew | Resistant |
| | Powdery Mildew (*Erysiphe cichoracearum*) | Resistant |
| | Cucumber Mosaic Virus | Susceptible |
| | Cucumber Vein Yellowing Virus | Susceptible |
| | Cucumber yellow Stunted Disorder Virus | Intermediate resistance |
| 9. | Insect Resistance | |
| | Aphid (*Aphis gossypii*) | Susceptible |

TABLE 4

Physiological and Morphological Characteristics of Line GSP 33-1094 GY.

| | CHARACTERISTIC | GSP 33-1094 GY |
|---|---|---|
| 1. | Type | Cucumber |
| | Predominate Usage | Pickling |
| | Predominate Culture | Outdoor |
| | Area of Best Adaptation in USA | Most Areas |
| 2. | Maturity | |
| | Days from Seeding to Market | 60-62 |
| 3. | Plant | |
| | Habit | Vine |
| | Growth | Indeterminate |
| | Sex | 100% Gynoecious |
| | Flower Color | Yellow |
| 4. | Stem | |
| | Length | 150-200 cm |
| | Number of Nodes from Cotyledon Leaves to Node Bearing the First Pistillate Flower | 3-4 |
| | Internode Length | 20-30 |
| | Stem Form | Grooved-Ridged |
| 5. | Leaf | Mature Blade of Third Leaf |
| | Length | 200-250 mm |
| | Width | 150-200 mm |
| | Petiole Length | 6.5-8 |
| 6. | Fruit at Edible Maturity | |
| | Length | 12-14 cm |
| | Diameter at Medial | 35-45 |
| | Weight | 80-120 gm |
| | Skin Color | Mottled or Speckled with yellow |
| | Yellowish Blossom End Strips | Extend Less than ⅓ of the Fruit Length |
| | Predominant Color at Stem End | Medium Green |
| | Predominant Color at Blossom End | Light Green (Arlington White Spine) |
| | Fruit Neck Shape | Not Necked |
| | Fruit Tapering | Ends Blunt or Rounded |
| | Stem End Cross Section | Square |
| | Medial Cross Section | Square |
| | Blossom End Cross Section | Square |
| | Skin Thickness | Thick |
| | Skin Ribs | Ribbed |
| | Skin Toughness | Tender |
| | Skin Luster | Dull |
| | Spine Color | White |
| | Spine Quality | Fine |
| | Spine Density | Many |
| | Tubercles (Warts) | Few, Prominent (Salad) |
| | Flavor | Bitterfree |
| 7. | Fruit at Harvest Maturity | |
| | Length | 25-30 cm |
| | Diameter at Medial | 10-13 |
| | Color | Cream |

TABLE 4-continued

Physiological and Morphological Characteristics of Line GSP 33-1094 GY.

| CHARACTERISTIC | GSP 33-1094 GY |
|---|---|
| Color Pattern | Not Striped |
| Surface | Smooth |
| Netting | Slight or None |
| Fruit Set | Parthenocarpically |
| 8. Seeds | |
| No. per Fruit | 150-200 |
| Per 1,000 Seeds | 22-25 gm |
| 9. Disease Resistance | |
| Cucumber Scab (Gumosis) (*Cladosporium cucumerinum*) | Susceptible |
| Downy Mildew | Resistant |
| Powdery Mildew (*Erysiphe cichoracearum*) | Resistant |
| Target Spot (*Corynespora cassiicola*) | Susceptible |
| Cucumber Mosaic Virus | Resistant |
| 10. Insect Resistance | |
| Aphid (*Aphis gossypii*) | Susceptible |

TABLE 5

Physiological and Morphological Characteristics of Line GPN 33-1093 GY.

| CHARACTERISTIC | GPN 33-1093 GY |
|---|---|
| 1. Type | Cucumber |
| Predominate Usage | Pickling |
| Predominate Culture | Outdoor |
| Area of Best Adaptation in USA | Most Areas |
| 2. Maturity | |
| Days from Seeding to Market | 60-65 |
| 3. Plant | |
| Habit | Vine |
| Growth | Indeterminate |
| Sex | Primarily Gynoecious |
| Flower Color | Yellow |
| 4. Stem | |
| Length | 150-200 cm |
| Number of Nodes from Cotyledon Leaves to Node Bearing the First Pistillate Flower | 2-3 |
| Internode Length | 20-25 |
| Stem Form | Grooved-Ridged |
| 5. Leaf | Mature Blade of Third Leaf |
| Length | 200-230 mm |
| Width | 150-200 mm |
| Petiole Length | 4-8 |
| 6. Fruit at Edible Maturity | |
| Length | 11-13 cm |
| Diameter at Medial | 35-45 |
| Weight | 80-120 gm |
| Skin Color | Mottled or Speckled with yellow |
| Yellowish Blossom End Strips | Extend Less than ⅓ of the Fruit Length |
| Predominant Color at Stem End | Medium Green |
| Predominant Color at Blossom End | Light Green (Arlington White Spine) |
| Fruit Neck Shape | Not Necked |
| Fruit Tapering | Ends Blunt or Rounded |
| Stem End Cross Section | Square |
| Medial Cross Section | Square |
| Blossom End Cross Section | Square |
| Skin Thickness | Thick |
| Skin Ribs | Ribbed |
| Skin Toughness | Tender |
| Skin Luster | Dull |
| Spine Color | White |
| Spine Quality | Fine |
| Spine Density | Few |
| Tubercles (Warts) | Few, Prominent (Salad) |
| Flavor | Bitterfree |

TABLE 5-continued

Physiological and Morphological Characteristics of Line GPN 33-1093 GY.

| CHARACTERISTIC | GPN 33-1093 GY |
|---|---|
| 7. Fruit at Harvest Maturity | |
| Length | 25-30 cm |
| Diameter at Medial | 10-13 |
| Color | Cream |
| Color Pattern | Striped |
| Surface | Smooth |
| Netting | Slight or None |
| Fruit Set | Normally with Seeds |
| 8. Seeds | |
| No. per Fruit | 150-200 |
| Per 1,000 Seeds | 22-25 gm |
| 9. Disease Resistance | |
| Cucumber Scab (Gumosis) (*Cladosporium cucumerinum*) | Susceptible |
| Downy Mildew | Resistant |
| Powdery Mildew (*Erysiphe cichoracearum*) | Resistant |
| Target Spot (*Corynespora cassiicola*) | Susceptible |
| Cucumber Mosaic Virus | Resistant |
| 10. Insect Resistance | |
| Aphid (*Aphis gossypii*) | Susceptible |

TABLE 6

Physiological and Morphological Characteristics: Line 03/8020-20_TUP03_DMFL_1.

| CHARACTERISTIC | 03/8020-20_TUP03_DMFL_1 |
|---|---|
| 1. Type | Cucumber |
| Predominate Usage | Fresh |
| Predominate Culture | Outdoor |
| Area of Best Adaptation in USA | Turkey & ½ East |
| 2. Maturity | |
| Days from Seeding to Market | 60-65 |
| 3. Plant | |
| Habit | Vine |
| Growth | Indeterminate |
| Sex | Monoecious |
| Flower Color | Yellow |
| 4. Stem | |
| Length | 150-200 cm |
| Internode Length | 30-50 mm |
| Stem Form | Grooved-Ridged |
| 5. Fruit at Edible Maturity | |
| Length | 12-15 cm |
| Diameter at Medial | 35-45 |
| Weight | 80-120 gm |
| Skin Color | Green |
| Yellowish Blossom End Strips | No |
| Predominant Color at Stem End | Uniform green |
| Predominant Color at Blossom End | Uniform green |
| Fruit Neck Shape | Not Necked |
| Fruit Tapering | Ends Blunt or Rounded |
| Stem End Cross Section | rd |
| Medial Cross Section | rd |
| Blossom End Cross Section | rd |
| Skin Thickness | Thin |
| Skin Ribs | Not ribbed |
| Skin Toughness | Low |
| Skin Luster | Shiny |
| Spine Color | White |
| Spine Quality | Fine |
| Spine Density | High |
| Tubercles (Warts) | No |
| Flavor | Bitterfree |
| 6. Fruit at Harvest Maturity | |
| Length | 18-20 cm |
| Diameter at Medial | 30-45 mm |
| Color | Cream |
| Color Pattern | Striped |

TABLE 6-continued

Physiological and Morphological Characteristics:
Line 03/8020-20_TUP03_DMFL_1.

| CHARACTERISTIC | 03/8020-20_TUP03_DMFL_1 |
|---|---|
| Surface | Smooth |
| Netting | Slight or None |
| Fruit Set | Normally with Seeds |
| 7. Seeds | |
| No. per Fruit | 150-200 |
| Per 1,000 Seeds | 22-25 gm |
| 8. Disease Resistance | |
| Cucumber Scab (Gumosis) (*Cladosporium cucumerinum*) | Resistant |
| Downy Mildew (*Pseudoperonospora cubensis*) | Resistant |
| Powdery Mildew (*Erysiphe cichoracearum*) | Susceptible |
| Cucumber Mosaic Virus | Susceptible |
| 9. Insect Resistance | |
| Aphid (*Aphis gossypii*) | Susceptible |

TABLE 7

Physiological and Morphological Characteristics:
Line 03/8024-19_TUP03_DMFL_1.

| CHARACTERISTIC | 03/8024-19_TUP03_DMFL_1 |
|---|---|
| 1. Type | Cucumber |
| Predominate Usage | Fresh |
| Predominate Culture | Outdoor |
| Area of Best Adaptation in USA | Turkey & ½ East |
| 2. Maturity | |
| Days from Seeding to Market | 60-65 |
| 3. Plant | |
| Habit | Vine |
| Growth | Indeterminate |
| Sex | Monoecious |
| Flower Color | Yellow |
| 4. Stem | |
| Length | 150-200 cm |
| Internode Length | 30-50 mm |
| Stem Form | Grooved-Ridged |
| 5. Fruit at Edible Maturity | |
| Length | 15-17 cm |
| Diameter at Medial | 35-45 |
| Weight | 80-120 gm |
| Skin Color | Green |
| Yellowish Blossom End Strips | No |
| Predominant Color at Stem End | Uniform green |
| Predominant Color at Blossom End | Uniform green |
| Fruit Neck Shape | Not necked |
| Fruit Tapering | Ends blunt or rounded |
| Stem End Cross Section | rd |
| Medial Cross Section | rd |
| Blossom End Cross Section | rd |
| Skin Thickness | Thin |
| Skin Ribs | Not ribbed |
| Skin Toughness | Low |
| Skin Luster | Shiny |
| Spine Color | White |
| Spine Quality | Fine |
| Spine Density | Low |
| Tubercles (Warts) | No |
| 6. Fruit at Harvest Maturity | |
| Length | 12-23 cm |
| Diameter at Medial | 30-45 mm |
| Color | Cream |
| Color Pattern | Striped |
| Surface | Smooth |
| Netting | Slight or none |
| Fruit Set | Normally with seeds |
| 7. Seeds | |
| No. per Fruit | 150-200 |
| Per 1,000 Seeds | 22-25 gm |

TABLE 7-continued

Physiological and Morphological Characteristics:
Line 03/8024-19_TUP03_DMFL_1.

| CHARACTERISTIC | 03/8024-19_TUP03_DMFL_1 |
|---|---|
| 8. Disease Resistance | |
| Cucumber Scab (Gumosis) (*Cladosporium cucumerinum*) | Susceptible |
| Downy Mildew | Resistant |
| Powdery Mildew (*Erysiphe cichoracearum*) | Intermediate resistance |
| Cucumber Mosaic Virus | Resistant |
| 9. Insect Resistance | |
| Aphid (*Aphis gossypii*) | Susceptible |

TABLE 8

Physiological and Morphological Characteristics:
Line 03/8039-5_TUP03_DMFL_1.

| CHARACTERISTIC | 03/8039-5_TUP03_DMFL_1 |
|---|---|
| 1. Type | Cucumber |
| Predominate Usage | Fresh |
| Predominate Culture | Outdoor |
| Area of Best Adaptation in USA | Turkey & ½ East |
| 2. Maturity | |
| Days from Seeding to Market | 60-65 |
| 3. Plant | |
| Habit | Vine |
| Growth | Indeterminate |
| Sex | Monoecious |
| Flower Color | Yellow |
| 4. Stem | |
| Length | 150-200 cm |
| Internode Length | 30-50 mm |
| Stem Form | Grooved-Ridged |
| 5. Fruit at Edible Maturity | |
| Length | 16-18 cm |
| Diameter at Medial | 35-45 |
| Weight | 80-120 gm |
| Skin Color | Green |
| Yellowish Blossom End Strips | No |
| Predominant Color at Stem End | Uniform green |
| Predominant Color at Blossom End | Uniform green |
| Fruit Neck Shape | Not necked |
| Fruit Tapering | Ends blunt or rounded |
| Stem End Cross Section | rd |
| Medial Cross Section | rd |
| Blossom End Cross Section | rd |
| Skin Thickness | Thin |
| Skin Ribs | Not ribbed |
| Skin Toughness | Low |
| Skin Luster | Shiny |
| Spine Color | White |
| Spine Quality | Fine |
| Spine Density | Medium |
| Tubercles (Warts) | No |
| Flavor | Bitterfree |
| 6. Fruit at Harvest Maturity | |
| Length | 20-24 cm |
| Diameter at Medial | 30-45 mm |
| Color | Cream |
| Color Pattern | Striped |
| Surface | Smooth |
| Netting | Slight or None |
| Fruit Set | Normally with Seeds |
| 7. Seeds | |
| No. per Fruit | 150-200 |
| Per 1,000 Seeds | 22-25 gm |
| 8. Disease Resistance | |
| Cucumber Scab (Gumosis) (*Cladosporium cucumerinum*) | Resistant |
| Downy Mildew | Resistant |
| Powdery Mildew (*Erysiphe cichoracearum*) | Intermediate resistance |
| Cucumber Mosaic Virus | Susceptible |

TABLE 8-continued

Physiological and Morphological Characteristics:
Line 03/8039-5_TUP03_DMFL_1.

| CHARACTERISTIC | 03/8039-5_TUP03_DMFL_1 |
|---|---|
| 9. Insect Resistance | |
| Aphid (*Aphis gossypii*) | Susceptible |

In one embodiment, the invention provides a DM resistant cucumber plant, or the fruit or seeds thereof, wherein the cucumber plant demonstrates a reduction in foliar symptoms of chlorotic and/or necrotic lesions relative to a non-resistant control plant upon inoculation or infection with DM, and wherein said plant demonstrates resistance to one or more of Verticillium wilt, root knot nematodes, tobacco mosaic virus, cucumber scab, powdery mildew, target spot, cucumber mosaic virus, papaya ringspot virus, zucchini yellow mosaic virus, and Fusarium wilt. In another embodiment, those cucumber plants, or the fruit or seeds thereof, are selected from DM resistant progeny of lines described in Tables 1-8. In other embodiments, a DM resistant cucumber plant that also demonstrates resistance to one or more of: Verticillium wilt, cucumber scab, powdery mildew, target spot, cucumber mosaic virus, nematodes, tobacco mosaic virus papaya ringspot virus, zucchini yellow mosaic virus, and Fusarium wilt displays a greater than 10% reduction, or a greater than 30% reduction, or a greater than 60% reduction in foliar symptoms of chlorotic and/or necrotic lesions upon inoculation or infection with DM. In some aspects, the cucumber plants are adapted either for greenhouse growth or for field growth.

One aspect of the invention provides a DM cucumber plant, or the fruit or seeds thereof, wherein the cucumber plant, or the fruit thereof, expresses one, or two, or three, or more independently selected desirable traits in addition to DM resistance. In one embodiment, the "desirable trait" or "desirable traits" are selected from the group consisting of: fruit size, shape, color, surface appearance; seed number, seed size, locule number; pericarp thickness and toughness; taste, bitterness, the presence of tubercles, and shelf life, plant vigor, leaf shape, leaf length, leaf color, plant height, whether the plant is determinate or not, time to maturity, adaptation to field growth, adaptation to greenhouse growth, and resistance to one or more diseases or disease causing organisms such as Verticillium Wilt, root knot nematodes, Tobacco Mosaic Virus, Cucumber Scab, Powdery Mildew, Downy Mildew, Target Spot, Cucumber Mosaic Virus, and Fusarium Wilt. In another embodiment the "desirable trait" or "desirable traits" are selected from the group consisting of: fruit size, fruit shape, fruit color, fruit taste, the number of seeds per fruit, the size of seeds, the thickness of fruit pericarp tissue, the shelf life of fruit, resistance to Verticillium Wilt, resistance to Cucumber Scab, resistance to Powdery Mildew, resistance to Target Spot, resistance to Cucumber Mosaic Virus, resistance to nematodes, resistance to Tobacco Mosaic Virus, resistance to Papaya Ringspot Virus, resistance to Zucchini Yellow Mosaic virus, and resistance to Fusarium Wilt. In yet another embodiment, the "desirable trait" or "desirable traits" are selected from the group consisting of: fruit size, fruit shape, fruit color, fruit taste, the shelf life of fruit, resistance to Cucumber scab, resistance to Powdery mildew, resistance to Target spot, and resistance to Cucumber mosaic Virus. In still another embodiment the "desirable trait" or "desirable traits" are selected from the group consisting of: fruit size, fruit shape, fruit color, fruit quality acceptable to market, and the shelf life of fruit.

In other aspects of the invention, the plants bearing one or more desirable traits in addition to DM resistance display a greater than 10%, or a greater than 30%, or a greater than 60%, or a greater than 80% reduction in foliar symptoms of chlorotic and/or necrotic lesions relative to a non-resistant control plant upon inoculation or infection with DM. Another aspect of the present invention is directed to a method of producing a DM resistant cucumber plant comprising: crossing a cucumber line having DM resistance with a second plant lacking DM resistance but capable of donating one or more of the aforementioned desirable traits.

EXAMPLES

Example 1

Downy Mildew Culture and Disease Screening—Field

*Pseudoperonospora cubensis* (Berk. et Curt.) Rostow is an obligate pathogen. Therefore, it must be maintained on live plants of a susceptible cucurbit. Two isolates were used in screening for resistance in this study. The "old" isolate of *P. cubensis* is characterized by its pathogenicity on both squash and cucumber. The "new" isolate of *P. cubensis* is not considered pathogenic on squash but is very pathogenic on cucumber. The pathogen was stored by freezing leaves or cotyledons with abundant sporulation at −80° C. Although there may be some loss in spore viability inherent in the freezing process, no decrease in viability over time once spores are frozen, has been found. Six weeks before spreader host plants were to be transplanted in the field, susceptible cucumber hosts were planted in a controlled environment chamber. At three weeks they were inoculated with a spore suspension derived from infected leaves stored in a −80° C. freezer. Inoculated culture plants were maintained at 20° C.; once chlorotic lesions have developed, plants were placed in the dew chamber overnight to induce sporulation. This culture was transferred weekly on cucumber until plants were transplanted into the field.

Trials were direct seeded in the field. Spreader rows of susceptible cucumber were planted in every third row. When spreader rows were two-three weeks old, infected plants (reared in the growth room) were transplanted within the spreader rows. Breeder trials were done simultaneously. Plots were maintained in good horticultural condition, consistent with techniques normally employed for culture of cucumbers in the Southeastern United States.

Spreader plants at the three to four leaf stage were inoculated in the greenhouse by misting with sporangial suspension using a spray bottle. Inoculum was formulated in sterile distilled water. After inoculation, plants were placed in a dew chamber at 100% RH and 20° C., for 18-24 hours. Spreader plants were transplanted to the field where a solid set sprinkler provided a nightly moist period to encourage development and spread of disease.

Tests were evaluated once symptoms had developed on the susceptible check, sometimes called the susceptible control. Controls including PI197088 (resistant control); DMP21, GP14, LLP 1, POINSETT 76, (intermediate-resistant controls); and SPRINT440, MARAM, and SMR58 (susceptible controls) were used. Three observations were made on each plot, one at each end and one in the middle. The mean disease index for each plot was calculated. These were averaged for all three replicates and the standard deviation was determined. The disease index ranges for the categories "Resistant," "Intermediate Resistant" and "Susceptible" were then determined. Varieties were generally trialed several times before a final disease resistance level determination was made. A randomized complete block design was used in the disease test. Each line was replicated three times—approximately 40 plants per entry were tested. Lines with limited seed available were included as a single rep observation plot. Checks were included as entries to gauge the severity of the test. Plots were 12 feet long with a 3-foot alley between ends of blocks. A susceptible spreader was planted in every third row and on the outside borders of the entire planting Example 2

Downy Mildew Culture and Disease Screening—Greenhouse

*Pseudoperonospora cubensis* (Berk. et Curt.) Rostow, as described and stored above in Example 1, was also used for greenhouse screens. Two weeks prior to screen inoculation, susceptible cucumber hosts were sown in seedling trays. At one week post planting, the seedlings are inoculated with a rate of approximately $5 \times 10^4$ sporangia/ml. The inoculated hosts were then placed into a growth chamber and maintained for seven days at about 70° F. After seven days, the seedlings were placed into a dew chamber overnight to induce sporulation. This culture was transferred onto susceptible cucumber hosts on a weekly basis.

Cotyledon screens were planted in seedling trays. Susceptible and resistant checks were planted on both sides of each tray. Plants were seeded and maintained in a greenhouse at 80° F. Inoculation was conducted at 7 to 10 days for cotyledons and at the 5th leaf stage for true leaves. Plants were inoculated by misting with sporangial suspension using a spray bottle at a concentration of about $5 \times 10^4$ sporangia per ml for cotyledons and $1 \times 10^4$ to $3 \times 10^4$ for true leaves. After inoculation, plants were placed in a dew chamber at 100% relative humidity and 20° C., for 18-24 hours.

Tests were evaluated once symptoms have developed on the susceptible check, sometimes called the susceptible control. Controls used were PI197088 (resistant control) MARAM (susceptible control), and SMR58 (resistant control). Resistant and intermediate survivors of the cotyledon screens were kept and transplanted into 3-inch peat pots to be inoculated again or to be transplanted into greenhouse grow bags. Resistant and intermediate survivors of the true leaf screens were transplanted directly into greenhouse grow bags.

Example 3

Introgression of DM resistance into Cucumber Lines

Downy Mildew resistance identified in the Plant Introduction line PI197088 was found to be stable in multiple screening locations worldwide and against both older (pathogenic on squash and cucumber) and newly emerged (not considered pathogenic on squash and very pathogenic on cucumber) isolates of *P. cubensis*. However, both plants and fruit of PI197088 are commercially unacceptable. A locus contributing to Downy Mildew resistance in PI197088 was mapped with molecular markers as described in Example 4. A total of about 128 cucumber lines were separately screened using one or both DM isolates. DNA was isolated from resistant lines to screen for marker polymorphisms between the donor and recurrent parents.

Included in these screens were cucumber varieties Conquistador, Crispina, DMP21, and PI197088, among others, which are resistant or intermediate-resistant. Also included were Colt, Sprint440, Talladega, Lucinde, and Serena, among others, as susceptible control lines. Tissue samples from each of the DM resistant lines were collected for use in DNA analysis and production of a DNA library to identify markers associated with DM resistance. Seeds were also obtained from each of the lines demonstrating DM resistance generally via mixed pollen pollinations within each accession, and where possible via selfing. Mixed pollen pollinations were generally used in wild type cucumbers as they often contain a self-incompatibility factor.

Initial crosses were made between PI197088 and a recurrent susceptible parent (cv. Lucinde) to create $F_1$ plants. Plants derived from these crosses were used for disease testing as described in Examples 1 and/or 2. Experiments were performed to screen for DM resistance on a collection of elite lines that show horticulturally acceptable plant and fruit types, and should have the DM resistance introgressed from PI197088. These tests were performed in three locations (Woodland, Calif., Tifton, Ga., and Wageningen, NL) and used two isolates of *Pseudoperonospora cubensis*: an "older" isolate, pathogenic on squash and cucumber, and the putative "new" isolate, not considered pathogenic on squash but very virulent on cucumber. Simultaneously, these samples were genotyped with molecular markers to identify a QTL contributing DM resistance in PI197088 (see also Example 4). These tests associate the DM pathology response with the presence of an allele from PI197088. During this time, breeders submitting the samples assembled all trial data available on these lines in which plant and fruit types are noted or quantified. The following lines shown in Tables 9-10 were screened for resistance to Downy Mildew.

TABLE 9

Pedigrees for Cucumber Lines listed in U.S. Patent Application Publication 2009-0265083, for which a Seed Deposit was Made.

| Cucumber Line | Pedigree |
| --- | --- |
| ASL147-2027 | PI-197088-MO/ASL-1105-GY:@.1.1.1.1.4. |
| EUR154-1012GY | [(ALCOR(WMV) × VENTURA × PIDM/NIZ335 * 2) × (ALCOR(V) × VENTURA × PIDM/CARMEN * 2)] × [(ALCOR(V) × VENTURA × PIDM/CARMEN * 2) × (ALCOR(V) × VENTURA × PIDM/CARMEN * 2)] |
| EUR154-1021GY | (ALCOR(WMV) × VENTURA × PIDM/NIZ335 * 2) × (ALCOR(V) × VENTURA × PIDM/CARMEN * 2) |
| GSP33-1094GY | F9-(Jazz/5/Sal//SMR-58Nim/PiHoNi/3/NO-50/4/H-171wit/ SMR-58Nim//Carol/3/NO-50 * Harmonie) |
| GPN33-1093GY | F8-(Jazz/5/Sal//SMR-58Nim/PiHoNi/3/NO-50/4/H-171wit/ SMR-58Nim//Carol/3/NO-50) |
| 03/8020-20_TUP03_DMFL_1 | BA.KO {(147W * PI) * 225)} * (BA MO * part) BC403/ 8020-20_TUP03_DMFL_1 + ---1_TUNE03_DM-2_TUp05_TKFA06 |
| 03/8024-19_TUP03_DMFL_1 | BA.KO {(147W * PI) * 225)} * [(me/n * 147wmv)bc4f5 * (bamo * parth)bc4f5] 03/8024-19_TUP03_DMFL_1 + ---4_TUNE03_DM-1_TUp05_TKFA06 |
| 03/8039-5_TUP03_DMFL_1 | BA.KO {(147W * PI) * 225)} * HP 159] * [(BA MO * part) BC403/8039-5_TUP03_DMFL_1 + ---3_ TUNE03_DM-4_TUp05_TKFA06 |

TABLE 10

Marker haplotypes and associated Downy Mildew (DM) reaction scores for five markers in the DM resistance QTL region. Data represent thirty seven cucumber lines.

| Marker | cM[1] position | Hap[2]. 1 | Hap. 2 | Hap. 3 | Hap. 4 | Hap. 5 |
|---|---|---|---|---|---|---|
| Markers and sample haplotypes ||||||| 
| CAPs_ENK60 | 4 | SUS[3] | SUS | RES[4] | RES | RES |
| CAPs_ENK59 | 5 | SUS | SUS | RES | RES | RES |
| CAPs_17170 | 11 | SUS | SUS | SUS | SUS | RES |
| CAPs_17179 | 11 | SUS | SUS | SUS | SUS | RES |
| CAPs_17563/66 | 39 | SUS | RES | SUS | RES | RES |
| Downy Mildew summary statistics associated with marker haplotypes |||||||
| Mean (DM[5]) | | 4.8 | 4.5 | 4.0 | 2.2 | 3.3 |
| Minimum (DM) | | 4.3 | 3.3 | 3.7 | 1.0 | 1.0 |
| Maximum (DM) | | 5.0 | 5.0 | 4.3 | 3.3 | 5.0 |
| Std. Deviation (DM) | | 0.2 | 0.6 | 0.3 | 0.5 | 1.2 |
| Number of lines with haplotype | | 3 | 3 | 1 | 19 | 11 |

[1]cM = centiMorgans.
[2]Hap = Haplotype at five markers in DM QTL.
[3]SUS = Downy Mildew susceptible allele associated with Lucinde parent in mapping population.
[4]RES = Downy Mildew resistance allele associated with PI197088 parent in mapping population.
[5]DM = phenotypic scores in a pathology test for Downy Mildew.

Thirty seven cucumber lines were tested for reactions to *Pseudoperonospora cubensis* in a controlled pathology screen. Eighteen plants were tested in three replicates of six plants. From each replication, three plants (total from three replications=9) were genotyped for five markers defining the DM QTL region. From these data, consensus marker genotypes and DM summary statistics were developed for each line. These data are summarized in Table 10. The five markers used in this test were selected from the eight linked markers in the DM QTL. The five markers were selected based on reliable performance in the laboratory, and/or associations with DM phenotype that were more consistent than the other markers.

Table 10 supports association of the haplotype RES-RES-SUS-SUS-RES at the markers CAPs_ENK60, CAPs_ENK59, CAPs__17170, CAPs__17179, CAPs__17563/66 with a more DM resistant phenotype. Substitution of the SUS allele with the RES allele at markers CAPs_ENK60, CAPs_ENK59, CAPs__17563/66 yields a change in mean DM phenotype from 4.8 to 2.2 in tests where the rating scale is 1=resistant and 5=susceptible.

Example 4

Marker Analysis of DM Resistant Cucumber Plants

Figure 2:
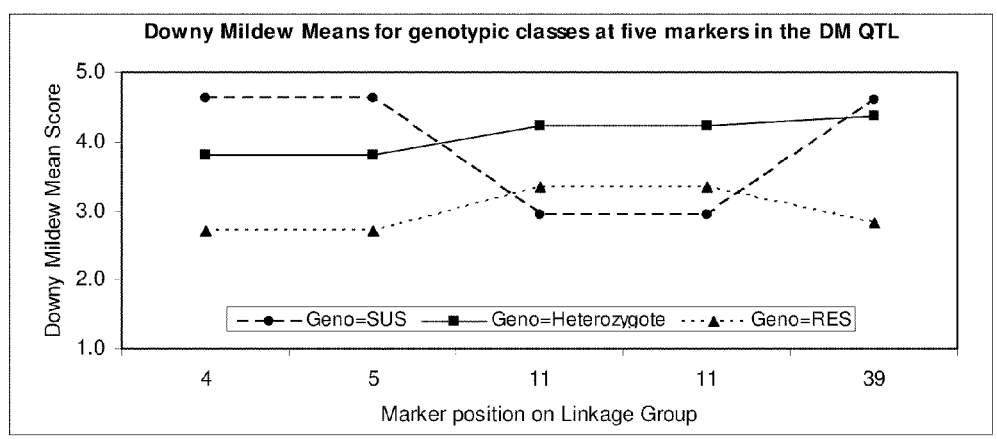
FIG. 2 depicts Downy Mildew resistance data for certain additional markers in an identified Downy Mildew resistance contributing QTL region, showing correlation between DM resistance and marker position.

Resistant plants are analyzed using genetic markers distributed throughout the cucumber genome. Genetic markers for *Cucumis* are available from a variety of sources such as USDA-ARS (Vegetable Crops Research Unit—Department of Horticulture, University of Wisconsin-Madison). A larger set of markers was pre-screened on the parental lines and polymorphic markers were selected, from among the pre-screened markers, for a subsequent screen. A correlation was then established with most of the resistant plants and the presence of specific donor alleles, for instance as shown in Table 10 and FIG. 2. Most of the resistant plants contained introgressed DNA from the resistant donor line, PI19788, for instance at loci as shown in FIG. 2. A multiple regression model was constructed to retain the markers that contributed to the DM resistance phenotype. In this analysis, markers CAPs_ENK60, CAPs__17170, and CAPs__17563/66 remained significant, generating a model with $R^2$ of 0.47.

Primer pairs and reaction conditions utilized to identify alleles at given markers on chromosome 5, to define the QTL for DM resistance in *Cucumis* sp., are shown in Table 11 and Table 12. For marker 17179, the same reverse primer was used for the two alleles.

TABLE 11

Primer pairs used (SEQ ID Nos: 1 to 19) to identify alleles of QTL on chromosome 5.

| Marker name | Forward Primer (5' to 3') | Reverse Primer (5' to 3') | Enzyme | Electrophoresis condition | Notes |
|---|---|---|---|---|---|
| CAPs_21826 | TCAAGCCATAGTCTAACCCATGC | CGCTATATCATGGATGGCTAGAAAT | NsiI | 3% agarose gel | |
| CAPs_ENK60 | GAATAGATAGGCTACACTTTTCCCTCTTG | GTATAAAACTTGAGTGAATTTAATGCATGAA | HpyC H4 IV | 3% agarose gel | |
| CAPs_ENK59 | TGTTTCATAACTACAGCTTCATGTTAAATATTACT | TAGTTTCTTTCTTGCTGGACGAACC | | 3% agarose gel | |
| CAPs_17170 | TATGGGCTATGTGAAACTCTT | AGCGTGACAACTACAAAACAT | Afl III | 3% agarose gel | |
| CAPs_17179 | GAAATAAATGGATGAAGCGAGGA | GTTCGTTGATCAGTGTGATATTTCAAT | | Capillary | Forward primer for PI197088 allele |
| CAPs_17179 | ATCGGTCTTTGCCACCTTTTG | GTTCGTTGATCAGTGTGATATTTCAAT | | Capillary | Forward primer for Lucinde allele |

TABLE 11-continued

Primer pairs used (SEQ ID Nos: 1 to 19)
to identify alleles of QTL on chromosome 5.

| Marker name | Forward Primer (5' to 3') | Reverse Primer (5' to 3') | Enzyme | Electrophoresis condition | Notes |
|---|---|---|---|---|---|
| CAPs_18229 | TGTTTGGAAGGGTTT CTTGGG | TGCCATGTCGCCAACAGT | HindIII | 3% agarose gel | |
| CAPs_17563/66 | AGGAGGGACAGAGA GAATTTGATATAAT | TCCGTTTTAGGTGATTGT CAAATACAT | | Capillary | |
| CAPs_ENK70 | AAAGTTGATAGTGCA TGAGTTGGTAAAATA | TCCGCTTATGGGTTTTTG TGAG | Taq1 | 3% agarose gel | |
| UBC12-1200 | TATGGGCTATGTGAA ACTCTT | AGCGTGACAACTACAAAA CAT | | | |

TABLE 12

Reaction conditions for PCR.

| Component | Combine per 10 ul rxn | Master Mix for 10: |
|---|---|---|
| PCR for: Markers run on agarose gel (CAPs_ENK60, CAPs_ENK59, CAPs_17170, CAPs_18229, CAPs_21826, CAPs_ENK70) | | |
| HOTSTART-IT Taq Master Mix (2X) | 5 | 50 |
| 5 uM Forward Primer | 0.53 | 5.3 |
| 5 uM Reverse Primer | 0.53 | 5.3 |
| MQ H$_2$O | 3.14 | 31.4 |
| Template DNA | 0.8 | 8 |
| Sum | 10 | 100 |
| PCR for: CAPs_17179 | | |
| HOTSTART-IT Taq Master Mix (2X) | 5 | 50 |
| 5 uM Primer 1 | 0.53 | 5.3 |
| 5 uM Primer 2 | 0.53 | 5.3 |
| 5 uM Tailed Primer | 0.053 | 0.53 |
| Labeled primer 1475 | 0.53 | 5.3 |
| MQ H$_2$O | 2.557 | 25.57 |
| Template DNA | 0.8 | 8 |
| Sum | 10 | 100 |
| PCR for: CAPs_17563/66 | | |
| HOTSTART-IT Taq Master Mix (2X) | 5 | 50 |
| 5 uM Primer | 0.53 | 5.3 |
| 5 uM Tailed Primer | 0.053 | 0.53 |
| Labeled primer 1475 | 0.53 | 5.3 |
| MQ H$_2$O | 3.087 | 30.87 |
| Template DNA | 0.8 | 8 |
| Sum | 10 | 100 |

Analysis for the genetic markers of Table 11 was performed by PCR amplification. PCR reactions were conducted as follows: PCR reactions contain 1.0 microliters of cucumber genomic DNA (10 ng), 2 µl 10× PCR Buffer (ABI PCR Buffer I: part no. N808-0006), 1.0 µl 10× dNTP mix (final concentration of each dNTP is 250 µM), 1 µl each primer (5 picomoles of each primer), 0.2 µl Taq Polymerase (1 unit), and sterile water to a total volume of 20 microliters. PCR reactions are incubated for 2 minutes at 94° C., 30 seconds at 94° C., 30 seconds at 50° C., and 90 seconds at 72° C. for 35 cycles, followed by a single cycle of 72° C. for 5 minutes. PCR reactions are performed for instance on an ABI9700 PCR machine (Applied Biosystems, Foster City, Calif.).

Sequencing of genomic DNA flanking the loci initially screened in the QTL region could explain some of the variability that was seen in some DM resistance scores. For instance, in certain lines with resistant haplotypes, but variable resistance scores, variability could be seen near the CAPs_17170 marker. Thus, when sequences for alleles at this locus were compared between two given lines with differing DM resistance scores, they may have matched at the position exploited for the marker assay, and so both could be defined as the same genotype. However, the sequences of such lines were found in some cases to differ for instance by up to 3 SNPs at sites near to but not exploited by the particular marker assay.

Genomic DNA sequences were obtained and utilized to design PCR primers for detecting single nucleotide polymorphisms, as markers to identify the presence of the QTLs. The genomic sequences flanking 50 SNP sites linked to QTLs 1, 2, or 4 on chromosomes 5, 4, and 2, respectively, are given in Table 13 (SEQ ID NOs:20-69). These sequences were used to design sets of 3 synthetic oligonucleotides for each marker, according to the GoldenGate® multiplex genotyping protocol (Illumina, Inc., San Diego, Calif., USA; e.g. see Fan et al., *Cold Spring Harbor Symp. Quant. Biol.* 68:69-78, 2003; and Gunderson et al., *Nature Genetics* 37:549-554, 2005). These sequences may also be used, as is known in the art, to design analogous assays, e.g. TAQMAN assays, for marker identification.

TABLE 13

*C. sativus* genomic DNA sequences flanking the
sites of SNP markers linked to QTLs 1, 2, or 4.

| Marker Name | Chromosome; map position | Genomic DNA Sequence (SEQ ID NOs: 20-69). SNP site with polymorphism is given within brackets. |
|---|---|---|
| NN0223782 | 2; 22.448 | TTCATACGCCGTTGCAGCTGAAAGTGGCAACCATTACTTCCAGATCATT ATGACAATAAA[T/C]AACCAAGGCCACCTTCATGCATAAATGGTAAGA TAATAGCAAGCTCTATACCTTCTTTTT |

TABLE 13-continued

*C. sativus* genomic DNA sequences flanking the
sites of SNP markers linked to QTLs 1, 2, or 4.

| Marker Name | Chromosome; map position | Genomic DNA Sequence (SEQ ID NOs: 20-69). SNP site with polymorphism is given within brackets. |
|---|---|---|
| NN0225385 | 2; 27.538 | TCTTGATCAATCCAACTGGGTTGGAACTCAAATTCAAGAAATGGGGTTT AATCACAACCA[T/C]GTTCAATCTCAATTTTCAGATTCCGCCATCCCC CCCACTCCCTATACTCAACCTCCTGAC |
| NN0226670 | 2; 30.115 | GGTTTAGATGAAAAGAAGTATGCATTCATGCTTTTGCACAAAGGCATTC CTGGCTTTCAA[A/C]TAGCTGTATCTCTTGCAGGGATATAAATGGATG CAACACTCTTTTCAGTGAAAGAAATCC |
| NN0224124 | 2; 32.406 | GGATCATTATTTATCCAACGTATTAGCAAGCTCTAATAGAAACACTTCC TAAAGAACATA[T/C]CGATCCAAATTATATGCTAAGAGAATTACCCAA CATTTGAGCAAGTTTACTGACTACAGC |
| NN0246472 | 2; 38.441 | TAGAAAACAAGAATGGTTCTCAAAGAACCTACCGACCGAATTGGTTGAG GATGAGATGAC[A/G]AATAGAAACATTAATAATATGGTGGAGGAGGAG GCGATCGATGAACCGTCGCAAAGCATT |
| NN0225358 | 2; 50.250 | CCACGAATGGAATCAATGAATTCACGAGCAACCTATAATAAGAGAGTGG AAAACAAAACT[A/G]CTCCTTCACCATCTAAGAAAACAATGTATAAAA ATCAGAGAAGGAAAGATAAAAGATACT |
| NN0227700 | 2; 55.622 | GAAGAAGAGTGCAACAAGTAAGAGTCTGGCTGGGGGAGTTGAAGTTCAT TCATGGATTAG[A/G]TTAACATACGAACTTTGGAGGCGTGCAAAAGAC AATCCCCATAACTTGATTACGGGCTTC |
| NN0224617 | 2; 57.989 | AAAATATATGATCCTACAACTAAATAAGAGTGCACATGAAGATACCTTA TATATAGGAGA[T/C]AATGATGTCGTATGTCCTGCTTGATGATTTCGA AGAACCAGATGACTGAAGAAGGAATAA |
| NN0247695 | 2; 66.466 | GGAGTTAATCGAAGGAAGAAAATCAACTCGTCTTAACAGCATCACAATA ATCAAATTCTT[T/C]AGGTATACCTTTCTTCTCCTTGTCACTGGACTC ATCAGGATCCTCATCGGCGATTTTGCG |
| NN0227242 | 2; 73.201 | CTCTGAAGAATTACCGAAGGGGGTCGGAATTTTCTCTATAGCCTGCAAT GAGAGGAATAA[T/C]GAGGAATGAAAATGTTGGCTCTGTAGCACATGA ATGAAATGCGGATATTCTGCCAAAGGC |
| NN0223824 | 2; 78.867 | AGAACAACCCCCAACGTCCCAAAATCACTACATCTCCAACCCTTTCTTC TCCTCATCATT[T/C]AGTTTTAGTCTCTGTTTTGTGGAACTCTCAAAT GAAATTGCTTGAATACTCTTGATAAAA |
| NN0223181 | 2; 82.411 | ACCAAAAATGAAATAAAATCAGGCTCCACCTTCACCTTGCAGTAATATG ATGGCAGTACG[T/C]TGCATTGTAAACCATGTTAATAGAAGAAAAGAA CTGTGAGAAAATACTAGAATTC |
| NN0226638 | 2; 88.353 | CGGATGAGGATTTCAGGTGTTTTTTCTAAACAAATGTTTGCCCTTTAAA CATGCGTTTGC[C/G]GATTCTGGTTTATTTGTTTTCGGTTGAT |
| NN0225012 | 4; 20.649 | ACTATCCTAATACTACGGAATTGGTGTGGAGAACAGAACAGTTATTTGG TTTGTTCGAAA[A/G]TCTCGACAACTTTCGATCGATCACTCTTGTTAG GGGGTATCCCAACTACATCATAAGCAA |
| NN0228579 | 4; 25.816 | ACTCATATTTACAGAAAACTTACTCTAAACCACAAGTCCTTAACAAATA TATTTCTGCTT[C/G]CGGCTCTCTTCCTATCATGAAATTTTGCAAGCT ATTCAGAAAATCC |
| NN0226451 | 4; 27.944 | TGCTTCTTGATCTTGCTAATGTAAAGAGATATCACTTACATGAAAGGCT TTCCGAGTCAT[T/C]GTCAATTTCTGCACTGGGAGGCTTTTGGTCATT GCTCTTGAATACCACATTCCCATATTT |
| NN0225088 | 4; 30.428 | GAGTTTCCAAAATTGAACATCTTCAATGGACAGAAAGTTTTGAAGTAGC AAGACTTAAGG[T/C]TTCCACTTGGTGTTCCTTATCTAAGTTCTCGAA CAATTTGCATTTGATTTCTTAAATATT |
| NN0226219 | 4; 32.977 | TAATAGTTACATGATGCTTTATTGCTACTATATATGTTCAGAAATATTA TCCAGATGCGA[A/T]ATATTTTCAGACACTGCTGTGAATGTTATTTGG ACTAACGAAACTTGTTATTTTGTGCTG |

TABLE 13-continued

*C. sativus* genomic DNA sequences flanking the sites of SNP markers linked to QTLs 1, 2, or 4.

| Marker Name | Chromosome; map position | Genomic DNA Sequence (SEQ ID NOs: 20-69). SNP site with polymorphism is given within brackets. |
|---|---|---|
| NN0247551 | 4; 35.460 | GTTTACATGAAAnTATGCACACACCCAAAGATATGTTGATTAAGATGAT AAGTTCCCAAG[A/G]ATAGAAGAATTATGTGTGTATTGCTTCTTTGAT GTCCAGGAACTAATGAGATTTATCTGG |
| NN0246357 | 4; 40.294 | TATAGCCGAGCAACCGAGTCCTTAGATTTGGTTTAAGAGCATCTACGAA TAGATGGTCGA[T/C]TGTATGAATGATGAGCAGAAACGCTCTTGAAAC GGCTTCnTCACATTTGAACTCCATGCA |
| NN0225551 | 4; 46.640 | TGATTTATCTCATGGAGAATACCAATGTGCAAAAGAAACCAAAGGCGTT CTTCTTCATCT[A/G]TGTTTAGCTTCGATATTGTGTGTAGCACTGCAN NNNNNNNNN |
| NN0226732 | 4; 49.999 | AGAAATTTTTTAAGACAATACTTGATATCCTTTTCACAATTCAGTTCAT TCCTCCTATAA[T/C]TGTGATTCCAGCAACGATTAGGAATGATTTCTC AATTCCCACCTTGGTGCACATTTCAAG |
| NN0247689 | 4; 51.938 | CTTTATTTTATTTTCAGGTTGCTCTTAAATTTGAGCACAGAAATAGTAA AGG[A/T]TGCAATTATGGTCCTCCATACGAATGGCAAGTTTACAAGTG AGTAACTTTTTGGGTTACA |
| NN0247342 | 4; 54.495 | GTACTTGTACCAATATGAAATGTGCACATGCGCTCTTGTCCTAGATAAT ATGCACAGTTC[A/T]CCTTAAAAGCTAAGCATAAGCCACAAATCCAAG AACCAATGTAACCAAAACAGTATGGGA |
| NN0224702 | 4; 62.385 | CTGTTGCCTATGCAAAGCATTTATACAGCTTCATTCTGCCATTTTAACG AATGTTCACTG[A/T]AGTACCTGAGATGGCTTCCAAAACTGTCTTGTA AGGTGTGCCTCTCATCTGCATCTGTCT |
| NN0225482 | 4; 66.478 | TCTTTTTATACTTTTCTGATCTTGTAAAGTTTAAGGCTTTCAACTGGTG TAGTGTAGTCA[A/C]CAGAAGTCTTTTTATAATTGTTACACTTTAATT TGATAGGAAAGTGTTTCTTTAA |
| NN0224538 | 4; 67.148 | GCTAGTATATCTATATATCTTTTTGAGAGCTTTATGATAATTATCAAAT GAAGATTCTAG[C/G]TGTGTGATCAAGAGAAGATTCCTAGCCTACCTC TTAGCTCTTTTAAAAATTGTGGTAGTT |
| NN0247543 | 4; 71.973 | TAAnTTTGTTTTCACATTTnTTTnCAAATAATATATATCTTACAGTTTA GGAGGCTTCTT[T/G]CACCATTACATATAAAACATATGGAACAAACAT TACCTCTAAATAACCAATAGACTTTTA |
| NN0224041 | 4; 75.834 | TCTTTAAAAGAAGCTTGAAAGATGAAGAAATTGCAAAATTTCAATCATT TCGATCCCTCC[A/T]CTCACCTGAAAAAGTGGTTAATTCTGATGATTT TAGATCATGGTCCATTGATCCCTCAAT |
| NN0228853 | 4; 78.923 | GTCCATACTACCATAATTGATAATACTAAGTACCCTGAACCTTTGAGAT TTGAATCTTTC[T/G]ACCCCACAGGTTGTTAAACACAAATACGAGTAA CAAAGATAAGATTTGAACTCAGCCTTT |
| NN0227762 | 4; 85.871 | TTGGTTCCTGATCCAGAAGAAAAATGGTTGATTTCCTTATGATTCTTTT CAGTAAGGTGG[A/G]ACAATCTTGCTCCAGGTCCTTCGTCATAAAACA CCCCCCTCCAAGGAAGAGAAACCCCAA |
| NN0227587 | 4; 87.395 | ATTTTTAGATGTGAGCCTATTTATGTGCTCTTAACTTCTCTTTTAGTAA TGGTGGAAATG[T/C]AATTTGTTTATGAGCAATGGTATCGTGAATAAA TGGTTGGATACATAATAGCTTTGCTTG |
| NN0228457 | 5; 25.235 | GTTGGGCTTTTTTGTTGTATTATTTCTTTTTGTCGTATTATGTATCTAA AGGCAGATGAA[A/G]ACCTGGATCATATTCTTTGGCAATGTGATTTTG CGTTGGTGTTTGGGATTCCTTTTTCCA |
| NN0246356 | 5; 30.032 | TTAAACAATTGACCCAAAAAnTTAAAGTTGATGGGTAAAGGTAAAACTAA CATTATATCAC[A/G]CAACATTCCCTCATTTGTAGACTTGAAATATGT AGAAAAGCCCATTAGTGAAAATGAATA |

TABLE 13-continued

*C. sativus* genomic DNA sequences flanking the
sites of SNP markers linked to QTLs 1, 2, or 4.

| Marker Name | Chromosome; map position | Genomic DNA Sequence (SEQ ID NOs: 20-69). SNP site with polymorphism is given within brackets. |
|---|---|---|
| NN0246332 | 5; 33.371 | TATTTTGGTGCTAACCGAATAGTTTGAGAGGGAGAAATAGGAAACGATG ACAACnCCATG[A/G]ATTGGGGGAAGTGTTCGACATTTGAAAAGGAGA ATAAATCAATTAAAATTATGCATTCAA |
| NN0223399 | 5; 38.201 | ACACAGTATTGATAATTTCCAAATCAACACTTGGAATATTTTGTTAAA TATGCACGACA[A/T]ATTTGGTTCGTTATTGGTCCATGATGGTAATCT ATACTTCATATGAAATTCTTATCTCTA |
| NN0223689 | 5; 41.014 | TATATGTTGCTAATGTGCTATTTTTAAAGAAAAAATAAAGGCCCCATTT GGTCATGGTTT[T/C]CTCTCAATTGTTCAATTGTACTTTCCACATTAT TTGAATAAGCAATCCAACTTTTACCTA |
| NN0247731 | 5; 44.780 | TGAAGAAGAGCCTTTATTGCGTCATCTGGAACCTCCTTTATCCATTTAT CTTGAATTGGT[T/C]GGTCATGAACACACCTTTACCATTTATTATTCA ATGCCATGATTGTCTTACACAGGTGTG |
| NN0226166 | 5; 49.540 | AGTCGAGTTTTGAGCCACTCATAACCCAGTTGAATGCTTTTAACCTTGT AGTCACTAACA[C/G]AAACACAGTGGAATGGTAGTTGAAGTAGGGTCA TTTTGGCTAATTCATTGCATGTTGTTA |
| NN0225480 | 5; 52.743 | TGTCCAAAAGAAATATATGCTCAAACTGTGCCTCAATCACCGTCTTCTC TCCAATTTTCC[T/C]ATATCATTCTCGATTATTACTTTCCTCTATTTC ATTTAGTTTCTAATAATTAATAACGGC |
| NN0246411 | 5; 55.649 | CCGAGGCGACCTCCGGCTTGCCCGTTACAAGTTGGGAGTTGGGCCTTGG GCTCTCGACGT[A/G]GGCCGAGAGTCCATTGCTCCTAAAGATTGGTGG GCACCGCGTnAGGCTGGTTCACAGAGC |
| NN0227759 | 5; 59.710 | CTTCTAGCCAAAATAATTCCATTTTTGTTTCACAAAATGAACCTGTTGG AGGGAAGACCA[C/G]TGCGCTACCCATCCCAAATTCAGATTCTGGAAA TATGGCCAAAGATCATTCATTGAGGTC |
| NN0247348 | 5; 61.450 | ATGGAGCTTAGAGAAAACGACCTAGAAAnTATTATCCTTATTCATGTCG AACGGGCTGTC[T/C]GGTAAGATTAGTTGAGGTGCGCATAATACCTGG ACACTCACAAATATGnnnnAAAAAAAn |
| NN0228465 | 5; 68.021 | ATATGGAATATTTGACAACTAATTAGTTACTTCTAAAACTGCAATAGCA GTCACGTTAGT[C/G]TCCCCCAGGGAGAGAAGAAAATACTAGAATTTG TGAGCCACTGTTAATAGATTCAAAATA |
| NN0247786 | 5; 71.424 | TTAGGTTCCCGCTATTGCAATACCAACAAGGCATGAAGGCTTT[C/G]G CCACAATGTGAAATCATCAACAGTTACTATGAACAATGAATTCGCTAAC AGGAAAnCGT |
| NN0226645 | 5; 74.784 | TCTAATTCGATGAGTTTGTCTGAATTCCCAAGTAAGAACCAAAGTTCCA TTCATTCTCTC[A/G]AGCACAAACCTTTCCACCAAAACATAACACCTA AATCTCTTCCACATTCCCTTTCCTTTA |
| NN0223809 | 5; 76.617 | GGAGATTGTTGCACGCCTGAAGAAAGCCTTCAGAATTACCATTAAGACT TCCCAACTCTG[T/C]CTGCATATTGTCAAGAAAGCTAGAGATTTTCTC AGAAGCTACTTTAATGGCAGGGCCCTC |
| NN0227071 | 5; 78.303 | AGGAAAATACCTTCCAATAGAAAACATGGTAAATGCAATAAGCATCTAG TTCATCCAATT[C/G]CAAGGGTAATGGCTAGTTCAAGATGGAACTAAA ACTCTCAGAGTGGTGTGTGCAATCCTG |
| NN0226870 | 5; 80.340 | GGTTACAGAGTCCAGAGCGATCAATGGAGATTGTGGATGTTGAAGGTTC AGAAGAGAAGG[A/G]TCGTTGATTAAGGAGGTCTTCATTCTCCAGGTG CTGAACGACAGTACCTTCCGGAATCTG |
| NN0228148 | 5; 82.273 | ATGATCCTCAATTCATACCATATTATTGTATGAGCTAAATGTGTATAAA GAAAAGGAAAG[T/C]TATAGAAGGATGGATTCGTACATTAACACAAAG GATAAAAACTGCAAACTTATTTATATA |

Plants containing a DM resistant donor allele(s), including lines GSP33-1094GY and GPN33-1093, among others (see Tables 1-8, and 14) were selected for further breeding. Depending on the breeding strategy, plants selected for further breeding can be either homozygous or heterozygous for a donor (resistant) allele.

TABLE 14

Line Descriptions- Selected Agronomic and Disease Resistance Traits for Additional Lines with Introgressed DM Resistance and Comparison Lines.

Lines with a high level of DM-resistance

| Line code | Seed Source | Type | Flowering pattern | Parthenocarpic | Plantbitterfree | CMV | Scab (*Cladosp. Cuc.*) | PM (*Sphaerotheca f.*) | DM (*Pseudop. Cu.*) |
|---|---|---|---|---|---|---|---|---|---|
| 05-346 | NJ05 854-3 | Pickling, parth. spined | GY | Yes | Yes | 1 | 1 | 2 | 2 |
| GSP33-1094GY | NJ05 696-4 | Pickling, parth. smooth | GY | Yes | No | 2.5 | 5 | 1 | 2 |
| 01-349 | VJ02 322-6 | Pickling, parth. spined | GY | Yes | Yes | 1.5 | 1 | 1 | 2 |
| GPN33-1093GY | VJ02 55-3 | Pickling, poll. spined | GY | No | No | 3 | 5 | 2 | 2 |

| Lines with a high level of DM-resistance | | Marker genotypes | | | | | | DM Mean score |
|---|---|---|---|---|---|---|---|---|
| Smooth/Spined | Spine color | CAPs_ENK59 | CAPs_ENK60 | CAPs_17179 | CAPs_17170 | CAPs_18229 | CAPs_17563/66 | |
| Spined | White | B | B | B | B | A | B | 1.8 |
| Smooth | xxxxx | B | B | A | A | A | B | 2.0 |
| Spined | White | B | B | B | B | A | B | 2.3 |
| Spined | White | B | B | A | A | A | B | 1.8 |

Lines susceptible to DM

| Line code | Seed Source | Type | Flowering pattern | Parthenocarpic | Plantbitterfree | CMV | Scab (*Cladosp. Cuc.*) | PM (*Sphaerotheca f.*) | DM (*Pseudop. Cu.*) |
|---|---|---|---|---|---|---|---|---|---|
| 05-110 | VJ05 110-3 | Pickling, parth. smooth | GY | Yes | Yes | 2 | 1 | 1 | 4 |
| 01-714 | NJ05 684-4 | Pickling, parth. smooth | GY | Yes | Yes | 2 | 1 | 2 | 4 |
| 05-779 | VJ05 273-4 | Riesenschal parth. | GY | Yes | Yes | 5 | 5 | 5 | 5 |

| Lines susceptible to DM | | Marker genotypes | | | | | | DM Mean |
|---|---|---|---|---|---|---|---|---|
| Smooth/Spined | Spine color | CAPs_ENK59 | CAPs_ENK60 | CAPs_17179 | CAPs_17170 | CAPs_18229 | CAPs_17563/66 | |
| Smooth | xxxxx | B | B | B | B | A | B | 3.6 |
| Smooth | xxxxx | B | B | B | B | A | B | 4.1 |
| Smooth | xxxxx | A | A | A | A | A | A | 5.0 |

Line 05-346 was found to display strong vigour, with dark green fruit color and cylindrical fruits with a length/thickness ratio of 3.2. Line GSP33-1094GY was found to display strong vigour, with fruits rather long (length/thickness ratio of 3.3/3.4), and leaves somewhat upright with little leaf tendency. The skin of the fruit was somewhat rough. Line 01-349 was found to be productive, with good fruit shape. Fruit flesh was firm, and fruits displayed an average length/thickness ratio of 3.3. Line GPN33-1093GY displayed strong vigour. Leaves were somewhat curled. Its fruits were slightly spined, but the density of spines was very low. The average length/thickness ratio of fruits was 3.3.

Example 5

Creation of Additional Populations for Mapping DM Resistance Loci

To identify loci underlying cucumber resistance to the Downy Mildew pathogen (*Pseudoperonospora cubensis*), two additional mapping populations were generated from crossing each of two susceptible parents (API-45-5312-MO and VJ03-68-06) by the same resistant line (PI197088). From each of these crosses a single $F_1$ plant was self pollinated to create two $F_2$ populations. These were coded as "API" and "VJ" populations, from the crosses API-45-5312-MO× PI197088 and VJ03-68-06×PI197088, respectively. Beginning at the $F_2$ generation, a single-seed descent procedure was used to create ~200 $F_5$ families in each of the two populations. The process involved self pollination of ~250 $F_2$ plants in each population to create $F_3$ families. From each $F_3$ family, a single plant was self pollinated to create $F_4$ families. From each $F_4$ family, a single plant was self pollinated to create $F_5$ families. When the $F_4$ plants were growing, tissue samples were collected from each plant. These samples were used for DNA isolation and marker genotyping. Multiple plants from each of the $F_5$ families derived from each $F_4$ plant were tested for reactions to *Pseudoperonospora cubensis* in replicated, multi-location pathology (i.e. disease resistance/susceptibility) trials (see Example 6).

Example 6

Analysis of Cucumber Plants in Additional Populations for DM Resistance

Marker genotypes for each $F_4$ plant from the mapping populations described in Example 5 were then analyzed against the performance of the $F_5$ progenies in DM disease resistance/susceptibility trials, in a parent genotype vs. progeny performance manner. Cucumber plants from these populations were grown in multiple locations including Turkey, Thailand, France, U.S.A., Netherlands, and India, and subjected to bioassays under greenhouse and/or field conditions, to determine the level of resistance to Downy Mildew disease caused by *P. cubensis*. Resistance tests performed in some locations utilized the protocols described above, in Examples 1-2. Resistance tests performed in Nimes, France and in Turkey utilized a similar protocol, however, for instance, a *P. cubensis* isolate found naturally at Bortepe, Antalya, Turkey was used, while tests in the Netherlands and in Thailand utilized *P. cubensis* isolates also obtained locally. Tests were performed on the mapping populations with a panel of cultivars selected from the group including: SMR58, Maram and Corona (highly susceptible); Poinsett 76, Adefem (partially resistant); Sweetslice (intermediate resistant); and PI197088 (highest level of resistance) as controls. Inoculations were performed in the greenhouse using freshly sporulating detached leaves, about 6 days to 1 month after planting. Up to three evaluations of cotyledons and $1^{st}$ and $2^{nd}$ leaves were performed about 6-30 days after inoculation. An exemplary disease rating scale is defined as follows:

1: True leaves or cotyledons show no symptoms.
2: Leaves or cotyledons are green, possibly a few chlorotic spots.
3: Necrotic spots are not confluent; less than 30% of cotyledon area is affected; leaves have larger chlorotic spots with necrosis at center.
4: 40% of cotyledon area is necrotic; less than 25% of leaf area is necrotic.
5: 50% of cotyledon area is necrotic; less than 50% of leaf area is necrotic, not coalescent.
6: 60% of cotyledon area is necrotic; coalescent necrotic area on 25% of leaf surface.
7: 70% of cotyledon area is necrotic; coalescent necrotic areas cover 50% of leaf surface.
8: On cotyledons and leaves, only tissue near petiole is still green.
9: cotyledons and leaves are completely necrotic.

Figure 3:
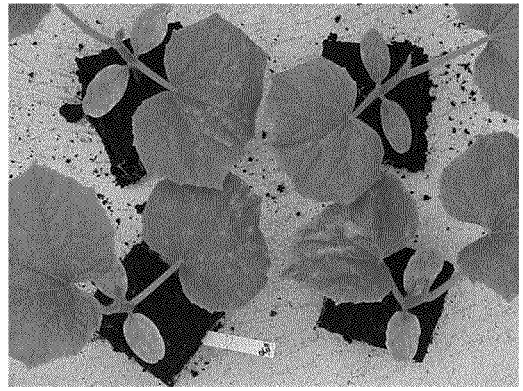
FIG. 3 depicts typical disease reactions for (A) PI197088; (B) cv. Adefem; and (C) cv. Maram.
Figure 3:
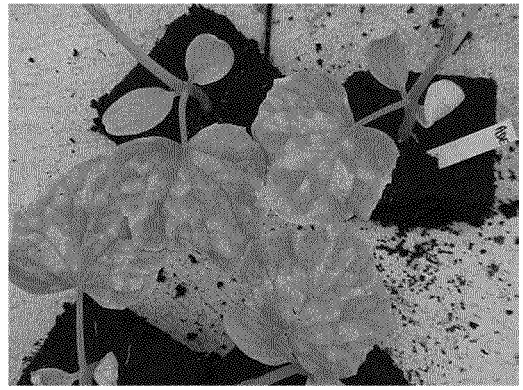
Figure 3:
Figure 4:
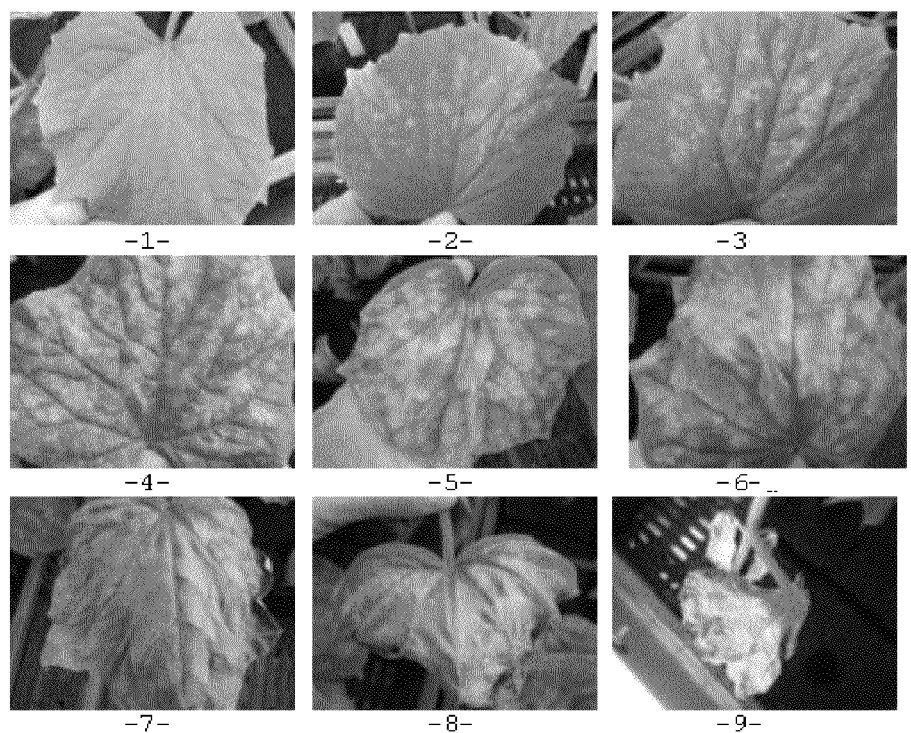
FIG. 4 depicts typical disease reactions on mature leaves which represent the disease rating scale outlined in Example 6, where "1" is most resistant and "9" is most susceptible.

Representative levels of disease on control lines and in a mapping population are shown in FIGS. 3-4.

Example 7

Methods for QTL Mapping Analysis of API and VJ Plant Populations

Figure 5:
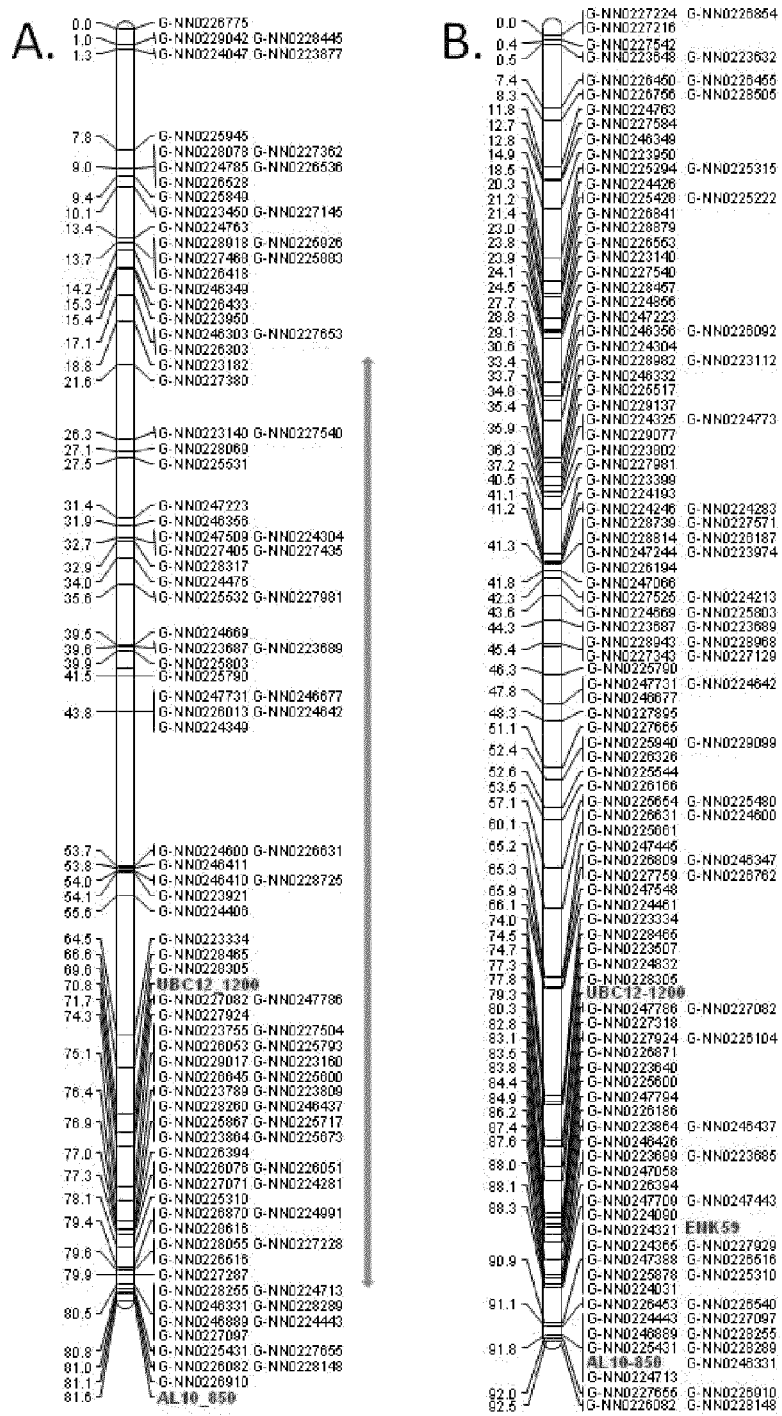
FIG. 5 depicts genetic maps of cucumber chromosomes 5, 4, and 2 with numerous SNP markers ("NNO . . . ") as well as previously utilized RAPD or CAPS markers such as CAPS_ENK59. The number on the left of each schematic chromosome represents genetic distance in cM from the "top" of the map. The marker locations are given on the right of each diagram. The thick two-sided arrows to the right of the designated markers represent the approximate location of QTL 1, 2, and 4. (A) Chromosome 5 from the API mapping population; (B) Chromosome 5 from the VJ mapping population; (C) Chromosome 4 from the API mapping population; (D) Chromosome 4 from the VJ mapping population; (E) Chromosome 2 from the API mapping population; (F) Chromosome 2 from the VJ mapping population.
Figure 5:
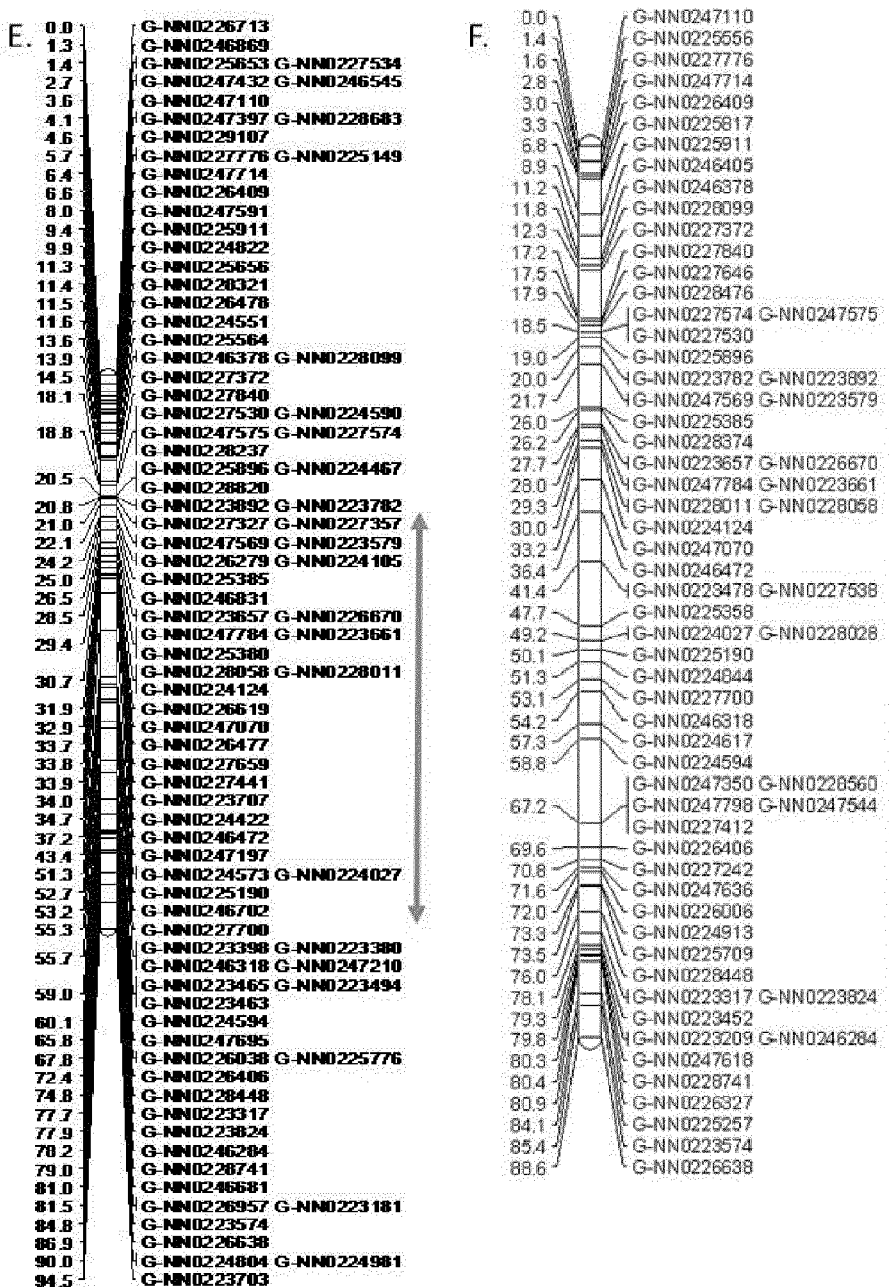

QTL mapping analysis was performed on the data obtained from disease tests on the two additional mapping populations derived from crosses with PI190788. For the API population, 971 mapped SNP markers across 174 genotyped and phenotyped lines were utilized. For the VJ population, 964 mapped SNP markers across 168 genotyped and phenotyped lines were used. Exemplary genetic markers are listed in Table 13, and FIG. 5 schematically illustrates the positions of these markers which localize to chromosomes 5, 4, and 2. QTL-mapping analyses were performed in QTL Cartographer v1.17 (Basten et al., 1994; and Basten et al., 2004). The programs used were: LRmapqtl, SRmapqtl, MImapqtl, MultiRegress, JZmapqtl. All two populations×6 locations (=12 datasets) were analyzed independently.

Interval mapping was performed at 1 cM intervals using LRmapqtl. The parameters used for the program were: M=3; d=1; c=0; r=0. Stepwise Regression Mapping with forward-selection followed by backward-elimination was performed using SRmapqtl. Markers were included in the model at P<0.001 at the forward-selection step and excluded from the model at P>0.001 for the backward-elimination step. Markers within 10 cM of markers already in the model were excluded from further analysis. The parameters used for the program were: M=2; F=0.001; B=0.001; u=10.

Multiple Interval Mapping was used to search for multiple QTL in multiple intervals. JZmapqtl was first used to estimate genotype frequencies at 1 cM intervals. The parameters used for the program were: I=30; M=9; d=1. MultiRegress was then used to estimate the initial set of putative QTLs using stepwise regression testing for all 1 cM intervals for both additive and dominance effects and a QTL is included in the initial model at P<0.0001. Test sites within 20 cM of a putative QTL already included into the model are excluded from further analysis. The parameters used for the program were: c=0; S=0.0001; w=10; u=20; I=30. MImapqtl was used to test and eliminate non-significant putative QTLs from the initial model identified by MultiRegress (−I=sMPrTseC). At this step, the maximum number of QTL is limited to 5 (−q=5), and a putative QTL is deleted if the change in information criterion is <13.825 (corresponding to 3 LOD). MImapqtl was then used to refine the QTL position (−I=sMPRtseC), and search for any new QTL (−I=sMPrtSeC). At this step, the maximum number of QTLs was limited to 5 (q=5), and a putative QTL would be added if the change in information criterion is >13.825 (corresponding to 3 LOD). A search for epistatic interactions between putative QTLs (I=sMPrtsEC) was also carried out. At this step, an epistatic term would be included in the model if the change in information criterion were >0.000. All other analyses including analyses of QTL Cartographer results were performed using R (R Development Core Team, R: A Language and Environment for Statistical Computing. R Foundation for Statistical Computing, Vienna, 2009). For the assessment of the modes, disease ~QTL1+QTL2+QTL4.

Example 8

QTL Mapping Results for API and VJ Populations

A total of 23 apparent QTL intervals (2-LOD interval 5 LOD QTL peaks) were identified across the 2 population×6 location experiments. Many of these overlap between populations and/or locations, and three QTLs, termed QTL 1, QTL 2, and QTL 4, mapping to chromosomes 5, 4, and 2 respectively, were identified for further analysis. Markers utilized, along with their positions, are given in Table 13, and approximate map positions for the QTLs are also given in Table 15.

Of particular interest are QTL 1 on chromosome 5 and QTL 2 on chromosome 4, which were identified in both mapping populations grown in at least three of the six geographic locations, suggesting the robustness of these two QTLs in different genetic backgrounds and environmental conditions. The average individual additive allelic effects are 0.62 (0.32-1.26) at QTL 1 and 0.62 (0.47-0.93) at QTL2. Therefore, an individual plant with both resistant alleles at both QTLs is likely to have a reduction in disease rating of 0.62×2+0.62×2=2.48. Individually, the average amount of phenotypic variation explained by each of these two QTLs is 24% (QTL 1) and 21% (QTL 2), with the remaining 76%-79% attributable to other genetic effects and environmental (non-genetic) effects.

A negative additive effect (i.e. a resistant genotype with higher disease score) was identified at chromosome 2, position 21.8-73.8cM in the VJ population grown in Turkey, corresponding to QTL 4. The same QTL was also identified in this same VJ population grown in Nimes and Thailand, but the additive effect was positive. Thus, the negative additive effect identified in the Turkey dataset is likely not an artifact but rather suggests the presence of genotype×environmental effects.

TABLE 15

Summary of interval mapping results for two mapping populations across 6 locations.

| QTL # | Chr | Approx. Interval (cM) | Mapping Population | Number of Locations | Additive Effects | $R^2$ |
|---|---|---|---|---|---|---|
| 1 | 5 | 22.6-81.0 (58.4) | Both | 6 | 0.32-1.27 | 12-39% |
| 2 | 4 | 37.7-87.6 (49.9) | Both | 3 | 0.47-0.93 | 13-28% |
| 4 | 2 | 21.8-73.8 (52.0) | VJ | 3 | −0.49-0.61 | 12-20% |

QTL intervals shown in Table 15 were identified by Interval Mapping. Each interval is labeled by a unique identifier (QTL #) with chromosomal location on a consensus cucumber genetic map (e.g. Ren et al., 2009) indicated. QTL intervals may be identified in one or both of the API and VJ mapping populations and in one to six of the six geographic locations where testing was done. The range of additive allelic effects and proportion of phenotypic variation attributable to the corresponding QTL ($R^2$) are also indicated.

Exemplary SNP markers corresponding to three QTLs (termed QTLs 1, 2, and 4) which were identified are listed in Table 13. These QTLs map, respectively, to chromosomes 5, 4, and 2. Of 23 putative QTL intervals identified by the interval mapping approach, examples of which are shown in Table 16 and 21, were also identified by a stepwise regression approach using forward-selection-backward elimination. The two putative QTLs which did not corroborate did not correspond to either QTL 2 on chromosome 4 or QTL 1 on chromosome 5.

in most (5/6) of the locations (Table 17), suggesting this QTL interval is robust in view of both genetic backgrounds and environmental differences. Conversely, QTL 2 was identified in the API population grown in three of the locations and in the VJ mapping population grown in Turkey (Table 17), suggesting that the effect of this QTL may be dependent on the genetic background.

In contrast to QTL 2, QTL 4 on chromosome 2 was identified from the VJ population grown in three of the six locations and in the API population grown only in Turkey. This suggests that while QTL 2 may be specific to the API background, QTL 4 may be specific to the VJ background. Interestingly the allelic effect of QTL 4 becomes negative when QTL 2 is also in the model (in both mapping populations grown in Turkey), possibly suggesting (1) an opposing effect between QTL 2 and QTL 4, or (2) that the negative effect at QTL 4 is specific to environmental conditions found at the testing site in Turkey. Assessment of the model: disease ~QTL1+QTL2+QTL4 for the other datasets suggests all three QTLs should have positive additive effects (also see Table 18), implying the second explanation is more likely.

Epistatic interactions were only identified in the two Turkey datasets and only additive-by-additive effects were identified. The interactions were between the major QTL intervals QTL1, QTL2, and QTL4. Because epistatic interaction is only identified in the Turkey data and because of the negative effect of QTL4 in these dataset, at this point, it is unclear whether the negative additive×additive effects between QTL1 and QTL2 is also Turkey-specific.

TABLE 16

QTLs identified by Multiple Interval Mapping for the two mapping populations grown in six locations.

| Population | Dataset | Location | QTL1 | QTL2 | QTL4 | QTL1 × QTL2 | QTL2 × QTL4 | $R^2$ |
|---|---|---|---|---|---|---|---|---|
| VJ | 1 | Turkey | 0.61 | 0.47 | −0.46 | −0.23 | | 0.67 |
| | 2 | Nimes | 0.58 | | 0.36 | | | 0.52 |
| | 3 | Thailand | 0.59 | | 0.65 | | | 0.29 |
| | 4 | Netherlands | | | | | | 0.16 |
| | 5 | India | 0.47 | | | | | 0.36 |
| | 6 | Felda | 1.28 | | | | | 0.33 |
| API | 7 | Turkey | 0.47 | 0.57 | −0.45 | −0.22 | 0.23 | 0.56 |
| | 8 | Nimes | 0.69 | 0.49 | | | | 0.66 |
| | 9 | Thailand | 0.74 | 0.90 | | | | 0.47 |
| | 10 | Netherlands | 0.32 | | | | | 0.15 |
| | 11 | India | 0.52 | | | | | 0.32 |
| | 12 | Felda | | | | | | — |

To estimate the joint effects of multiple QTLs at multiple intervals, multiple interval mapping was performed for all datasets. The results again identified QTL 1 (mapping to chromosome 5) and QTL 2 (mapping to chromosome 4). QTL 1 was identified in both the API and VJ locations grown Among a total of eight unique QTL intervals identified by at least one of the experiments, QTLs 1, 2, and 4 are shown in Tables 16-17, and their corresponding genetic locations are indicated in Table 15. In Table 16, the last column, $R^2$, is the estimated proportion of observed phenotypic variation explained by the genetic model. For datasets 2, 4, 5, and 8 of Table 16, minor putative QTLs were included in the analysis of the proportion of observed variation explained by the QTLs (column) in the model of the experiment (row) and the numeric values are the estimated additive allelic effects (additive×additive in the case of QTL1×QTL2, or QTL2× QTL4).

Genomic sequences from cucumber DNA clones containing RAPD Genetic marker CAPS_ENK59, among others, such as was used to identify the DM-resistance QTL described in Example 3, Tables 10-11, and FIG. 1, were aligned to a cucumber genomic map to determine their locations within the cucumber genome. Sequences were aligned using SEQUENCHER (Gene Codes Corp., Ann Arbor, Mich., USA), and found to fall within 13 contigs (11 loci completely assembled, and 1 locus assembled onto two contigs). These sequences were then aligned onto a cucumber genomic physical sequence scaffold map using BLAST and GMAP (Genentech, South San Francisco, Calif., USA), with the RAPD marker positions (converted to CAPS) being placed on the integrated physical-genetic map based on sequence similarity. Additionally, the CAPS_ENK59, UBC12-1200, and AL10-850 markers, which were found to be linked with the originally defined QTL in the previous mapping experiments based on QTL analysis of lines derived from a Lucinde×PI197088 cross as described in Example 3, were also followed in the new API and VJ mapping populations to determine where they localized relative to the newly identified QTLs. Both approaches resulted in the finding that the originally identified QTL of Example 3 co-localizes with QTL 1 and maps to chromosome 5, as shown in FIG. 5. Marker NN0246677 maps around position 43.8 or 47.8 respectively, of the respective API- and VJ-derived chromosome maps of FIG. 5, well within the genetically defined QTL. Although this is some genetic distance from CAPS_ENK59 which was utilized in the initial work, the markers identified as co-segregating with this QTL (i.e. QTL 1) were identified in different mapping populations, and in particular, the initial work genotyped fewer markers and had fewer replications of phenotyping trials than were utilized subsequently with the SNP markers such as NN0246677. Thus, the original mapping population included fewer recombination events, allowing for more distant markers to be more frequently retained in a linkage block that showed significant association with a DM-resistance QTL. The QTL analyses in different populations had different levels of statistical significance as well, resulting in somewhat different map positions.

Additional putative QTLs specific to various combinations of mapping population and geographic location were also identified, but the lack of replication across location and/or mapping population potentially suggest these QTL contribute too little to the overall phenotypic variation for replicable detection.

A summary of the interval mapping results is shown in Table 17, with 2 LOD intervals at 4-LOD QTL peaks for each of the 2 population×6 location experiments. Chr: chromosome; From: left position of the 2-LOD interval in cM; To: right position of the 2-LOD interval in cM; LR: likelihood ratio between the alternate (H3) and null (H0) hypotheses, where H3=presence of a QTL with additive and dominant allelic effects at the test site and H0=no QTL at test site); a: additive allelic effect; d: dominant allelic effect; $R^2$: proportion of variation explained by the putative QTL at the test site, SR: whether the same QTL was detected by the Stepwise Regression approach; MIM: whether the putative QTL was detected by the Multiple Interval Mapping approach.

TABLE 17

Interval mapping results.

| Population | Location | Chr | From | To | LR | a | d | $R^2$ | SR | MIM |
|---|---|---|---|---|---|---|---|---|---|---|
| VJ | Nimes | 2 | 21.77 | 66.48 | 21.53 | 0.41 | 0.23 | 0.12 | Y | Y |
| VJ | Turkey | 2 | 39.45 | 48.76 | 36.46 | −0.48 | 0.14 | 0.20 | Y | Y |
| VJ | Thailand | 2 | 46.76 | 73.80 | 28.79 | 0.61 | −0.58 | 0.16 | Y | Y |
| VJ | Turkey | 4 | 37.65 | 73.98 | 32.79 | 0.47 | −0.02 | 0.18 | Y | Y |
| API | Nimes | 4 | 46.65 | 71.65 | 38.00 | 0.56 | 0.18 | 0.22 | Y | Y |
| API | Turkey | 4 | 55.82 | 79.93 | 43.23 | 0.53 | −0.27 | 0.22 | Y | Y |
| VJ | Thailand | 4 | 57.50 | 87.57 | 21.85 | 0.58 | −0.08 | 0.13 | Y | — |
| API | Thailand | 4 | 74.98 | 81.98 | 51.79 | 0.93 | 0.25 | 0.28 | Y | Y |
| API | Turkey | 5 | 22.58 | 56.40 | 27.88 | 0.43 | −0.42 | 0.16 | Y | Y |
| API | India | 5 | 26.64 | 30.31 | 59.67 | 0.52 | 0.15 | 0.32 | Y | Y |
| API | Netherlands | 5 | 33.84 | 77.66 | 24.21 | 0.32 | −0.13 | 0.15 | Y | Y |
| VJ | Thailand | 5 | 40.37 | 55.81 | 20.24 | 0.55 | 0.22 | 0.12 | Y | Y |
| API | Thailand | 5 | 44.71 | 56.40 | 34.46 | 0.79 | 0.55 | 0.22 | Y | Y |
| API | Nimes | 5 | 44.71 | 55.40 | 70.72 | 0.71 | 0.04 | 0.39 | Y | Y |
| VJ | Nimes | 5 | 46.19 | 55.81 | 45.75 | 0.61 | 0.13 | 0.25 | Y | Y |
| VJ | Turkey | 5 | 53.10 | 80.70 | 51.56 | 0.57 | 0.29 | 0.27 | Y | Y |
| VJ | India | 5 | 53.10 | 80.95 | 35.43 | 0.45 | 0.13 | 0.19 | Y | Y |
| VJ | Felda | 5 | 76.71 | 80.95 | 58.81 | 1.26 | 0.48 | 0.33 | Y | Y |

Linear Regression was also utilized to calculate coefficients of disease explained by the model QTL1+QTL2+QTL4 (see Table 18). Unlike QTL Cartographer, which always compares the change in phenotype against the resistant line, the coefficient values of Table 19 correspond directly to the change in disease rating from 1 (resistant) to 9 (susceptible). Thus a positive coefficient implies an increase in susceptibility.

TABLE 18

Coefficients of disease obtained using linear regression.

| Population | Location | Intercept | QTL1 | QTL2 | QTL4 |
|---|---|---|---|---|---|
| VJ | Turkey | 8.6 | −0.56 | −0.41 | 0.45 |
| VJ | Thailand | 8.8 | −0.28 | −0.51 | −0.46 |
| VJ | Nimes | 8.9 | −0.51 | −0.29 | −0.39 |
| VJ | Netherlands | 6.3 | −0.12 | −0.03 | −0.05 |
| VJ | India | 9.6 | −0.44 | −0.15 | −0.13 |
| VJ | Felda | 9.4 | −1.26 | −0.20 | −0.08 |
| API | Turkey | 8.1 | −0.40 | −0.54 | 0.40 |
| API | Thailand | 7.0 | −0.55 | −0.65 | 0.06 |
| API | Nimes | 6.9 | −0.54 | −0.37 | −0.01 |

TABLE 18-continued

Coefficients of disease obtained using linear regression.

| Population | Location | Intercept | QTL1 | QTL2 | QTL4 |
|---|---|---|---|---|---|
| API | Netherlands | 5.5 | −0.22 | 0.05 | −0.02 |
| API | India | 9.2 | −0.38 | −0.18 | 0.09 |
| API | Felda | 6.6 | −0.05 | −0.54 | 0.31 |

Example 9

Alignment of SNP Markers to SSR-Based Cucumber Genetic Map

For mapping of QTLs relative to additional markers, the SNP markers of Table 13 were aligned with SSR markers which were used by Ren et al. (PLoS ONE 4:e5795, 2009; doi:10.1371/journal.pone.0005795) by an informatics approach. First, the 16-25 bp primer sequences defining the SSR markers of Ren et al. were aligned with corresponding cucumber scaffold sequences (genomic fragments) using BLAST. Perfect alignments covering entire primer sequence pairs (i.e. both forward and reverse primers) were filtered to remove any apparent perfect alignments which did not suggest the forward and reverse primers properly facing each other, and the remaining scaffold positions were merged with the SSR-based map information. 574 SSR markers were putatively mapped to 591 scaffold genomic fragment sequences, since, as expected, some SSR sequences mapped to >1 scaffold location. Using a size difference threshold of less than or equal to 50 bp for the difference between the reported forward and reverse SSR primer locations and the mapped distance as indicated by the scaffold sequences, 550 SSR markers (with 566 mapped locations) were considered to be reliably mapped. This SSR data was then sorted with Scaffold IDs, and was merged with known positions of other available internal markers. Finally, inconsistent marker positions were noted, and remaining SSR genetic positions were anchored to a consensus genetic/physical map that had been built using SNP markers and genomic scaffold sequences. Table 19 lists map positions of SNP and SSR markers of chromosomes 2, 4, and 5, which may be directly compared with the genetic map of Ren et al. (2009). SSR and other public markers listed in bold in Table 19 map to the identified QTL regions, or are about 10 cM or less from such a region, and are expected to co-segregate with DM resistance. The mapping of SNP and SSR markers as listed in Table 19 allows for identification, using a publicly available genetic map, of additional (e.g. publicly available) genetic markers that map to a genomic region linked to Downy mildew resistance. In Table 19, the DM resistance QTL of chromosome 2 is defined as spanning the region defined by SNP marker NN0223892 (map position 22.3), to SNP marker NN0226638 (map position 88.4). The DM resistance QTL of chromosome 4 is defined as spanning the region defined by SNP marker NN0227442 (map position 20.6), to SNP marker NN0227285 (map position 87.4). The DM resistance QTL of chromosome 5 is defined as spanning the region defined by SNP marker NN0226553 (map position 25.3), to SNP marker NN0226391 (map position 82.1).

TABLE 19

Genetic map positions of SNP ("NN0 . . . ") and SSR markers of cucumber chromosomes 2, 4, and 5, from alignment of SSR markers onto consensus scaffold-based genetic map. See also FIG. 5.

| Marker Name | Chromosome # | Map position |
|---|---|---|
| NN0226713 | 2 | 0.0 |
| NN0246869 | 2 | 1.3 |
| NN0227534 | 2 | 1.5 |
| NN0228688 | 2 | 1.5 |
| NN0224222 | 2 | 1.6 |
| NN0225653 | 2 | 1.6 |
| NN0227319 | 2 | 1.6 |
| NN0247117 | 2 | 1.6 |
| NN0223201 | 2 | 1.6 |
| NN0246545 | 2 | 2.8 |
| NN0247432 | 2 | 2.8 |
| NN0225708 | 2 | 3.3 |
| NN0224023 | 2 | 3.3 |
| NN0225478 | 2 | 3.7 |
| NN0225481 | 2 | 3.7 |
| NN0247128 | 2 | 3.9 |
| NN0247110 | 2 | 4.2 |
| NN0228683 | 2 | 4.6 |
| NN0247397 | 2 | 4.6 |
| NN0229107 | 2 | 5.0 |
| SSR11952 | 2 | 5.9 |
| NN0227776 | 2 | 5.9 |
| NN0225556 | 2 | 5.9 |
| NN0225149 | 2 | 5.9 |
| NN0247714 | 2 | 6.9 |
| NN0226409 | 2 | 7.0 |
| NN0247374 | 2 | 7.0 |
| NN0225817 | 2 | 7.2 |
| SSR21090 | 2 | 7.5 |
| NN0228345 | 2 | 7.5 |
| NN0224358 | 2 | 8.1 |
| NN0224778 | 2 | 8.1 |
| NN0247591 | 2 | 8.8 |
| NN0246816 | 2 | 9.7 |
| NN0226190 | 2 | 10.2 |
| NN0225911 | 2 | 10.2 |
| NN0224313 | 2 | 10.5 |
| NN0224822 | 2 | 10.7 |
| NN0225831 | 2 | 12.1 |
| NN0224132 | 2 | 12.1 |
| NN0224585 | 2 | 12.2 |
| NN0224551 | 2 | 12.2 |
| NN0226478 | 2 | 12.2 |
| NN0226856 | 2 | 12.2 |
| NN0228321 | 2 | 12.2 |
| NN0225656 | 2 | 12.2 |
| NN0246405 | 2 | 12.3 |
| NN0247003 | 2 | 12.8 |
| NN0226751 | 2 | 12.8 |
| SSR00684 | 2 | 13.0 |
| NN0229051 | 2 | 13.0 |
| NN0247367 | 2 | 13.0 |
| SSR16226 | 2 | 14.2 |
| NN0225537 | 2 | 14.2 |
| SSR03070 | 2 | 14.2 |
| NN0225564 | 2 | 14.2 |
| NN0246551 | 2 | 14.5 |
| NN0224243 | 2 | 14.5 |
| SSR00204 | 2 | 14.5 |
| NN0223995 | 2 | 14.5 |
| NN0246378 | 2 | 14.6 |
| NN0228099 | 2 | 14.9 |
| NN0227372 | 2 | 15.5 |
| NN0246337 | 2 | 19.0 |
| SSR00289 | 2 | 19.7 |
| NN0227840 | 2 | 19.7 |
| NN0227646 | 2 | 20.0 |
| NN0228476 | 2 | 20.3 |
| NN0224590 | 2 | 20.8 |
| NN0228237 | 2 | 20.8 |
| NN0247575 | 2 | 20.8 |
| NN0227530 | 2 | 20.8 |
| NN0227574 | 2 | 20.8 |
| NN0224794 | 2 | 20.9 |

TABLE 19-continued

Genetic map positions of SNP ("NN0 . . . ") and SSR markers of cucumber chromosomes 2, 4, and 5, from alignment of SSR markers onto consensus scaffold-based genetic map. See also FIG. 5.

| Marker Name | Chromosome # | Map position |
|---|---|---|
| NN0224612 | 2 | 21.2 |
| NN0224686 | 2 | 21.2 |
| NN0224467 | 2 | 21.3 |
| NN0228820 | 2 | 21.3 |
| NN0225896 | 2 | 21.8 |
| NN0223892 | 2 | 22.4 |
| NN0223782 | 2 | 22.4 |
| NN0227357 | 2 | 22.7 |
| SSR22083 | 2 | 22.7 |
| NN0227327 | 2 | 22.7 |
| NN0247569 | 2 | 23.9 |
| NN0223579 | 2 | 23.9 |
| NN0226747 | 2 | 24.3 |
| SSR23832 | 2 | 24.9 |
| NN0226337 | 2 | 24.9 |
| NN0227615 | 2 | 25.4 |
| NN0226084 | 2 | 25.4 |
| SSR23220 | 2 | 25.4 |
| NN0226279 | 2 | 26.5 |
| NN0224105 | 2 | 26.5 |
| SSR23420 | 2 | 26.5 |
| NN0225385 | 2 | 27.5 |
| NN0246831 | 2 | 28.8 |
| NN0228374 | 2 | 28.8 |
| NN0223545 | 2 | 29.2 |
| NN0224897 | 2 | 29.2 |
| NN0226707 | 2 | 29.5 |
| NN0226670 | 2 | 30.1 |
| SSR01374 | 2 | 30.1 |
| SSR22338 | 2 | 30.1 |
| NN0223657 | 2 | 30.1 |
| NN0247784 | 2 | 30.7 |
| NN0225380 | 2 | 30.7 |
| NN0223661 | 2 | 30.7 |
| NN0247123 | 2 | 30.7 |
| NN0228011 | 2 | 32.1 |
| NN0228058 | 2 | 32.1 |
| NN0224124 | 2 | 32.4 |
| NN0246849 | 2 | 33.5 |
| NN0226619 | 2 | 33.7 |
| NN0247070 | 2 | 34.7 |
| NN0226477 | 2 | 35.3 |
| NN0223707 | 2 | 35.5 |
| NN0227659 | 2 | 35.5 |
| NN0227441 | 2 | 35.5 |
| NN0223443 | 2 | 35.5 |
| NN0223203 | 2 | 35.5 |
| NN0226267 | 2 | 35.7 |
| NN0224422 | 2 | 36.1 |
| NN0227137 | 2 | 36.6 |
| NN0246472 | 2 | 38.4 |
| NN0224359 | 2 | 38.4 |
| NN0228139 | 2 | 38.7 |
| NN0227805 | 2 | 43.5 |
| NN0247413 | 2 | 43.5 |
| NN0223478 | 2 | 43.8 |
| SSR02569 | 2 | 43.8 |
| SSR07108 | 2 | 43.8 |
| NN0227538 | 2 | 43.8 |
| NN0247197 | 2 | 44.4 |
| SSR11512 | 2 | 44.4 |
| NN0226250 | 2 | 45.0 |
| NN0224063 | 2 | 45.3 |
| NN0228486 | 2 | 45.3 |
| NN0224233 | 2 | 45.3 |
| NN0223285 | 2 | 45.3 |
| NN0223271 | 2 | 45.3 |
| SSR00218 | 2 | 50.3 |
| NN0225358 | 2 | 50.3 |
| NN0224573 | 2 | 51.6 |
| NN0226986 | 2 | 51.6 |
| NN0224027 | 2 | 51.7 |
| NN0228028 | 2 | 51.7 |
| SSR17814 | 2 | 52.8 |
| SSR12083 | 2 | 52.8 |
| NN0225190 | 2 | 52.8 |
| NN0246702 | 2 | 53.3 |
| NN0224844 | 2 | 53.9 |
| SSR16941 | 2 | 55.5 |
| SSR11468 | 2 | 55.5 |
| SSR22227 | 2 | 55.5 |
| NN0227695 | 2 | 55.5 |
| NN0227700 | 2 | 55.6 |
| NN0228748 | 2 | 56.1 |
| NN0246318 | 2 | 56.4 |
| NN0247210 | 2 | 56.4 |
| SSR02634 | 2 | 56.4 |
| NN0223380 | 2 | 56.4 |
| NN0223398 | 2 | 56.4 |
| NN0247233 | 2 | 56.9 |
| NN0246696 | 2 | 57.4 |
| NN0223463 | 2 | 57.6 |
| SSR23732 | 2 | 57.6 |
| NN0223494 | 2 | 57.6 |
| NN0223465 | 2 | 57.7 |
| NN0224617 | 2 | 58.0 |
| NN0224658 | 2 | 58.3 |
| SSR05492 | 2 | 59.5 |
| NN0246763 | 2 | 59.5 |
| NN0224594 | 2 | 60.9 |
| SSR02322 | 2 | 66.5 |
| SSR07278 | 2 | 66.5 |
| SSR11909 | 2 | 66.5 |
| SSR16135 | 2 | 66.5 |
| SSR22653 | 2 | 66.5 |
| NN0247695 | 2 | 66.5 |
| SSR00009 | 2 | 67.0 |
| SSR06913 | 2 | 67.0 |
| NN0227962 | 2 | 67.0 |
| NN0226717 | 2 | 67.1 |
| NN0247305 | 2 | 67.2 |
| NN0226038 | 2 | 68.0 |
| NN0225776 | 2 | 68.5 |
| NN0247544 | 2 | 69.7 |
| NN0227412 | 2 | 69.8 |
| NN0247350 | 2 | 69.9 |
| NN0247798 | 2 | 70.0 |
| SSR13131 | 2 | 70.0 |
| NN0228560 | 2 | 70.0 |
| NN0226406 | 2 | 72.4 |
| SSR21734 | 2 | 73.2 |
| NN0227242 | 2 | 73.2 |
| SSR00507 | 2 | 73.7 |
| NN0247636 | 2 | 73.7 |
| NN0226006 | 2 | 73.8 |
| SSR15873 | 2 | 74.6 |
| NN0225709 | 2 | 74.6 |
| NN0224913 | 2 | 74.6 |
| SSR12227 | 2 | 76.3 |
| SSR18362 | 2 | 76.3 |
| NN0228448 | 2 | 76.3 |
| SSR21655 | 2 | 78.0 |
| SSR05420 | 2 | 78.0 |
| SSR19851 | 2 | 78.0 |
| NN0225027 | 2 | 78.0 |
| NN0225018 | 2 | 78.0 |
| NN0227692 | 2 | 78.5 |
| NN0247139 | 2 | 78.5 |
| NN0223317 | 2 | 78.8 |
| NN0223824 | 2 | 78.9 |
| NN0223452 | 2 | 79.5 |
| NN0246284 | 2 | 79.7 |
| NN0246771 | 2 | 79.7 |
| NN0223209 | 2 | 79.7 |
| NN0223221 | 2 | 79.7 |
| NN0226547 | 2 | 79.8 |
| NN0247618 | 2 | 80.3 |
| SSR01253 | 2 | 80.5 |

TABLE 19-continued

Genetic map positions of SNP ("NN0 . . . ") and SSR markers of cucumber chromosomes 2, 4, and 5, from alignment of SSR markers onto consensus scaffold-based genetic map. See also FIG. 5.

| Marker Name | Chromosome # | Map position |
|---|---|---|
| NN0228741 | 2 | 80.5 |
| NN0226471 | 2 | 80.5 |
| NN0226327 | 2 | 81.0 |
| NN0226885 | 2 | 81.6 |
| NN0246708 | 2 | 81.6 |
| NN0228685 | 2 | 81.6 |
| NN0228974 | 2 | 81.7 |
| NN0246681 | 2 | 82.1 |
| NN0226957 | 2 | 82.4 |
| NN0223181 | 2 | 82.4 |
| SSR21276 | 2 | 83.0 |
| NN0227214 | 2 | 83.0 |
| NN0225257 | 2 | 84.4 |
| NN0223574 | 2 | 85.8 |
| NN0226638 | 2 | 88.4 |
| NN0226673 | 2 | 88.5 |
| NN0228750 | 2 | 88.6 |
| NN0246924 | 2 | 90.4 |
| SSR30665 | 2 | 91.5 |
| NN0224981 | 2 | 91.5 |
| NN0224804 | 2 | 91.5 |
| SSR13754 | 2 | 96.1 |
| SSR16462 | 2 | 96.1 |
| NN0223703 | 2 | 96.1 |
| SSR16028 | 2 | 96.1 |
| NN0247710 | 4 | 0.0 |
| NN0247539 | 4 | 0.0 |
| NN0247697 | 4 | 0.4 |
| SSR07782 | 4 | 0.4 |
| NN0228009 | 4 | 0.4 |
| NN0224680 | 4 | 0.7 |
| NN0226973 | 4 | 2.4 |
| SSR01949 | 4 | 4.1 |
| SSR07209 | 4 | 4.1 |
| NN0247583 | 4 | 4.1 |
| NN0228802 | 4 | 4.1 |
| SSR19115 | 4 | 4.4 |
| NN0246810 | 4 | 4.4 |
| NN0228736 | 4 | 4.4 |
| NN0247706 | 4 | 5.2 |
| SSR14498 | 4 | 5.2 |
| NN0225810 | 4 | 6.3 |
| NN0224596 | 4 | 6.3 |
| NN0225493 | 4 | 6.3 |
| NN0247492 | 4 | 6.6 |
| SSR19380 | 4 | 9.6 |
| SSR21062 | 4 | 9.6 |
| NN0225975 | 4 | 9.6 |
| SSR22231 | 4 | 9.6 |
| NN0224796 | 4 | 9.8 |
| NN0224711 | 4 | 9.8 |
| NN0228893 | 4 | 9.8 |
| SSR11074 | 4 | 12.5 |
| SSR17427 | 4 | 12.5 |
| NN0223763 | 4 | 12.5 |
| NN0225383 | 4 | 14.4 |
| NN0228856 | 4 | 14.5 |
| NN0228862 | 4 | 14.5 |
| NN0246870 | 4 | 20.0 |
| NN0225260 | 4 | 20.3 |
| SSR00012 | 4 | 20.6 |
| NN0227442 | 4 | 20.6 |
| NN0223863 | 4 | 20.6 |
| NN0225012 | 4 | 20.6 |
| SSR17024 | 4 | 21.7 |
| NN0226079 | 4 | 21.7 |
| NN0247573 | 4 | 21.7 |
| NN0228250 | 4 | 21.9 |
| NN0246309 | 4 | 22.1 |
| NN0246393 | 4 | 24.6 |
| NN0229054 | 4 | 25.4 |
| NN0225572 | 4 | 25.5 |
| SSR13023 | 4 | 25.5 |
| NN0228579 | 4 | 25.8 |
| SSR22706 | 4 | 25.8 |
| NN0225143 | 4 | 25.8 |
| NN0224450 | 4 | 26.8 |
| NN0226440 | 4 | 27.9 |
| NN0226451 | 4 | 27.9 |
| NN0223404 | 4 | 28.7 |
| NN0226964 | 4 | 28.7 |
| NN0225345 | 4 | 29.7 |
| NN0226204 | 4 | 29.8 |
| NN0223589 | 4 | 29.8 |
| NN0227018 | 4 | 29.9 |
| NN0247182 | 4 | 30.1 |
| NN0227010 | 4 | 30.1 |
| NN0247596 | 4 | 30.1 |
| NN0226074 | 4 | 30.1 |
| SSR02803 | 4 | 30.4 |
| SSR07236 | 4 | 30.4 |
| NN0225088 | 4 | 30.4 |
| NN0225150 | 4 | 30.4 |
| NN0224867 | 4 | 30.5 |
| NN0224838 | 4 | 30.5 |
| NN0224343 | 4 | 30.5 |
| SSR21240 | 4 | 30.5 |
| SSR33769 | 4 | 30.5 |
| NN0229028 | 4 | 30.5 |
| NN0224864 | 4 | 30.5 |
| NN0227999 | 4 | 31.3 |
| NN0228029 | 4 | 31.3 |
| NN0227972 | 4 | 31.5 |
| NN0224664 | 4 | 31.9 |
| NN0223316 | 4 | 31.9 |
| NN0224593 | 4 | 31.9 |
| NN0247603 | 4 | 31.9 |
| SSR16892 | 4 | 33.0 |
| NN0226218 | 4 | 33.0 |
| NN0226219 | 4 | 33.0 |
| NN0247330 | 4 | 33.0 |
| NN0224445 | 4 | 33.9 |
| NN0227979 | 4 | 33.9 |
| NN0224221 | 4 | 34.4 |
| NN0223413 | 4 | 35.3 |
| NN0224932 | 4 | 35.5 |
| NN0224414 | 4 | 35.5 |
| NN0224320 | 4 | 35.5 |
| NN0228842 | 4 | 35.5 |
| NN0228836 | 4 | 35.5 |
| NN0247551 | 4 | 35.5 |
| NN0227183 | 4 | 35.5 |
| NN0247666 | 4 | 35.6 |
| NN0227879 | 4 | 35.8 |
| NN0224535 | 4 | 35.8 |
| NN0246369 | 4 | 35.8 |
| NN0223339 | 4 | 35.8 |
| SSR01904 | 4 | 36.5 |
| SSR16847 | 4 | 36.5 |
| NN0223895 | 4 | 36.5 |
| NN0228796 | 4 | 37.3 |
| SSR19044 | 4 | 37.3 |
| NN0223620 | 4 | 37.5 |
| NN0247100 | 4 | 37.6 |
| NN0247134 | 4 | 37.6 |
| NN0246357 | 4 | 40.3 |
| NN0246914 | 4 | 40.3 |
| NN0225107 | 4 | 40.5 |
| SSR15731 | 4 | 42.1 |
| SSR21644 | 4 | 42.1 |
| NN0247712 | 4 | 42.1 |
| NN0224464 | 4 | 42.6 |
| NN0228630 | 4 | 43.2 |
| NN0224762 | 4 | 43.4 |
| NN0224390 | 4 | 44.5 |
| NN0229090 | 4 | 44.5 |
| NN0247725 | 4 | 45.8 |
| NN0246832 | 4 | 46.0 |

TABLE 19-continued

Genetic map positions of SNP ("NN0 . . . ") and SSR markers of cucumber chromosomes 2, 4, and 5, from alignment of SSR markers onto consensus scaffold-based genetic map. See also FIG. 5.

| Marker Name | Chromosome # | Map position |
|---|---|---|
| NN0224211 | 4 | 46.0 |
| NN0225000 | 4 | 46.5 |
| NN0225070 | 4 | 46.6 |
| NN0225551 | 4 | 46.6 |
| NN0247208 | 4 | 47.4 |
| NN0225339 | 4 | 48.1 |
| SSR04385 | 4 | 49.5 |
| NN0228715 | 4 | 49.5 |
| NN0228035 | 4 | 49.8 |
| NN0226692 | 4 | 49.9 |
| NN0224961 | 4 | 49.9 |
| NN0226732 | 4 | 50.0 |
| NN0227475 | 4 | 50.3 |
| NN0225125 | 4 | 50.3 |
| NN0226656 | 4 | 50.5 |
| NN0227120 | 4 | 50.5 |
| NN0227873 | 4 | 50.5 |
| NN0223888 | 4 | 50.5 |
| NN0229056 | 4 | 50.5 |
| NN0247743 | 4 | 50.5 |
| NN0228883 | 4 | 50.8 |
| SSR11043 | 4 | 51.9 |
| NN0247689 | 4 | 51.9 |
| NN0223084 | 4 | 53.7 |
| SSR13456 | 4 | 53.7 |
| NN0225084 | 4 | 53.9 |
| NN0226586 | 4 | 53.9 |
| NN0247529 | 4 | 54.5 |
| SSR17270 | 4 | 54.5 |
| NN0247635 | 4 | 54.5 |
| NN0247342 | 4 | 54.5 |
| NN0247771 | 4 | 54.5 |
| NN0228536 | 4 | 54.8 |
| NN0223375 | 4 | 56.2 |
| NN0226446 | 4 | 56.9 |
| NN0224702 | 4 | 62.4 |
| NN0224353 | 4 | 62.4 |
| NN0227422 | 4 | 62.4 |
| NN0228031 | 4 | 62.4 |
| NN0227154 | 4 | 62.4 |
| NN0223414 | 4 | 62.4 |
| NN0224265 | 4 | 65.5 |
| SSR05125 | 4 | 65.9 |
| SSR07130 | 4 | 65.9 |
| NN0224287 | 4 | 65.9 |
| NN0226863 | 4 | 66.0 |
| NN0228562 | 4 | 66.0 |
| NN0224234 | 4 | 66.0 |
| NN0247077 | 4 | 66.0 |
| NN0225482 | 4 | 66.5 |
| NN0225553 | 4 | 66.5 |
| NN0224572 | 4 | 66.9 |
| NN0224106 | 4 | 66.9 |
| NN0224111 | 4 | 66.9 |
| NN0228930 | 4 | 66.9 |
| NN0223654 | 4 | 66.9 |
| NN0225081 | 4 | 67.1 |
| NN0223940 | 4 | 67.1 |
| NN0227048 | 4 | 67.1 |
| NN0246425 | 4 | 67.1 |
| NN0224538 | 4 | 67.1 |
| NN0228639 | 4 | 68.1 |
| SSR21501 | 4 | 69.1 |
| NN0225543 | 4 | 69.1 |
| NN0228032 | 4 | 69.1 |
| NN0226556 | 4 | 69.1 |
| NN0226509 | 4 | 69.9 |
| NN0227631 | 4 | 71.0 |
| NN0227617 | 4 | 71.0 |
| NN0223626 | 4 | 71.6 |
| NN0223094 | 4 | 71.6 |
| NN0223832 | 4 | 71.6 |
| NN0247543 | 4 | 72.0 |
| NN0224652 | 4 | 74.4 |
| SSR07269 | 4 | 74.4 |
| NN0224067 | 4 | 75.8 |
| NN0226776 | 4 | 75.8 |
| NN0227379 | 4 | 75.8 |
| NN0227315 | 4 | 75.8 |
| NN0224041 | 4 | 75.8 |
| SSR00299 | 4 | 75.8 |
| NN0228602 | 4 | 75.8 |
| NN0223124 | 4 | 76.6 |
| NN0223103 | 4 | 77.5 |
| NN0225814 | 4 | 78.5 |
| NN0228853 | 4 | 78.9 |
| NN0227015 | 4 | 78.9 |
| NN0223942 | 4 | 79.9 |
| NN0246738 | 4 | 81.7 |
| NN0224495 | 4 | 82.0 |
| SSR01552 | 4 | 84.4 |
| NN0225766 | 4 | 84.4 |
| NN0247668 | 4 | 84.4 |
| SSR22948 | 4 | 84.4 |
| NN0226086 | 4 | 84.4 |
| SSR04534 | 4 | 84.4 |
| NN0223539 | 4 | 84.6 |
| NN0227261 | 4 | 84.6 |
| NN0227251 | 4 | 84.6 |
| NN0226226 | 4 | 85.1 |
| NN0246452 | 4 | 85.7 |
| NN0226543 | 4 | 85.9 |
| NN0227762 | 4 | 85.9 |
| NN0247486 | 4 | 85.9 |
| SSR07550 | 4 | 86.2 |
| NN0224069 | 4 | 86.2 |
| NN0227587 | 4 | 87.4 |
| NN0227182 | 4 | 87.4 |
| NN0227279 | 4 | 87.4 |
| NN0227285 | 4 | 87.4 |
| NN0247726 | 4 | 87.6 |
| SSR13159 | 4 | 87.6 |
| NN0247782 | 4 | 87.6 |
| NN0225419 | 4 | 88.0 |
| NN0227265 | 4 | 88.0 |
| NN0223422 | 4 | 88.2 |
| NN0246417 | 4 | 88.2 |
| NN0247615 | 4 | 88.7 |
| NN0247555 | 4 | 88.7 |
| NN0227211 | 4 | 88.7 |
| SSR07543 | 4 | 89.4 |
| NN0226481 | 4 | 89.4 |
| NN0226465 | 4 | 89.6 |
| NN0224223 | 4 | 90.0 |
| NN0226865 | 4 | 90.0 |
| SSR17406 | 4 | 91.3 |
| NN0228648 | 4 | 91.3 |
| SSR14257 | 4 | 91.3 |
| NN0225826 | 4 | 91.6 |
| NN0224777 | 4 | 92.0 |
| NN0224050 | 4 | 92.4 |
| NN0227419 | 4 | 92.9 |
| NN0228716 | 4 | 92.9 |
| NN0223906 | 4 | 92.9 |
| NN0227718 | 4 | 94.3 |
| SSR16315 | 4 | 94.3 |
| NN0227942 | 4 | 94.5 |
| NN0247421 | 4 | 94.5 |
| NN0225077 | 4 | 94.5 |
| NN0223715 | 4 | 94.5 |
| NN0223710 | 4 | 94.5 |
| NN0228566 | 4 | 94.7 |
| NN0225541 | 4 | 94.7 |
| NN0225476 | 4 | 94.7 |
| NN0227586 | 4 | 95.7 |
| NN0225015 | 4 | 96.5 |
| NN0228246 | 4 | 96.6 |
| SSR02233 | 4 | 96.7 |

TABLE 19-continued

Genetic map positions of SNP ("NN0 . . . ") and SSR markers of cucumber chromosomes 2, 4, and 5, from alignment of SSR markers onto consensus scaffold-based genetic map. See also FIG. 5.

| Marker Name | Chromosome # | Map position |
|---|---|---|
| NN0225079 | 4 | 96.7 |
| NN0226312 | 4 | 96.7 |
| NN0227403 | 4 | 96.7 |
| SSR23770 | 4 | 96.7 |
| NN0223754 | 4 | 97.3 |
| NN0223896 | 4 | 97.5 |
| NN0226628 | 4 | 97.8 |
| NN0225404 | 4 | 98.0 |
| NN0225471 | 4 | 98.0 |
| NN0224793 | 4 | 98.0 |
| NN0226220 | 4 | 98.0 |
| NN0225734 | 4 | 98.1 |
| NN0226011 | 4 | 98.2 |
| NN0225208 | 4 | 98.2 |
| NN0228805 | 4 | 98.2 |
| NN0223571 | 4 | 98.4 |
| NN0224125 | 4 | 98.4 |
| NN0224127 | 4 | 98.4 |
| NN0246631 | 4 | 98.4 |
| SSR16292 | 4 | 98.9 |
| SSR29080 | 4 | 98.9 |
| NN0246416 | 4 | 98.9 |
| NN0246722 | 4 | 99.7 |
| NN0246308 | 4 | 99.7 |
| NN0247688 | 4 | 99.7 |
| NN0247613 | 4 | 100.1 |
| SSR22155 | 4 | 100.2 |
| NN0225987 | 4 | 100.2 |
| NN0247623 | 4 | 100.4 |
| NN0223759 | 4 | 100.5 |
| NN0227111 | 4 | 100.5 |
| NN0223284 | 4 | 100.6 |
| NN0223295 | 4 | 100.6 |
| NN0224972 | 4 | 100.6 |
| NN0246321 | 4 | 100.6 |
| NN0226554 | 4 | 100.6 |
| SSR06347 | 4 | 100.6 |
| NN0228925 | 4 | 100.6 |
| SSR15203 | 4 | 100.8 |
| NN0226376 | 4 | 100.8 |
| SSR21197 | 4 | 100.8 |
| NN0226559 | 4 | 101.3 |
| SSR14015 | 4 | 101.3 |
| NN0225554 | 4 | 101.4 |
| NN0223718 | 4 | 101.4 |
| NN0223742 | 4 | 101.4 |
| NN0227971 | 5 | 0.0 |
| NN0226380 | 5 | 0.2 |
| NN0224416 | 5 | 0.2 |
| NN0224425 | 5 | 0.2 |
| NN0247032 | 5 | 0.4 |
| NN0227159 | 5 | 0.4 |
| NN0227081 | 5 | 0.5 |
| SSR14247 | 5 | 0.7 |
| NN0227163 | 5 | 0.7 |
| SSR17022 | 5 | 0.9 |
| NN0247383 | 5 | 0.9 |
| NN0227849 | 5 | 1.0 |
| NN0247369 | 5 | 1.0 |
| NN0227216 | 5 | 1.1 |
| NN0227224 | 5 | 1.1 |
| NN0226775 | 5 | 1.2 |
| NN0226854 | 5 | 1.3 |
| SSR13086 | 5 | 2.0 |
| NN0227542 | 5 | 2.0 |
| NN0224662 | 5 | 2.2 |
| NN0223648 | 5 | 2.2 |
| NN0223632 | 5 | 2.2 |
| NN0228445 | 5 | 2.3 |
| NN0229042 | 5 | 2.3 |
| NN0223496 | 5 | 2.5 |
| NN0225635 | 5 | 2.5 |
| NN0224047 | 5 | 2.6 |
| NN0223877 | 5 | 2.6 |
| NN0224052 | 5 | 2.7 |
| NN0227420 | 5 | 4.3 |
| NN0223296 | 5 | 5.1 |
| SSR22469 | 5 | 5.1 |
| SSR19538 | 5 | 5.9 |
| NN0224657 | 5 | 5.9 |
| SSR02454 | 5 | 9.6 |
| NN0225945 | 5 | 9.6 |
| NN0226455 | 5 | 9.6 |
| SSR12467 | 5 | 9.6 |
| SSR19719 | 5 | 9.6 |
| NN0226450 | 5 | 9.6 |
| NN0226658 | 5 | 9.9 |
| NN0224159 | 5 | 9.9 |
| NN0226797 | 5 | 9.9 |
| NN0227362 | 5 | 9.9 |
| NN0224785 | 5 | 9.9 |
| NN0228078 | 5 | 9.9 |
| NN0226536 | 5 | 9.9 |
| NN0226528 | 5 | 9.9 |
| NN0228505 | 5 | 10.0 |
| NN0226756 | 5 | 10.0 |
| NN0223780 | 5 | 10.0 |
| NN0247311 | 5 | 10.2 |
| NN0227594 | 5 | 10.2 |
| SSR16032 | 5 | 10.2 |
| NN0225849 | 5 | 10.2 |
| NN0227145 | 5 | 10.2 |
| SSR10002 | 5 | 10.3 |
| SSR16842 | 5 | 10.3 |
| NN0223450 | 5 | 10.3 |
| NN0224763 | 5 | 14.2 |
| NN0227468 | 5 | 14.6 |
| NN0228918 | 5 | 14.6 |
| NN0226418 | 5 | 14.6 |
| NN0225926 | 5 | 14.6 |
| NN0225883 | 5 | 14.6 |
| NN0228145 | 5 | 14.7 |
| NN0227295 | 5 | 14.7 |
| NN0226387 | 5 | 14.7 |
| NN0227584 | 5 | 15.0 |
| NN0246349 | 5 | 15.1 |
| NN0227168 | 5 | 15.8 |
| SSR01859 | 5 | 15.8 |
| NN0227165 | 5 | 15.8 |
| SSR00023 | 5 | 16.1 |
| NN0226433 | 5 | 16.1 |
| SSR00398 | 5 | 16.1 |
| NN0223950 | 5 | 16.4 |
| SSR19998 | 5 | 16.4 |
| NN0246612 | 5 | 17.6 |
| NN0224029 | 5 | 17.6 |
| SSR01610 | 5 | 17.6 |
| SSR20648 | 5 | 17.6 |
| NN0246303 | 5 | 17.6 |
| SSR22172 | 5 | 17.6 |
| NN0227653 | 5 | 17.6 |
| NN0226303 | 5 | 17.6 |
| NN0228175 | 5 | 17.7 |
| SSR07369 | 5 | 17.7 |
| NN0227913 | 5 | 18.9 |
| SSR20208 | 5 | 18.9 |
| NN0246687 | 5 | 18.9 |
| NN0223949 | 5 | 18.9 |
| NN0224861 | 5 | 18.9 |
| NN0224841 | 5 | 18.9 |
| NN0223182 | 5 | 19.0 |
| SSR10795 | 5 | 19.0 |
| NN0225294 | 5 | 20.3 |
| NN0225315 | 5 | 20.3 |
| NN0229134 | 5 | 21.6 |
| NN0227380 | 5 | 21.6 |
| NN0225199 | 5 | 21.7 |
| NN0225904 | 5 | 21.7 |

TABLE 19-continued

Genetic map positions of SNP ("NN0 . . . ") and SSR markers of cucumber chromosomes 2, 4, and 5, from alignment of SSR markers onto consensus scaffold-based genetic map. See also FIG. 5.

| Marker Name | Chromosome # | Map position |
|---|---|---|
| NN0224426 | 5 | 21.8 |
| NN0226415 | 5 | 22.2 |
| NN0225222 | 5 | 22.8 |
| SSR13639 | 5 | 22.8 |
| NN0225428 | 5 | 22.8 |
| NN0226841 | 5 | 22.8 |
| SSR03341 | 5 | 24.5 |
| SSR05819 | 5 | 24.5 |
| SSR07559 | 5 | 24.5 |
| NN0228879 | 5 | 24.5 |
| NN0226553 | 5 | 25.3 |
| NN0223140 | 5 | 25.3 |
| NN0227540 | 5 | 25.3 |
| NN0228457 | 5 | 25.6 |
| NN0228069 | 5 | 26.2 |
| SSR07057 | 5 | 26.7 |
| NN0225531 | 5 | 26.7 |
| SSR10348 | 5 | 26.7 |
| SSR03950 | 5 | 28.1 |
| SSR11167 | 5 | 28.1 |
| NN0228895 | 5 | 28.1 |
| NN0224856 | 5 | 29.0 |
| NN0226092 | 5 | 29.9 |
| NN0247223 | 5 | 30.1 |
| NN0246356 | 5 | 30.4 |
| NN0224773 | 5 | 31.1 |
| NN0225532 | 5 | 31.2 |
| NN0225517 | 5 | 31.2 |
| NN0229077 | 5 | 31.2 |
| SSR20895 | 5 | 31.2 |
| NN0229137 | 5 | 31.2 |
| NN0224304 | 5 | 31.7 |
| NN0247509 | 5 | 31.7 |
| NN0227435 | 5 | 31.7 |
| NN0227405 | 5 | 31.7 |
| SSR23615 | 5 | 31.9 |
| SSR10542 | 5 | 31.9 |
| SSR14051 | 5 | 31.9 |
| SSR21861 | 5 | 31.9 |
| NN0228317 | 5 | 31.9 |
| NN0223802 | 5 | 32.3 |
| SSR20487 | 5 | 32.3 |
| NN0227305 | 5 | 33.2 |
| SSR18593 | 5 | 33.5 |
| NN0223112 | 5 | 33.5 |
| NN0228982 | 5 | 33.5 |
| NN0247183 | 5 | 33.5 |
| NN0246332 | 5 | 33.8 |
| NN0224476 | 5 | 33.9 |
| NN0224325 | 5 | 34.5 |
| NN0227981 | 5 | 36.1 |
| NN0247085 | 5 | 37.4 |
| NN0226041 | 5 | 37.4 |
| NN0226671 | 5 | 37.4 |
| NN0224375 | 5 | 37.6 |
| NN0223399 | 5 | 38.6 |
| SSR23101 | 5 | 39.1 |
| NN0224283 | 5 | 39.1 |
| SSR11750 | 5 | 39.7 |
| NN0224246 | 5 | 39.7 |
| NN0247066 | 5 | 40.4 |
| NN0228739 | 5 | 40.4 |
| NN0228814 | 5 | 40.5 |
| NN0225803 | 5 | 40.9 |
| NN0247244 | 5 | 41.0 |
| NN0223974 | 5 | 41.0 |
| NN0224213 | 5 | 41.0 |
| NN0224193 | 5 | 41.0 |
| NN0224669 | 5 | 41.0 |
| SSR07284 | 5 | 41.0 |
| NN0227571 | 5 | 41.2 |
| NN0227555 | 5 | 41.2 |
| NN0227525 | 5 | 41.3 |
| NN0223689 | 5 | 41.4 |
| SSR14269 | 5 | 41.4 |
| NN0223687 | 5 | 41.4 |
| NN0226194 | 5 | 41.6 |
| NN0226187 | 5 | 41.6 |
| NN0227343 | 5 | 42.3 |
| NN0227129 | 5 | 42.3 |
| NN0228943 | 5 | 42.3 |
| NN0228968 | 5 | 42.3 |
| SSR19178 | 5 | 43.0 |
| NN0225790 | 5 | 43.0 |
| SSR10720 | 5 | 44.8 |
| NN0224377 | 5 | 44.8 |
| SSR12921 | 5 | 44.8 |
| NN0226709 | 5 | 44.8 |
| NN0246677 | 5 | 45.2 |
| NN0224642 | 5 | 45.2 |
| NN0247731 | 5 | 45.2 |
| NN0224840 | 5 | 45.2 |
| NN0226013 | 5 | 45.6 |
| NN0227895 | 5 | 46.1 |
| NN0224349 | 5 | 46.1 |
| SSR15893 | 5 | 47.8 |
| NN0227665 | 5 | 47.8 |
| NN0226326 | 5 | 48.9 |
| NN0229099 | 5 | 48.9 |
| NN0225940 | 5 | 48.9 |
| NN0225518 | 5 | 49.0 |
| NN0225544 | 5 | 49.1 |
| NN0226346 | 5 | 49.2 |
| NN0226508 | 5 | 49.2 |
| NN0246770 | 5 | 49.3 |
| SSR07711 | 5 | 49.4 |
| SSR21291 | 5 | 49.4 |
| NN0223897 | 5 | 49.4 |
| SSR23148 | 5 | 49.4 |
| SSR23132 | 5 | 49.4 |
| SSR32717 | 5 | 49.4 |
| NN0224455 | 5 | 49.4 |
| SSR16110 | 5 | 49.4 |
| NN0226166 | 5 | 50.0 |
| NN0228693 | 5 | 51.7 |
| NN0246672 | 5 | 51.7 |
| NN0226430 | 5 | 51.7 |
| NN0227495 | 5 | 52.3 |
| NN0225480 | 5 | 53.2 |
| NN0225654 | 5 | 53.2 |
| NN0227497 | 5 | 53.2 |
| SSR15321 | 5 | 53.3 |
| NN0223392 | 5 | 53.3 |
| NN0224442 | 5 | 53.7 |
| NN0225103 | 5 | 54.3 |
| NN0224698 | 5 | 54.3 |
| NN0227581 | 5 | 55.5 |
| NN0247308 | 5 | 55.6 |
| NN0225661 | 5 | 55.9 |
| NN0226631 | 5 | 55.9 |
| NN0224600 | 5 | 55.9 |
| NN0246411 | 5 | 56.1 |
| NN0223215 | 5 | 56.2 |
| NN0226316 | 5 | 56.2 |
| NN0228725 | 5 | 56.3 |
| NN0246410 | 5 | 56.3 |
| NN0223921 | 5 | 56.5 |
| NN0229142 | 5 | 56.8 |
| NN0226764 | 5 | 57.4 |
| NN0224228 | 5 | 57.7 |
| NN0224229 | 5 | 57.7 |
| NN0224406 | 5 | 58.3 |
| NN0225311 | 5 | 58.6 |
| NN0229148 | 5 | 59.9 |
| Cs28 | 5 | 60.1 |
| NN0227759 | 5 | 60.1 |
| NN0223336 | 5 | 60.3 |
| SSR15818 | 5 | 60.3 |

TABLE 19-continued

Genetic map positions of SNP ("NN0 . . . ") and SSR markers of cucumber chromosomes 2, 4, and 5, from alignment of SSR markers onto consensus scaffold-based genetic map. See also FIG. 5.

| Marker Name | Chromosome # | Map position |
|---|---|---|
| NN0225562 | 5 | 60.3 |
| NN0247548 | 5 | 60.6 |
| NN0224461 | 5 | 60.7 |
| NN0227603 | 5 | 60.7 |
| NN0246604 | 5 | 60.9 |
| NN0247389 | 5 | 60.9 |
| NN0246347 | 5 | 61.4 |
| NN0247348 | 5 | 61.9 |
| NN0226809 | 5 | 62.6 |
| NN0226762 | 5 | 62.6 |
| NN0247445 | 5 | 62.7 |
| NN0223334 | 5 | 67.1 |
| NN0225936 | 5 | 68.4 |
| NN0225451 | 5 | 68.4 |
| NN0224327 | 5 | 68.4 |
| NN0246449 | 5 | 68.4 |
| NN0228465 | 5 | 68.4 |
| NN0223507 | 5 | 68.6 |
| SSR02244 | 5 | 68.6 |
| NN0246335 | 5 | 69.1 |
| SSR06660 | 5 | 69.1 |
| NN0224251 | 5 | 69.6 |
| SSR17464 | 5 | 69.6 |
| NN0246571 | 5 | 69.6 |
| NN0224832 | 5 | 71.1 |
| SSR23706 | 5 | 71.3 |
| SSR03529 | 5 | 71.3 |
| SSR07184 | 5 | 71.3 |
| NN0226931 | 5 | 71.3 |
| NN0228305 | 5 | 71.6 |
| NN0247786 | 5 | 71.8 |
| SSR07100 | 5 | 71.8 |
| NN0227082 | 5 | 71.8 |
| SSR19172 | 5 | 71.8 |
| NN0247485 | 5 | 71.9 |
| NN0227153 | 5 | 72.5 |
| SSR00772 | 5 | 72.5 |
| NN0227421 | 5 | 72.5 |
| NN0223866 | 5 | 72.5 |
| SSR00670 | 5 | 73.6 |
| SSR01498 | 5 | 73.6 |
| SSR04816 | 5 | 73.6 |
| NN0224048 | 5 | 73.6 |
| SSR20859 | 5 | 73.6 |
| NN0227318 | 5 | 73.9 |
| NN0226912 | 5 | 74.1 |
| NN0226871 | 5 | 74.4 |
| NN0227924 | 5 | 74.4 |
| NN0223640 | 5 | 74.4 |
| NN0226104 | 5 | 74.4 |
| NN0223518 | 5 | 75.1 |
| NN0247794 | 5 | 75.1 |
| NN0226645 | 5 | 75.2 |
| NN0223160 | 5 | 75.4 |
| NN0227504 | 5 | 75.5 |
| NN0228997 | 5 | 75.5 |
| NN0226525 | 5 | 75.5 |
| NN0224248 | 5 | 75.5 |
| NN0224226 | 5 | 75.5 |
| NN0228632 | 5 | 75.5 |
| NN0247702 | 5 | 75.5 |
| NN0229017 | 5 | 75.5 |
| NN0225600 | 5 | 75.5 |
| NN0223755 | 5 | 75.6 |
| NN0225793 | 5 | 75.7 |
| NN0226053 | 5 | 75.7 |
| NN0246483 | 5 | 75.7 |
| NN0246327 | 5 | 76.1 |
| SSR14180 | 5 | 76.1 |
| NN0226354 | 5 | 76.7 |
| NN0228464 | 5 | 76.7 |
| SSR00648 | 5 | 76.9 |
| CSWCT17 | 5 | 76.9 |
| SSR26904 | 5 | 76.9 |
| NN0226186 | 5 | 76.9 |
| NN0223789 | 5 | 77.0 |
| NN0223809 | 5 | 77.0 |
| NN0226623 | 5 | 77.2 |
| NN0223634 | 5 | 77.2 |
| NN0246814 | 5 | 77.2 |
| NN0227194 | 5 | 77.3 |
| NN0225426 | 5 | 77.4 |
| NN0225876 | 5 | 77.4 |
| NN0226156 | 5 | 77.4 |
| NN0247406 | 5 | 77.6 |
| NN0246437 | 5 | 77.8 |
| NN0223864 | 5 | 77.8 |
| NN0246426 | 5 | 77.8 |
| SSR17975 | 5 | 77.8 |
| NN0223659 | 5 | 77.9 |
| NN0226257 | 5 | 77.9 |
| NN0225344 | 5 | 77.9 |
| SSR20486 | 5 | 77.9 |
| NN0246586 | 5 | 77.9 |
| NN0226429 | 5 | 78.0 |
| NN0225867 | 5 | 78.0 |
| NN0225673 | 5 | 78.0 |
| NN0228260 | 5 | 78.0 |
| NN0225717 | 5 | 78.0 |
| NN0247058 | 5 | 78.1 |
| NN0223685 | 5 | 78.1 |
| NN0223699 | 5 | 78.1 |
| NN0223091 | 5 | 78.1 |
| NN0226394 | 5 | 78.2 |
| NN0225216 | 5 | 78.2 |
| NN0247709 | 5 | 78.3 |
| NN0247443 | 5 | 78.3 |
| NN0224090 | 5 | 78.3 |
| NN0223081 | 5 | 78.3 |
| SSR06303 | 5 | 78.6 |
| NN0225646 | 5 | 78.6 |
| NN0225626 | 5 | 78.6 |
| NN0229147 | 5 | 78.6 |
| NN0229106 | 5 | 78.6 |
| NN0229020 | 5 | 78.6 |
| NN0228957 | 5 | 78.6 |
| NN0247140 | 5 | 78.6 |
| NN0227071 | 5 | 78.7 |
| NN0246376 | 5 | 78.7 |
| NN0224281 | 5 | 78.7 |
| NN0226051 | 5 | 78.7 |
| NN0226076 | 5 | 78.7 |
| NN0223859 | 5 | 79.1 |
| NN0247574 | 5 | 79.1 |
| SSR13237 | 5 | 79.3 |
| NN0226937 | 5 | 79.3 |
| NN0226940 | 5 | 79.3 |
| NN0247180 | 5 | 79.4 |
| NN0247563 | 5 | 79.5 |
| NN0247704 | 5 | 79.5 |
| NN0247447 | 5 | 79.5 |
| NN0247630 | 5 | 79.5 |
| NN0224507 | 5 | 80.0 |
| NN0247388 | 5 | 80.1 |
| NN0224321 | 5 | 80.1 |
| NN0225878 | 5 | 80.1 |
| NN0224365 | 5 | 80.1 |
| NN0225310 | 5 | 80.1 |
| NN0227929 | 5 | 80.3 |
| NN0224031 | 5 | 80.6 |
| NN0228710 | 5 | 80.7 |
| NN0224991 | 5 | 80.7 |
| NN0226870 | 5 | 80.7 |
| NN0228616 | 5 | 80.7 |
| NN0226516 | 5 | 80.8 |
| NN0226453 | 5 | 81.0 |
| NN0226540 | 5 | 81.4 |
| NN0227287 | 5 | 81.5 |

TABLE 19-continued

Genetic map positions of SNP ("NN0 . . . ") and SSR markers of cucumber chromosomes 2, 4, and 5, from alignment of SSR markers onto consensus scaffold-based genetic map. See also FIG. 5.

| Marker Name | Chromosome # | Map position |
|---|---|---|
| NN0227228 | 5 | 81.5 |
| SSR03514 | 5 | 81.5 |
| SSR21219 | 5 | 81.5 |
| NN0228055 | 5 | 81.5 |
| NN0246331 | 5 | 81.8 |
| NN0227097 | 5 | 81.8 |
| NN0246889 | 5 | 81.8 |
| NN0224713 | 5 | 81.8 |
| NN0228255 | 5 | 81.8 |
| NN0224443 | 5 | 81.8 |
| NN0228289 | 5 | 81.8 |
| NN0225431 | 5 | 81.9 |
| NN0227769 | 5 | 82.0 |
| NN0226910 | 5 | 82.0 |
| NN0227655 | 5 | 82.0 |
| SSR02895 | 5 | 82.1 |
| SSR16143 | 5 | 82.1 |
| NN0226391 | 5 | 82.1 |
| SSR19343 | 5 | 82.1 |
| NN0247172 | 5 | 82.6 |
| NN0228132 | 5 | 82.6 |
| NN0226532 | 5 | 82.6 |
| NN0228148 | 5 | 82.7 |
| SSR03758 | 5 | 82.7 |
| NN0226082 | 5 | 82.7 |

Example 10

Development of QIR Mapping Population

A recombinant inbred line (RIL) mapping population, termed "QIR", generated from an initial cross between the Downy Mildew susceptible parent 05VA8409 (a line that was resistant to Powdery Mildew and Cucurbit Yellow Stunting Disorder Virus, CYSDV) and a Downy Mildew resistant parent derived from PI-197088 was used to examine the genetics of cucumber Downy Mildew (CDM) resistance. The 40 lines in the population were phenotyped at $F_4$ and $F_5$ generations in Saint-Andiol, France. Previous QTL-mapping analyses with this data identified a major QTL for CDM resistance on a linkage group, defined in this population as "IV," which was later found to correspond to chromosome 5. Fine-mapping with CAPS markers suggested two linked QTLs at 35.8 cM and 42.7 cM on the genetic map generated from this population, within this region on chromosome 5.

Based on the three QTLs on chromosomes 2, 4, and 5, identified for CDM using the API and VJ mapping populations (e.g. see Examples 7-8) which share the PI-197088 Downy Mildew resistant parent, the $F_6$ generation of this cross was genotyped with 60 markers spaced roughly evenly across these three chromosomes, in order to validate these three QTLs in the QIR population. For each of the $F_4$ and $F_5$ generation trials, 10 mature plants of each Fn family were planted and tested for resistance to natural infections of downy mildew (*Pseudoperonospora cubensis*) in a randomised block design of three replicates. For the $F_4$ trial, each $F_4$ family received an overall disease score for each of the three replicates. For the $F_5$ trial, each plant received a disease score for each of the three replicates. Disease scores ranged from 2 (susceptible) to 8 (resistant). Sex determination was observed to be segregating in the $F_4$ families. For analysis of the QIR mapping population, the raw phenotypic data from the $F_4$ and $F_5$ trials were adjusted to account for replicate effects (and sex determination in the $F_4$). In all, 40 families had non-missing phenotype value in at least one of the $F_4$ or $F_5$ trials.

A total of 60 SNPs were genotyped on 301 $F_6$ samples corresponding to 38 unique $F_6$ lines. Seven or eight plants of each RIL were genotyped, and both phenotypic and genotypic data were used in this analysis. Eight samples of the susceptible parent were also genotyped. Consensus genotypes were deduced based on the following criterion: for each locus, if genotypes were not consistent across all replicate samples (plants of the same RIL), the genotype occurring in more than 50% of the samples was taken as the consensus; otherwise a "missing" genotype designation was given to the locus. Of the 60 tested markers, 28 were monomorphic (not segregating) in the $F_6$ population and were excluded from further analysis. Table 20 provides a summary of the markers used.

TABLE 20

Marker summary; 32 informative markers were genotyped across 38 F6 RILs and used.

| Chr | Total # Genotyped Markers | # Segregating Loci | Average inter-marker spacing (cM) | Max. inter-marker spacing (cM) |
|---|---|---|---|---|
| 2 | 12 | 5 | 4.5 | 7.7 |
| 4 | 25 | 16 | 3.7 | 8.7 |
| 5 | 23 | 11 | 5.0 | 19.7 |
| Total | 60 | 32 | 4.3 | 19.7 |

A non-parametric approach based on the Kruskal-Wallis test (Kruskal and Wallis, *J. Amer. Statistical Assoc.* 47: 583-621, 1952) and Haley-Knott regression (Haley & Knott, *Heredity* 69:315-324, 1992) was used to test for the presence of a QTL at every 1 cM interval. Identical phenotypic values between RILs were assigned averaged ranks. Conditional genotype probabilities were estimated based on observed multiple-point marker data using the Hidden Markov algorithm and the Kosambi map function. Significance was determined from permutation tests within 1,000 permutations at $\alpha=0.05$. All QTL-mapping analyses were performed using R/QTL (Broman et al., *Bioinformatics* 19:889-890, 2003).

Example 11

QTL Analysis for QIR Population

Figure 6:
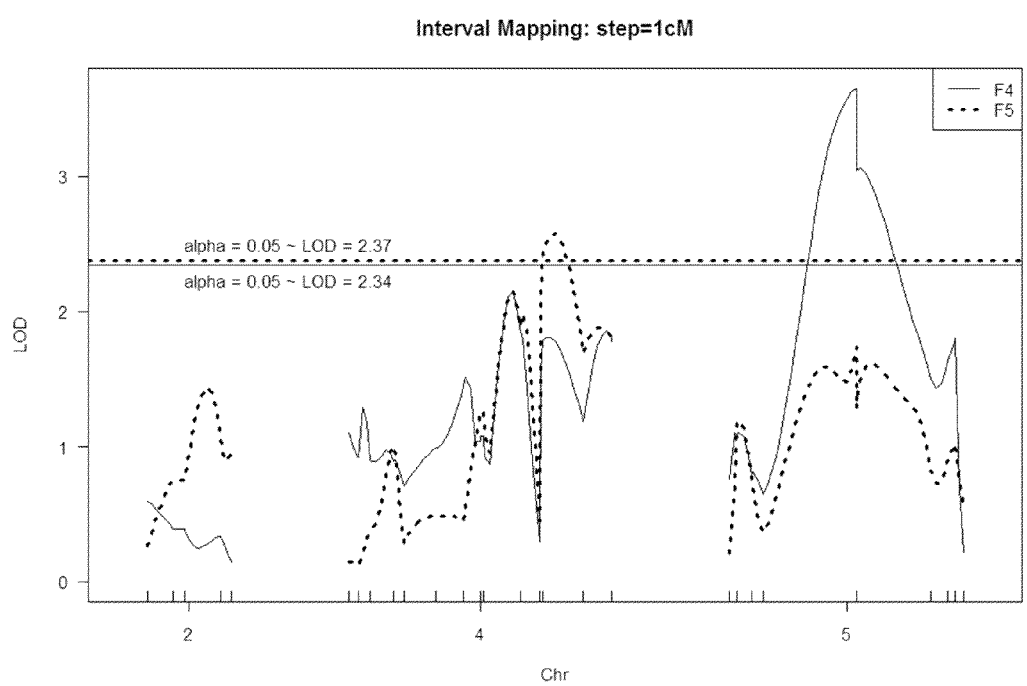
FIG. 6 Interval mapping and LOD scores for QTLs of chromosomes 2, 4, and 5, analyzed in F4 and F5 generations of the QIR mapping population. Shown are the LOD scores from the single-QTL mapping analysis for phenotypes collected from the $F_4$ (solid line) and $F_5$ (dotted line) generations of the QIR mapping population. The two horizontal lines indicate the $\alpha=0.05$ permutation thresholds from 1,000 permutations for the two datasets. "Chr" referens to chromosome.
Figure 7:
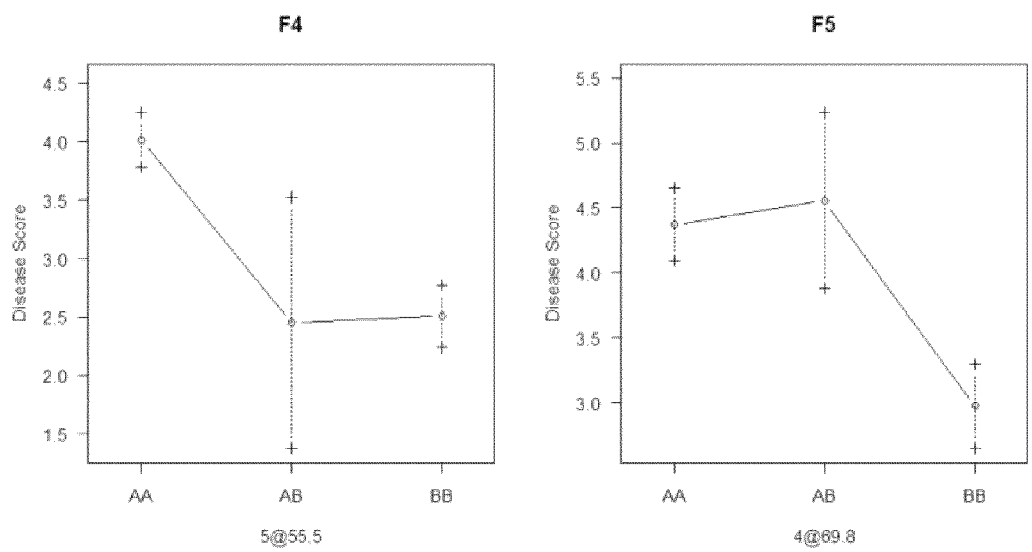
FIG. 7. Plots of $F_4$ and $F_5$ Downy Mildew pathogenicity test scores in the QIR mapping population, means against genotypes at the corresponding QTLs. The QTL identified from the $F_4$ data was at Chr5:55.5 cM and the QTL identified from the $F_5$ data was at Chr4:69.8 cM. Error bars correspond to ±1 standard error.

Two different QTLs were identified at Chr5:55.5 cM and Chr4:70 cM for CDM resistance collected from the $F_4$ and $F_5$ QIR populations respectively (FIG. 6 & Table 21). No significant linkage to Downy Mildew resistance was detected on Chr2 for either of the $F_4$ or $F_5$ datasets in the QIR population. For both QTLs on chromosomes 4 and 5, resistance was conferred by the allele corresponding to the resistant parent: each resistant allele was estimated to reduce disease score by ~0.7, suggesting an effect of 1.4 disease units per QTL (Table 21 & FIG. 7).

TABLE 21

QTLs for cucumber Downy Mildew resistance identified using
phenotypes from the $F_4$ and $F_5$ QIR populations.

| Generation | F4 | F5 |
|---|---|---|
| Chromosome | 5 | 4 |
| Position (cM) | 55.5 | 69.8 |
| LOD | 3.65 | 2.58 |
| P-value (1,000 permutations) | 0.000 | 0.026 |
| % Variation Explained | 36.80 | 25.53 |
| Additive Effect | −0.76 | −0.70 |
| Dominance Effect | −1.25 | 1.09 |
| Closest Marker | NN0226631 | NN0246425 |
| Distance to Closest Marker | 0.0 | 2.7 |
| Population Mean | 3.34 | 3.88 |
| Donor Allele Mean | 4.02 | 4.38 |
| Susceptible Allele Mean | 2.49 | 2.96 |
| 1-LOD interval (cM) | 45.5-62.5 | 56.8-82.0 |
| 1-LOD Flanking Markers | NN0227981-NN0247786 | NN0247342-NN0224495 |
| 2-LOD interval (cM) | 41.5-77.5 | 31.8-82.0 |
| 2-LOD Flanking Markers | NN0227981-NN0227071 | NN0225088-NN0224495 |
| 3-LOD interval (cM) | 28.5-78.3 | 25.8-82.0 |
| 3-LOD Flanking Markers | NN0224856-NN0227071 | NN0228579-NN0224495 |

Because these two QTLs on chromosomes 4 and 5 have been consistently identified in the API, VJ, and QIR populations, these two QTLs appear to act additively or epistatically in the genetic control of Downy Mildew-resistance. The following epistatic model was tested: Downy Mildew resistance ~Q1+Q2+Q1×Q2, where Q1 corresponds to the Chr4:69.8 cM QTL and Q2 corresponds to the Chr5:55.5 cM QTL. While the full model was found to be significant for both the $F_4$ and $F_5$ data (P-value of the F-statistic was 0.016 and 0.015 respectively), examination of the sub-models revealed that only one term of the model was significant (P<0.05) in each case: only Q2 was significant for the $F_4$ dataset and only Q1 was significant for the $F_5$ dataset.

Figure 8:
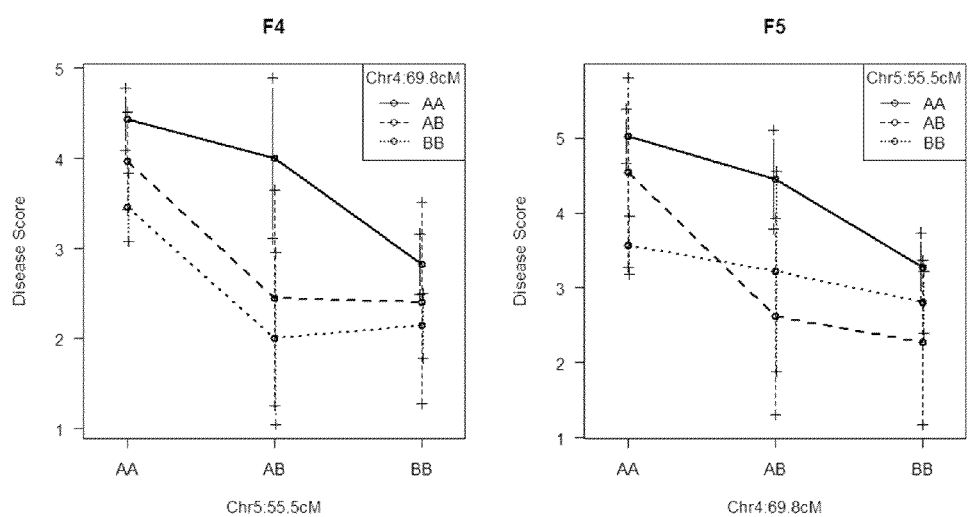
FIG. 8. Interaction plots between the two QTLs for Downy mildew resistance in the QIR population. In each plot, the three genotypes on the x-axis correspond to the QTL identified using the corresponding datasets. The three genotypes (AA, AB, and BB) of the alternate QTL are indicated by solid, dashed, or dotted lines, respectively. Error bars correspond to ±1 standard error.

Of the three QTLs (Chr2:21.8-73.8 cM, Chr4:13.8-87.6 cM, Chr5:22.6-81.0 cM) previously identified using the API and VJ mapping populations, two (one on Chr4 and one on Chr5) were also identified in the current QIR population. The two QTL regions are found to be relatively large. That is, even at 1-LOD intervals, the two QTLs are predicted to reside within ~20 cM. No significant epistatic interaction was identified between these two QTLs, suggesting these two QTLs may have an additive effect on Downy Mildew resistance (FIG. 8).

Example 12

Fine Mapping of QTLs for Downy Mildew Resistance on Chromosomes 2, 4, and 5

Further fine mapping of QTLs of chromosomes 2, 4, and 5 conferring resistance to cucmber Downy Mildew was carried out in conjunction with the QTL analyses described above (e.g. Table 19). Fine mapping with the following markers on chromosome 2 (with map positions in parentheses): NNO246378 (14.554); NNO227646 (19.999); NNO223782 (22.448); NNO226279 (26.487); NNO246831 (28.802); NNO226670 (30.115); NNO224124 (32.406); NNO247070 (34.669); NNO227137 (36.613); NNO247472 (38.441); NNO227700 (55.622); and NNO247695 (66.466) indicated that the CDM QTL on chromosome 2 extends between map positions 14.5-66.4 cM, including 14.5-38.4 cM, based on results from the QIR mapping population.

Fine mapping with the following markers on chromosome 4 (with map positions in parentheses): NNO225012 (20.649); NNO228579 (25.816); NNO226451 (27.944); NNO225088 (30.428); NNO247551 (35.460); NNO247100 (37.638); NNO224390 (44.531); NNO225551 (46.644); NNO228715 (49.546); NNO227475 (50.320); NNO227873 (50.477); NNO228883 (50.812); NNO223084 (53.747); NNO226586 (53.869); NNO247342 (54.495); NNO224702 (62.385); NNO224265 (65.543); NNO225482 (66.478); NNO225553 (66.478); NNO223940 (67.148); NNO246425 (67.148); NNO224041 (75.834); NNO224495 (81.973); NNO227587 (87.395); and NNO246631 (98.405) indicated that the CDM QTL on chromosome 4 extends between map positions 56.8-82.0 cM with a 1-LOD interval, or between 31.8-82.0 cM with a 2-LOD interval, or between 25.8-82.0 cM with a 3-LOD interval, based on results from the QIR mapping population.

Fine mapping with the following markers on chromosome 5 (with map positions in parentheses): NN5096749 (25.200); NNO228457 (25.235); NNO224856 (28.544); NNO246356 (30.032); NNO225532 (30.761); NNO228982 (33.131); NNO227981 (35.718); NNO223689 (41.014); NNO225790 (42.626); NNO246677 (44.758); NNO247731 (44.780); NNO226326 (48.512); NN5096750 (51.200); NN0246672 (51.326); NN0224442 (53.297); NN0226631 (55.452); NN0224600 (55.452); NN0246411 (55.649); NN0247786 (71.424); NN0223160 (74.955); NN0223809 (76.617); NN0227071 (78.303); and NN0228148 (82.273) indicated that the CDM QTL on chromosome 5 extends between map positions 45.5-62.5 cM with a 1-LOD interval, or between 41.5-77.5 cM with a 2-LOD interval, or between 28.5-78.3 cM with a 3-LOD interval, based on results from the QIR mapping population.

Thus, the QTL of chromosome 2 may extend between map positions 14.5-66.4 cM, or between 14.5-38.4 cM. Likewise, the QTL of chromosome 4 may extend from 13.8-87.6 cM, or between 25.8-82.0 cM. or between 31.8-75.8 cM. The QTL of chromosome 5 may likewise extend from 22.6-81.0 cM, or between 25.2-78.3 cM, or between 28.5-75.0 cM.

Example 13

Refinement of QTL Intervals for Downy Mildew Resistance and Development of Backcross Lines with Genetic Recombination Events Across the QTLs In order to identify sub-region(s) from the previously identified QTL intervals (e.g. on chromosomes 2, 4, and/or 5) that are highly associated with DM resistance, introgression regions from PI197088 were identified in 61 DM resistant lines developed from two different germplasm classes. For both germplasm classes, the resistant lines presented introgressed regions in the three QTL regions, supporting the utility of the identified QTLs for conferring resistance to DM in breeding material. For each QTL interval, regions with relatively high frequency marker alleles found in PI197088 were observed; these introgressed regions are likely to contain the QTLs conferring DM resistance, or markers that are highly associated with these QTLs. The regions highly associated with DM resistance were found to include: QTL2: 14.554-38.4 cM; QTL4: 44.531-66.478 cM; and QTL5: 25.235-42.626 and 53.297-71.424 cM.

A plant with resistance to DM, in this case, a progeny plant of PI197088, referred to as the donor parent (DP), was crossed to plants from several DM susceptible, elite inbred lines, referred to as recurrent parents ("RP's"). Plants of the $F_1$ generation from such a cross were backcrossed to plants of each RP to form the backcross 1 ($BC_1$) generation. In each RP pedigree, 40 to 50 $BC_1$ plants were backcrossed to RP plants to form the $BC_2$ generation. This occurred before initial identification of the DM QTL.

When markers for the DM resistance QTL of chromosome 4 ("QTL04") and the DM resistance QTL of chromosome 5 ("QTL05") were developed, remnant tissue from each $BC_1$ plant was genotyped, and plants heterozygous for the QTLs were identified. $BC_2$ progeny plants from DM QTL heterozygous $BC_1$ plants were genotyped with markers at the distal ends of each DM QTL. Using this data, $BC_2$ plants were selected that contained genetic recombination events within one of the DM QTL, while displaying a homozygous RP allele at the other DM QTL. These plants were self-pollinated in a greenhouse to create the $BC_2F_2$ generation. In the following crop cycle, $BC_2F_2$ plants from each recombinant $BC_2$ pedigree were genotyped with markers in the DM QTL, selected for homozygosity of the favorable allele in the recombinant section of the DM QTL, and self pollinated to create the $BC_2F_3$ generation. Each $BC_2F_3$ family was uniformly homozygous for the DP allele in the recombinant section of one DM QTL, and homozygous RP for the other QTL, in order to confer a uniform phenotype for DM within each family. The recombinant $BC_2F_3$ families could then be phenotyped for DM with four experimental controls consisting of $BC_2F_3$ lines that had been selected for presence of only unfavorable (RP) alleles at both QTL04 and QTL05 (null control); presence of unfavorable allele at QTL04, favorable allele at QTL05; presence of favorable allele at QTL04, unfavorable allele at QTL05; presence of favorable allele at both QTL04 and QTL05. Data can then be analyzed in a series of paired tests between the controls and the $BC_2F_3$ families. The genotypes of $BC_2F_3$ recombinant families showing DM resistance significantly better than the null control are evaluated for location of the region containing the favorable allele in the DM QTL. If all $BC_2F_3$ families sharing this genotype show superior DM resistance, that genetic interval is defined as containing the DM QTL. Through comparison of multiple $BC_2F_3$ families with different, but overlapping recombinant fragments, a smaller genetic and physical region containing the DM QTL is identifed. Additional genetic markers utilized in refining the map positions of the DM QTLs are listed in Table 22. Such markers are utilized with various mapping populations, such as QIR, API, or VJ, among others.

TABLE 22

Exemplary additional *C. sativus* genomic DNA sequences flanking the sites of SNP markers linked to QTLs on chromosomes 2, 4, and 5, for refining QTL map positions.

| Marker Name | Chromosome; map position | Genomic DNA Sequence (SEQ ID NOs: 70-87). SNP site with polymorphism is given within brackets. |
|---|---|---|
| NN0246378 | 2; 14.554 | AATGACTTATCTAGATGGATATGATAACTTCACCGATTGTTGGATAAA AAAGCAGGTGAC[A/G]AGTTGTGTTATTATTGGGCAGTGATGTATTG TTAGnTAACCACTGAAATTGTTAAAATTA |
| NN0224041 | 4; 75.834 | TCTTTAAAAGAAGCTTGAAAGATGAAGAAATTGCAAAATTTCAATCAT TTCGATCCCTCC[A/T]CTCACCTGAAAAAGTGGTTAATTCTGATGAT TTTAGATCATGGTCCATTGATCCCTCAAT |
| NN0227587 | 4; 87.395 | ATTTTTAGATGTGAGCCTATTTATGTGCTCTTAACTTCTCTTTTAGTA ATGGTGGAAATG[T/C]AATTTGTTTATGAGCAATGGTATCGTGAATA AATGGTTGGATACATAATAGCTTTGCTTG |
| NN5096749 | 5; 25.200 | ACTAGGTCGTGGGATGTCGTTGGGGGACATGTTAAATCCATGGCTGTC TA[G/A]AAGGAATTTCCATATCATTGAGATCTAGGTGCACAAATTCC TCGAACCTA |
| NN0224856 | 5; 28.544 | GGACATTCTTCACATAAATCAGAATTGTCGTACACAACCCAAAATTCT CCAATTAGCTAA[T/C]AGCGTTACAGATCTTCTTTTCCGCTTCTTTC CACGATGTATTGATATAGTGTGCCCTGAA |
| NN0223160 | 5; 74.955 | AATGCAACAATTCTTTCAGCTAAGGAGAAGAAAGAAGCAAAAGAAAGA AAACACTCCACC[T/C]CTAGCCATTGCCCATCATCCATCTAAATTTC TTACTAAGATGCATAATATCTTCCACATA |
| NN0223809 | 5; 76.617 | GGAGATTGTTGCACGCCTGAAGAAAGCCTTCAGAATTACCATTAAGAC TTCCCAACTCTG[T/C]CTGCATATTGTCAAGAAAGCTAGAGATTTTC TCAGAAGCTACTTTAATGGCAGGGCCCTC |
| NN0226631 | 5; 55.452 | GTCAAAAAGGTCAAGTCCACACTCCTCAGCTTATGAATCAAAACCCTG CACAGAAGGGAA[A/T]CACAACAACATTTTCAACTTTTCAGCTTAAC TTTTGGCAATCATCAGGTTAAACAGACTT |

TABLE 22-continued

Exemplary additional *C. sativus* genomic DNA sequences flanking the sites of SNP markers linked to QTLs on chromosomes 2, 4, and 5, for refining QTL map positions.

| Marker Name | Chromosome; map position | Genomic DNA Sequence (SEQ ID NOs: 70-87). SNP site with polymorphism is given within brackets. |
|---|---|---|
| NN0227981 | 5; 35.718 | GGATTAATTTGCAAAAACCTTAAGTCGGGGAATTAGGGCTAAAGAGGA ATTAAGGTAGAA[T/G]TGATTACCCCTGAGGATTATTGAAGGATAAA TTGAGTTGTGATTGATTAGCGAAATAACC |
| NN0247786 | 5; 71.424 | TTAGGTTCCCGCTATTGCAATACCAACAAGGCATGAAGGCTTT[C/G] GCCACAATGTGAAATCATCAACAGTTACTATGAACAATGAATTCGCTA ACAGGAAAnCGT |
| NN0246425 | 4; 67.148 | GAAGTAAGTTGCCTGCTTCTCTTTTTTTCACTAGGAATTGCTATTCAG ACAGTTATATGC[A/T]CATTTCCAATGGTGCTTTTTTGTTCATTGTT TTCAATGTTGGGATTGACATCTGTCTGAA |
| NN0224495 | 4; 81.973 | ACGAATTTTCTAGTTGAGTCAAGTCAGGTTGGTTGGAAAGTGTTATCA GAATATGTCAGT[A/G]CTTGTCAACTCTCGCACTCTCTTTTGAGGCT ATAAAGTTAGAGAAGAGTCTCTAGGAAGG |
| NN0225088 | 4; 30.428 | GAGTTTCCAAAATTGAACATCTTCAATGGACAGAAAGTTTTGAAGTAG CAAGACTTAAGG[T/C]TTCCACTTGGTGTTCCTTATCTAAGTTCTCG AACAATTTGCATTTGATTTCTTAAATATT |
| NN0227071 | 5; 78.303 | AGGAAAATACCTTCCAATAGAAAACATGGTAAATGCAATAAGCATCTA GTTCATCCAATT[C/G]CAAGGGTAATGGCTAGTTCAAGATGGAACTA AAACTCTCAGAGTGGTGTGTGCAATCCTG |
| NN0223782 | 2; 22.448 | TTCATACGCCGTTGCAGCTGAAAGTGGCAACCATTACTTCCAGATCAT TATGACAATAAA[T/C]AACCAAGGCCACCTTCATGCATAAATGGTAA GATAATAGCAAGCTCTATACCTTCTTTTT |
| NN0228579 | 4; 25.816 | ACTCATATTTACAGAAAACTTACTCTAAACCACAAGTCCTTAACAAAT ATATTTCTGCTT[C/G]CGGCTCTCTTCCTATCATGAAATTTTGCAAG CTATTCAGAAAATCC |
| NN0247342 | 4; 54.495 | GTACTTGTACCAATATGAAATGTGCACATGCGCTCTTGTCCTAGATAA TATGCACAGTTC[A/T]CCTTAAAAGCTAAGCATAAGCCACAAATCCA AGAACCAATGTAACCAAAACAGTATGGGA |
| NN0247731 | 5; 44.780 | TGAAGAAGAGCCTTTATTGCGTCATCTGGAACCTCCTTTATCCATTTA TCTTGAATTGGT[T/C]GGTCATGAACACACCTTTACCATTTATTATT CAATGCCATGATTGTCTTACACAGGTGTG |

Initial mapping of the DM QTL used data from two $F_5$ populations referred to as the API and VJ populations. Mean DM scores from several trials for families in the API population were tested for significant differences from the population mean. Families with DM scores significantly higher or lower than the population mean were selected. Plants from each of these families were genotyped and selected for homozygosity across the DM QTL. The selected plants would also be genotyped for genome-wide markers to define, in particular, regions that shifted from heterozygous in the $F_5$ family to homozygous in the selected $F_5$ plant and derived $F_6$ family. These plants were self pollinated to create $F_6$ families. These families are phenotyped along with experimental controls of the DM-susceptible parent of the API population, the DM-resistant parent of the population (PI197088), and the four experimental controls described previously, consisting of $BC_2F_3$ lines that had been selected for presence of only unfavorable (RP) alleles at both QTL04 and QTL05 (null control); presence of unfavorable allele at QTL04, favorable allele at QTL05; presence of favorable allele at QTL04, unfavorable allele at QTL05; presence of favorable allele at both QTL04 and QTL05. This analysis allows for improved resolution of the genetic positions of the QTL intervals, and detection of additional QTL contributing to DM resistance. By changing genotypes in DM QTL from heterozygous in the $F_5$ family to homozygous in the derived $F_6$ more uniform DM phenotypes are displayed, thus enhancing resolution of genotype-phenotype associations.

What is claimed is:

1. A method of obtaining cucumber germplasm comprising the steps of:
   a) assaying cucumber plants for the presence of at least a first genetic marker genetically linked to a QTL that confers resistance to Downy Mildew; and
   b) selecting at least a first cucumber plant comprising the genetic marker and the QTL that confers resistance to Downy Mildew;

wherein the QTL maps to a position between the sequence represented by SNP marker NN0228457 and SNP marker NN0228148, which map to approximately 25.2 cM and 82.7 cM on the genetic map of the linkage group termed cucumber chromosome 5, respectively; wherein the QTL maps to a position between the sequence represented by SNP marker NN0225012 and SNP marker NN0227587 which map to approximately 20.6 cM and 87.4 cM on the genetic map of the linkage group termed cucumber chromosome 4, respectively; or wherein the QTL maps to a position between the sequence represented by SNP marker NN0223782 and SNP marker NN0226638 which map to approximately 22.5 cM and 88.4 cM on the genetic map of the linkage group termed cucumber chromosome 2, respectively.

2. The method of claim 1, wherein the QTL maps to a position between the sequence represented by SNP marker NN0227981 and SNP marker NN0226631, which map to approximately 35.7 cM and 55.5 cM on the genetic map of the linkage group termed cucumber chromosome 5, respectively; or wherein the QTL maps to a position between the sequence represented by SNP marker NN0227981and SNP marker NN0247786, which map to approximately 35.7 cM and 71.4 cM on the genetic map of the linkage group termed cucumber chromosome 5, respectively.

3. The method of claim 1, wherein the QTL maps to a position between the sequence represented by SNP marker NN0228579 and SNP marker NN0224495 which map to approximately 25.8 cM and 82.0 cM on the genetic map of the linkage group termed cucumber chromosome 4, respectively; wherein the QTL maps to a position between the sequence represented by SNP marker NN0225088and SNP marker NN0224041 which map to approximately 30.4 cM and 75.8 cM on the genetic map of the linkage group termed cucumber chromosome 4, respectively; or wherein the QTL maps to a position between the sequence represented by SNP marker NN0228579 and SNP marker NN0224495 which map to approximately 54.5 cM and 82.0 cM on the genetic map of the linkage group termed cucumber chromosome 4,respectively.

4. The method of claim 1, wherein the QTL maps to a position between the sequence represented by SNP marker NN0246378 and SNP marker NN0246472 which map to approximately 14.6 cM and 38.4 cM on the genetic map of the linkage group termed cucumber chromosome 2, respectively.

5. The method of claim 1, wherein the allele which confers resistance to Downy Mildew is derived from cucumber line PI197088, or a progeny plant thereof.

6. The method of claim 1, wherein selecting the first cucumber plant further comprises selecting the plant based on the presence of a plurality of genetic markers that map to a position between the sequence represented by SNP marker NN0228457 and SNP marker NN0228148, which map to approximately 25.2 cM and 82.7 cM on the genetic map of the linkage group termed cucumber chromosome 5, respectively; or wherein the QTL maps to a position between the sequence represented by SNP marker NN0227981 and SNP marker NN0226631, which map to approximately 35.7 cM and 55.5 cM on the genetic map of the linkage group termed cucumber chromosome 5, respectively; or wherein the QTL maps to a position between the sequence represented by SNP marker NN0227981 and SNP marker NN0247786, which map to approximately 35.7 cM and 71.4 cM on the genetic map of the linkage group termed cucumber chromosome 5, respectively; or wherein the QTL maps to a position between the sequence represented by SNP marker NN0225012 and SNP marker NN0227587 which map to approximately 20.6 cM and 87.4 cM on the genetic map of the linkage group termed cucumber chromosome 4, respectively; or wherein the QTL maps to a position between the sequence represented by SNP marker NN0247342 and SNP marker NN0224495 which map to approximately 54.5 cM and 82.0 cM on the genetic map of the linkage group termed cucumber chromosome 4, respectively; or wherein the QTL maps to a position between the sequence represented by SNP marker NN0223782 and SNP marker NN0226638 which map to approximately 22.5 cM and 88.4 cM on the genetic map of the linkage group termed cucumber chromosome 2, respectively.

7. The method of claim 1, wherein the genetic marker is selected from the group consisting of markers NN0223782, NN0225385, NN0226670, NN0224124, NN0246472, NN0225358, NN0227700, NN0224617, NN0247695, NN0227242, NN0223824, NN0223181, NN0226638, NN0225012, NN0228579, NN0226451, NN0225088, NN0226219, NN0247551, NN0246357, NN0225551, NN0226732, NN0247689, NN0247342, NN0224702, NN0225482, NN0224538, NN0247543, NN0224041, NN0228853, NN0227762, NN0227587, NN0228457, NN0246356, NN0246332, NN0223399, NN0223689, NN0247731, NN0226166, NN0225480, NN0246411, NN0227759, NN0247348, NN0228465, NN0247786, NN0226645, NN0223809, NN0227071, NN0226870, NN0228148, NN0246378, NN0224041, NN0227587, NN5096749, NN0224856, NN0223160, NN0223809, NN0226631, NN0227981, NN0247786, NN0246425, NN0224495, NN0225088, NN0227071, NN0223782, NN0228579, NN0247342, and NN0247731, comprising a single nucleotide polymorphism of one of SEQ ID NOs:20-87.

8. The method of claim 7, wherein the genetic marker is selected from the group consisting of markers NN0223782, NN0225385, NN0226670, NN0224124, NN0246472, NN0225358, NN0227700, NN0224617, NN0247695, NN0227242, NN0223824, NN0223181, NN0226638, and NN0246378.

9. The method of claim 7, wherein the genetic marker is selected from the group consisting of markers NN0225012, NN0228579, NN0226451, NN0225088, NN0226219, NN0247551, NN0246357, NN0225551, NN0226732, NN0247689, NN0247342, NN0224702, NN0225482, NN0224538, NN0247543, NN0224041, NN0228853, NN0227762, NN0227587, NN0224041, NN0227587, NN0246425, NN0224495, NN0225088, NN0228579, and NN0247342.

10. The method of claim 7, wherein the genetic marker is selected from the group consisting of markers NN0228457, NN0246356, NN0246332, NN0223399, NN0223689, NN0247731, NN0226166, NN0225480, NN0246411, NN0227759, NN0247348, NN0228465, NN0247786, NN0226645, NN0223809, NN0227071, NN0226870, NN0228148, NN5096749, NN0224856, NN0223160, NN0223809, NN0226631, NN0227981, NN0247786, NN0227071, and NN0247731.

11. The method of claim 1, wherein assaying the cucumber plants comprises PCR, single strand conformational polymorphism analysis, denaturing gradient gel electrophoresis, cleavage fragment length polymorphism analysis, TAQMAN assay, and/or DNA sequencing.

12. The method of claim 1, wherein the genetic marker maps within 20 cM, 10 cM or 1 cM of a QTL which confers resistance to Downy Mildew.

13. The method of claim 1, wherein the genetic marker is NN0226631 or NN0246425.

14. A method of cucumber plant breeding comprising:
a) assaying cucumber plants for the presence of at least a first genetic marker genetically linked to a QTL that confers resistance to Downy Mildew; and
b) selecting at least a first cucumber plant comprising the genetic marker and the QTL that confers resistance to Downy Mildew; wherein the QTL maps to a position between the sequence represented by SNP marker NN0228457 and SNP marker NN0228148, which map to approximately 25.2 cM and 82.7 cM on the genetic map of the linkage group termed cucumber chromosome 5, respectively; wherein the QTL maps to a position between the sequence represented by SNP marker NN0227981 and SNP marker NN0226631, which map to approximately 35.7 cM and 55.5 cM on the genetic map of the linkage group termed cucumber chromosome 5, respectively; wherein the QTL maps to a position between the sequence represented by SNP marker NN0227981 and SNP marker NN0247786, which map to approximately 35.7 cM and 71.4 cM on the genetic map of the linkage group termed cucumber chromosome 5, respectively; wherein the QTL maps to a position between the sequence represented by SNP marker NN0225012 and SNP marker NN0227587 which map to approximately 20.6 cM and 87.4 cM on the genetic map of the linkage group termed cucumber chromosome 4, respectively; wherein the QTL maps to a position between the sequence represented by SNP marker NN0247342 and SNP marker NN0224495 which map to approximately 54.5 cM and 82.0 cM on the genetic map of the linkage group termed cucumber chromosome 4, respectively; or wherein the QTL maps to a position between the sequence represented by SNP marker NN0223782 and SNP marker NN0226638 which map to approximately 22.5 cM and 88.4 cM on the genetic map of the linkage group termed cucumber chromosome 2, respectively; and c) crossing the first cucumber plant with itself or a second cucumber plant to produce progeny cucumber plants comprising the QTL that confers resistance to Downy Mildew.

15. The method of claim 14, wherein selecting at least a first cucumber plant further comprises selecting the plant based on the presence of a plurality of genetic markers that map to a position between the sequence represented by SNP marker NN0228457 and SNP marker NN0228148, which map to approximately 25.2 cM and 82.7 cM on the genetic map of the linkage group termed cucumber chromosome 5, respectively; wherein the QTL maps to a position between the sequence represented by SNP marker NN0227981 and SNP marker NN0226631, which map to approximately 35.7 cM and 55.5 cM on the genetic map of the linkage group termed cucumber chromosome 5, respectively; wherein the QTL maps to a position between the sequence represented by SNP marker NN0227981 and SNP marker NN0247786, which map to approximately 35.7 cM and 71.4 cM on the genetic map of the linkage group termed cucumber chromosome 5, respectively; wherein the QTL maps to a position between the sequence represented by SNP marker NN0225012 and SNP marker NN0227587 which map to approximately 20.6 cM and 87.4 cM on the genetic map of the linkage group termed cucumber chromosome 4, respectively; wherein the QTL maps to a position between the sequence represented by SNP marker NN0247342 and SNP marker NN0224495 which map to approximately 54.5 cM and 82.0 cM on the genetic map of the linkage group termed cucumber chromosome 4, respectively; or wherein the QTL maps to a position between the sequence represented by SNP marker NN0223782 and SNP marker NN 0226638 which map to approximately 22.5 cM and 88.4 cM on the genetic map of the linkage group termed cucumber chromosome 2, respectively.

16. The method of claim 14, further comprising the step of
d) selecting a progeny plant comprising the allele which confers resistance to Downy Mildew and crossing the progeny plant with itself or a third cucumber plant to produce additional progeny plants.

17. The method of claim 16, wherein the method further comprises repeating step (d) about 2-10 times.

18. The method of claim 14, wherein the allele which confers resistance to Downy Mildew is derived from cucumber line PI197088, or a progeny plant thereof.

19. The method of claim 14, wherein the genetic marker is selected from the group consisting of markers NN0223782, NN0225385, NN0226670, NN0224124, NN0246472, NN0225358, NN0227700, NN0224617, NN0247695, NN0227242, NN0223824, NN0223181, NN0226638, NN0225012, NN0228579, NN0226451, NN0225088, NN0226219, NN0247551, NN0246357, NN0225551, NN0226732, NN0247689, NN0247342, NN0224702, NN0225482, NN0224538, NN0247543, NN0224041, NN0228853, NN0227762, NN0227587, NN0228457, NN0246356, NN0246332, NN0223399, NN0223689, NN0247731, NN0226166, NN0225480, NN0246411, NN0227759, NN0247348, NN0228465, NN0247786, NN0226645, NN0223809, NN0227071, NN0226870, NN0228148, NN0246378, NN0224041, NN0227587, NN5096749, NN0224856, NN0223160, NN0223809, NN0226631, NN0227981, NN0247786, NN0246425, NN0224495, NN0225088, NN0227071, NN0223782, NN0228579, NN0247342, and NN0247731, comprising a single nucleotide polymorphism of one of SEQ ID NOs:20-87.

20. The method of claim 19, wherein the genetic marker is selected from the group consisting of markers NN0223782, NN0225385, NN0226670, NN0224124, NN0246472, NN0225358, NN0227700, NN0224617, NN0247695, NN0227242, NN0223824, NN0223181, NN0226638, and NN0246378.

21. The method of claim 19, wherein the genetic marker is selected from the group consisting of markers NN0225012, NN0228579, NN0226451, NN0225088, NN0226219, NN0247551, NN0246357, NN0225551, NN0226732, NN0247689, NN0247342, NN0224702, NN0225482, NN0224538, NN0247543, NN0224041, NN0228853, NN0227762, NN0227587, NN0224041, NN0227587, NN0246425, NN0224495, NN0225088, NN0228579, and NN0247342.

22. The method of claim 19, wherein the genetic marker is selected from the group consisting of markers NN0228457, NN0246356, NN0246332, NN0223399, NN0223689, NN0247731, NN0226166, NN0225480, NN0246411, NN0227759, NN0247348, NN0228465, NN0247786, NN0226645, NN0223809, NN0227071, NN0226870, NN0228148, NN5096749, NN0224856, NN0223160, NN0223809, NN0226631, NN0227981, NN0247786, NN0227071, and NN0247731.

23. The method of claim 14, wherein assaying the cucumber plants comprises PCR, single strand conformational polymorphism analysis, denaturing gradient gel electrophoresis, cleavage fragment length polymorphism analysis, TAQMAN assay, and/or DNA sequencing.

24. The method of claim 14, wherein the genetic marker maps within 20 cM, 10 cM or 1 cM of a QTL which confers resistance to Downy Mildew.

25. The method of claim 14, wherein the genetic marker is NN0226631 or NN0246425.

26. The method of claim 14, wherein the cucumber plant comprising at least one allele which confers resistance to Downy Mildew demonstrates a reduction of foliar symptoms of chlorotic and/or necrotic lesions of at least, or greater than, 25%, relative to a non-resistant control cucumber line.

* * * * *

UNITED STATES PATENT AND TRADEMARK OFFICE
CERTIFICATE OF CORRECTION

PATENT NO. : 8,809,622 B2  Page 1 of 1
APPLICATION NO. : 12/910478
DATED : August 19, 2014
INVENTOR(S) : David Caldwell et al.

It is certified that error appears in the above-identified patent and that said Letters Patent is hereby corrected as shown below:

In the Claims

Column 119, Line 22, Claim 3, please delete "NN0225088and" and insert --NN0225088 and--

Signed and Sealed this
Twenty-seventh Day of January, 2015

Michelle K. Lee
*Deputy Director of the United States Patent and Trademark Office*